(12) United States Patent
Ness et al.

(10) Patent No.: US 9,102,944 B2
(45) Date of Patent: Aug. 11, 2015

(54) METHODS, COMPOSITIONS AND KITS FOR ONE-STEP DNA CLONING USING DNA TOPOISOMERASE

(71) Applicant: DNA Twopointo, Inc., Menlo Park, CA (US)

(72) Inventors: Jon E. Ness, Redwood City, CA (US); Jeremy S. Minshull, Los Altos, CA (US)

(73) Assignee: DNA Twopointo, Inc., Menlo Park, CA (US)

( * ) Notice: Subject to any disclaimer, the term of this patent is extended or adjusted under 35 U.S.C. 154(b) by 0 days.

(21) Appl. No.: 13/649,068

(22) Filed: Oct. 10, 2012

(65) Prior Publication Data
US 2013/0122572 A1  May 16, 2013

Related U.S. Application Data

(62) Division of application No. 12/178,506, filed on Jul. 23, 2008, now Pat. No. 8,323,930.

(60) Provisional application No. 60/962,339, filed on Jul. 28, 2007.

(51) Int. Cl.
| | |
|---|---|
| *C12P 19/34* | (2006.01) |
| *C12Q 1/68* | (2006.01) |
| *C12N 15/66* | (2006.01) |
| *C12N 9/90* | (2006.01) |
| *C12N 15/10* | (2006.01) |
| *C12N 15/64* | (2006.01) |

(52) U.S. Cl.
CPC *C12N 15/66* (2013.01); *C12N 9/90* (2013.01); *C12N 15/10* (2013.01); *C12N 15/64* (2013.01)

(58) Field of Classification Search
None
See application file for complete search history.

(56) References Cited

U.S. PATENT DOCUMENTS

| | | | | |
|---|---|---|---|---|
| 5,736,373 | A * | 4/1998 | Hamilton | 435/194 |
| 6,660,475 | B2 * | 12/2003 | Jack et al. | 435/6.14 |
| 2005/0069929 | A1 * | 3/2005 | Chestnut et al. | 435/6 |
| 2005/0074785 | A1 * | 4/2005 | Slater et al. | 435/6 |

FOREIGN PATENT DOCUMENTS

WO  WO 98/56943  * 12/1998  ............ C12P 19/34

* cited by examiner

*Primary Examiner* — Catherine S Hibbert
(74) *Attorney, Agent, or Firm* — Morgan, Lewis & Bockius LLP

(57) ABSTRACT

Provided are methods, compositions, and kits for cloning of DNA using DNA topoisomerase. The methods comprise (I) combining into a mixture (A) a first polynucleotide comprising an origin of replication, a selectable marker, two topoisomerase recognition sequences, and two nicking agent recognition sequences, each of the topoisomerase recognition sequences being within 50 nucleotides of at least one of the nicking agent recognition sequences and each of the two nicking agent recognition sequences being nicked, with (B) a sequence-specific topoisomerase and (C) a second polynucleotide having 5' hydroxyl on each end; and (II) transforming the mixture into a host organism, thereby cloning the second polynucleotide. Formation or purification of a DNA-protein adduct prior to the addition of the second polynucleotide is not required. Also provided are vector sequences to facilitate performance of the methods and methods for modifying a vector of interest to render it useful in the disclosed methods.

28 Claims, 16 Drawing Sheets

Figure 1:
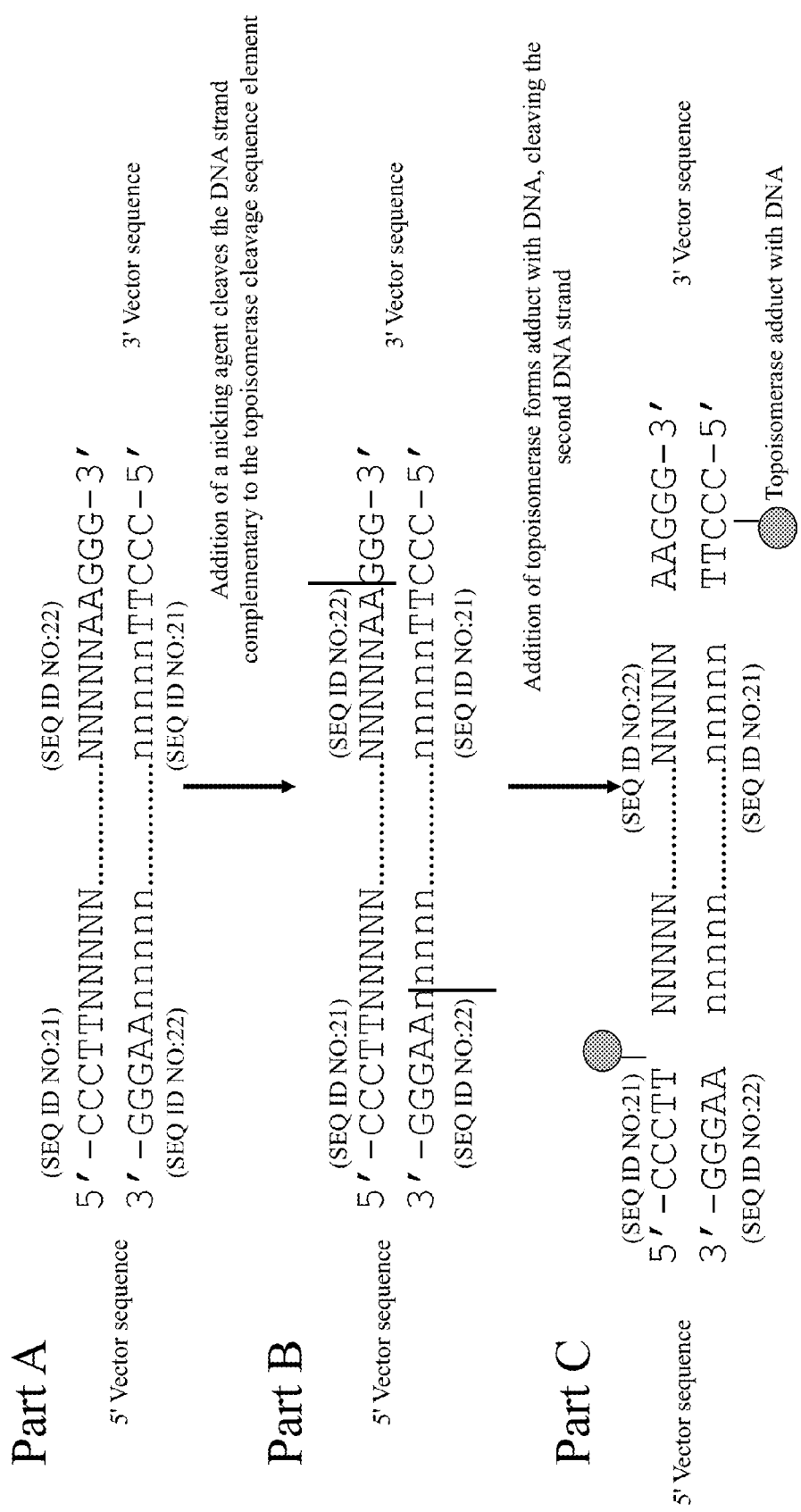

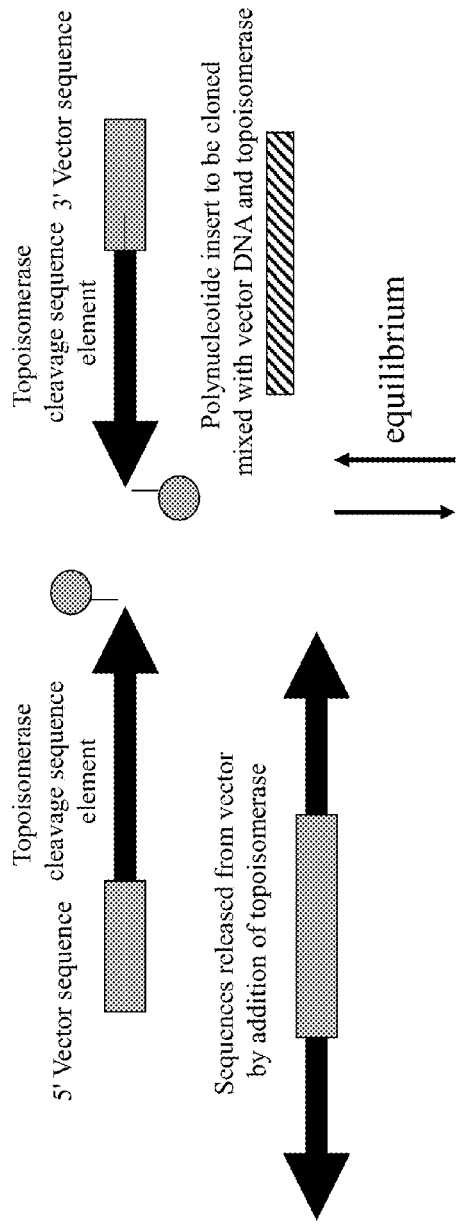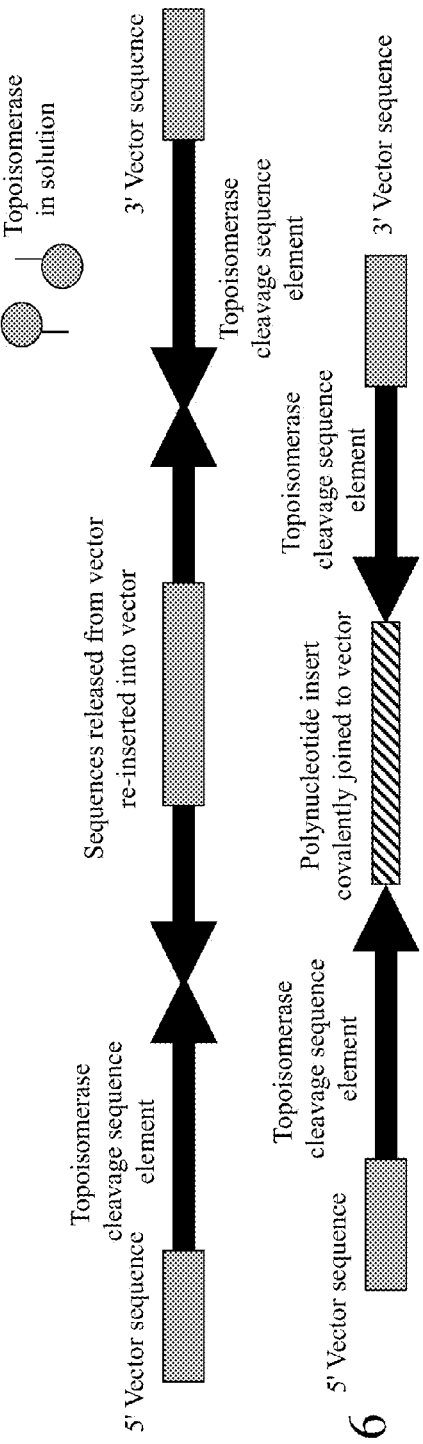
Fig. 6

Fig. 9 (for eg5)

Fig. 11 (for eg5)

Fig. 12 (for eg2)

Fig. 13 (for eg1)

Fig. 14 (for eg7)

METHODS, COMPOSITIONS AND KITS FOR ONE-STEP DNA CLONING USING DNA TOPOISOMERASE

1. CROSS-REFERENCES TO RELATED APPLICATIONS

This application is a divisional of U.S. patent application Ser. No. 12/178,506 filed Jul. 23, 2008, which claims benefit, under 35 U.S.C. §119(e), of U.S. Provisional Patent Application No. 60/962,339 filed on Jul. 28, 2007 which is incorporated by reference herein in its entirety.

2. FIELD OF THE INVENTION

Provided herein are methods, compositions, and kits useful for molecular cloning of, for example, blunt-ended DNA molecules using DNA topoisomerase. In certain embodiments, the methods comprise combining into a mixture a first polynucleotide, wherein said first polynucleotide comprises an origin of replication, a selectable marker, two topoisomerase recognition sequences, and two nicking agent recognition sequences, wherein each of said two topoisomerase recognition sequences is within 0-50 nucleotides of at least one of the nicking agent recognition sequences and wherein each of said two nicking agent recognition sequences is nicked, with a sequence-specific topoisomerase and a second polynucleotide, wherein said second polynucleotide comprises a 5' hydroxyl on each end of the polynucleotide; and transforming the mixture into a host organism, thereby cloning the second polynucleotide. Advantageously, in some embodiments, the methods, compositions, and kits does not require the formation or purification of a DNA-protein adduct prior to the addition of the polynucleotide to be cloned. Also provided are vector sequences to facilitate performance of the methods and methods for modifying a vector of interest to render it useful in the methods described herein.

3. BACKGROUND OF THE INVENTION

The cloning of DNA segments is performed as a daily routine in many research labs; it is frequently also a prerequisite step in genetic analyses or the preparation of DNA constructs for gene expression or regulation. A great deal of time and effort can be expended in the cloning of DNA segments. The basic methods for cloning have been known for many years and have changed little during that time. A typical cloning protocol based on restriction enzyme digestion is as follows: (1) digest the DNA to be cloned with restriction enzymes; (2) purify the digested DNA segment to be cloned; (3) prepare the vector by cutting with appropriate restriction enzymes, treating with alkaline phosphatase, purifying etc., as appropriate; (4) ligate the DNA segment to the vector, with appropriate controls to estimate background of uncut and self-ligated vector; and (5) introduce the resulting vector into a host cell.

Restriction enzyme based cloning has the disadvantage that the DNA to be cloned must not contain sequences within it that are the same as the sequences recognized by the restriction enzymes with which it will be digested. This is often inconvenient, in some cases it may not even be known whether these sites are present within the DNA segment to be cloned since it is often desirable to clone a DNA segment without their full sequences being known; for example DNA segments may be amplified by the polymerase chain reaction when only the sequences at their ends are known. Restriction enzyme based cloning is also time consuming, with the restriction digestion, purification and ligation steps requiring significant incubation times (~1 hour each).

Some of these limitations have been addressed with the introduction of vectors that contain a 3' overhang of a single T residue (Cha et al., 1993. Journal/Gene, 136: 369-370; Ichihara and Kurosawa, 1993. Journal/Gene, 130: 153-154; Ido and Hayami, 1997. Journal/Biosci Biotechnol Biochem, 61: 1766-1767; Zhou and Gomez-Sanchez, 2000. Journal/Curr Issues Mol Biol, 2: 1-7.). These vectors allow inserts with a 3' overhang of a single A residue to be ligated in without the need for restriction digestion. However this procedure requires that the DNA segment to be cloned is amplified with a low fidelity non-proof-reading polymerase, or that a second step subsequent to amplification is performed to add the 3' A residue. The slow ligation step is also still required.

Cloning methods have also been developed in which recombinases are used in vitro to combine vector and insert DNA (Hartley et al., 2000. Journal/Genome Res, 10: 1788-1795.). In this case the DNA segment to be cloned requires the addition of ~25 bp sequences to each end to allow recognition by the recombinase. Again a slow step (~1 hour) is also required, this time to allow the recombinase to act.

An extremely powerful molecular cloning method using vaccinia DNA topoisomerase has been described (Cheng et al., 1998. Journal/Cell, 92: 841-850; Geng et al., 2006. Journal/Mol Biotechnol, 33: 23-28; Heyman et al., 1999. Journal/Genome Res, 9: 383-392; Shuman, 1994. Journal/J Biol Chem, 269: 32678-32684; Shuman, 1998. Journal/Mol Cell, 1: 741-748.) and U.S. Pat. Nos. 5,766,891; 6,548,277; 6,653,106; 6,916,632 and 7,026,141. This method avoids the limitations of alternative cloning methods: PCR amplification products need no modification and the cloning reaction is extremely short (~5 minutes).

Previously described cloning methods using vaccinia topoisomerase require the reaction of a donor DNA molecule with vaccinia DNA topoisomerase enzyme. A tyrosyl residue in the protein (Tyr-274) forms a covalent adduct with the 3' phosphate of the fifth base of a consensus pentapyrimidine element (C/T)CCTT (Shuman, 1991. Journal/J Biol Chem, 266: 1796-1803; Shuman and Prescott, 1990. Journal/J Biol Chem, 265: 17826-17836.) in the donor DNA molecule. This reaction is reversible. When the scissile bond is situated close to (within approximately 10 bp of) the 3' end of the DNA duplex, the downstream portion of the cleaved strand spontaneously dissociates, preventing reversal of the reaction and forming a stable covalent adduct. This covalent adduct is then purified. When the covalent adduct is mixed with an acceptor DNA molecule, the topoisomerase that is covalently bound to the donor molecule catalyzes the joining of the two DNA molecules. This joining requires that the 5' ends of the acceptor DNA are hydroxylated (not phosphorylated) and that the single-stranded overhangs of the donor and acceptor, if any, are compatible (i.e. complementary).

Topoisomerase-based cloning is in principle a powerful cloning technology, allowing the rapid cloning of any blunt or sticky-ended DNA fragment (Geng et al., 2006. Journal/Mol Biotechnol, 33: 23-28.). However the previously described methods require extensive preparation and processing steps to make a vector suitable for topoisomerase-based cloning. Vaccinia topoisomerase only cleaves one of the DNA strands of the donor molecule. For the donor to be ligated to the acceptor DNA molecule by vaccinia topoisomerase, however, both strands of the donor must be cleaved. This can be accomplished by ligating oligonucleotides containing the consensus pentapyrimidine element (C/T)CCTT to a DNA molecule that has been cleaved with a restriction endonuclease. The ligation mixture is then purified, re-cut and re-purified. Treatment of the DNA with purified topoisomerase (and additional oligonucleotides) produces a covalent adduct between the DNA and the topoisomerase. This adduct is then purified to produce the donor DNA (Heyman et al., 1999. Journal/Genome Res, 9: 383-392.)(see U.S. Pat. Nos. 5,766,891; 6,548,277; 6,653,106; 6,916,632 and 7,026,141).

The multiple processing and purification steps required to convert a vector into a topoisomerase-adduct donor molecule limit the ease with which topoisomerase-based cloning can be applied to new vectors. There is therefore a need in the art for a cloning method that allows simple cloning of any DNA molecule without the extensive preparation required by current methodologies. These and other unmet needs are provided by the presently claimed methods, compositions, and kits.

4. SUMMARY OF THE INVENTION

In certain aspects, provided herein are methods for cloning duplex DNA fragments that comprise preparing a single mixture of donor DNA, acceptor DNA and topoisomerase enzyme.

In another aspect, nucleic acid sequences are provided that can be incorporated into vector DNA sequences, thereby producing vectors that can ligate with an insert DNA when mixed with said insert DNA and topoisomerase enzyme.

Accordingly, in a first aspect, provided is a method for cloning a polynucleotide comprising combining into a mixture a first polynucleotide, wherein said first polynucleotide comprises a selectable marker, two topoisomerase recognition sequences, and two nicking agent recognition sequences, wherein each of said two topoisomerase recognition sequences is within 0-50 nucleotides of at least one of the nicking agent recognition sequences, with a sequence-specific topoisomerase and a second polynucleotide, wherein said second polynucleotide comprises a 5' hydroxyl on each end of the polynucleotide; and transforming the mixture into a host organism, thereby cloning the second polynucleotide.

In certain embodiments, said nicking agent recognition sequences are nicked by a sequence-specific single stranded nicking endonuclease. In certain embodiments, said single stranded nicking endonuclease is Nb.BsmI, Nt.BstNBI, Nb.BsrDI, Nt.BtsI or Nt.AlwI. In certain embodiments, said first polynucleotide has been contacted with a sequence-specific nicking agent prior to contact with said sequence-specific topoisomerase or said second polynucleotide. In certain embodiments, said first polynucleotide is contacted with a sequence-specific nicking agent contemporaneously or after contact with said sequence-specific topoisomerase or said second polynucleotide.

In certain embodiments, said sequence-specific topoisomerase is vaccinia topoisomerase I. In certain embodiments, said sequence-specific topoisomerase comprises an amino acid sequence identified as SEQ ID NO:9.

In certain embodiments, said second polynucleotide comprises a synthetic polynucleotide.

In certain embodiments, said first polynucleotide comprises a counter-selectable marker, wherein said counter-selectable marker is between said topoisomerase recognition sequences and wherein one of said topoisomerase recognition sequences is between said selectable marker and said counter-selectable marker. In certain embodiments, the counter-selectable marker is sacB, rpsL, tetAR, pheS, thyA, lacY, gata-1, ccdB, kid or barnase. In certain embodiments, the counter-selectable marker is ccdB.

In certain embodiments, said first polynucleotide comprises a double stranded break, wherein said double stranded break is between said topoisomerase recognition sequences and wherein one of said topoisomerase recognition sequences is between said selectable marker and said double stranded break. In certain embodiments, said first polynucleotide has been cleaved by an endonuclease to produce said double stranded break prior to said contacting of said first polynucleotide with said sequence-specific topoisomerase and said second polynucleotide.

In certain embodiments, said second polynucleotide has been prepared by PCR amplification. In certain embodiments, said host organism is E. coli.

In certain embodiments, said two topoisomerase recognition sequences independently comprise CAACATTTCCGT-GTCGCCCTTATTCCCTTTTTTGCGGCAT (SEQ ID NO 11), GCTCGGCCCTTCCGG (SEQ ID NO 12), AGGC-CCGCACCGATCGCCCTTCCCA (SEQ ID NO:13), CAAAATCCCTTAACG (SEQ ID NO:14), TGAAGATC-CTTTTTG (SEQ ID NO:15), ATTTTCTCCTTACGC (SEQ ID NO:16), or GTGTCGCCCTTATTC (SEQ ID NO:17). In certain embodiments, said two topoisomerase recognition sequences comprise GTGTCGCCCTTATTC (SEQ ID NO:17). In certain embodiments, said first polynucleotide further comprises an origin of replication.

In a second aspect, provided is a composition comprising a first polynucleotide, wherein said first polynucleotide comprises a selectable marker, two topoisomerase recognition sequences, and two nicking agent recognition sequences, wherein each of said two topoisomerase recognition sequences is within 0-50 nucleotides of at least one of the nicking agent recognition sequences and wherein each of said two nicking agent recognition sequences is nicked, a sequence-specific topoisomerase, and a second polynucleotide, wherein said second polynucleotide comprises a 5' hydroxyl on each end of the polynucleotide.

In certain embodiments, wherein the composition further comprises a sequence-specific nicking agent. In certain embodiments, said sequence-specific nicking agent is a single stranded nicking endonuclease. In certain embodiments, said single stranded nicking endonuclease is Nb.BsmI, Nt.BstNBI, Nb.BsrDI, Nt.BtsI or Nt.AlwI.

In certain embodiments, the composition further comprises a buffer. In certain embodiments, the buffer is selected such that one or more nicking agents are active in the buffer. In certain embodiments, the buffer is selected such that one or more topoisomerases are active in the buffer. In certain embodiments, the buffer is selected such that one or more nicking agents one or more topoisomerases are active in the buffer.

In certain embodiments, said sequence-specific topoisomerase is vaccinia topoisomerase I. In certain embodiments, said sequence specific topoisomerase comprises an amino acid sequence identified as SEQ ID NO:9.

In certain embodiments, said second polynucleotide comprises a synthetic polynucleotide.

In certain embodiments, said first polynucleotide comprises a counter-selectable marker, wherein said counter-selectable marker is between said topoisomerase recognition sequences and wherein one of said topoisomerase recognition sequences is between said selectable marker and said counter-selectable marker. In certain embodiments, the counter-selectable marker is sacB, rpsL, tetAR, pheS, thyA, lacY, gata-1, ccdB, kid or barnase. In certain embodiments, the counter-selectable marker is ccdB.

In certain embodiments, said first polynucleotide comprises a double stranded break, wherein said double stranded break is between said s topoisomerase recognition sequences and wherein one of said topoisomerase recognition sequences is between said selectable marker and said double stranded break.

In certain embodiments, said second polynucleotide has been prepared by PCR amplification.

In certain embodiments, said two topoisomerase recognition sequences independently comprise CAACATTTCCGTGTCGCCCTTATTCCCTTTTTTGCGGCAT (SEQ ID NO 11), GCTCGGCCCTTCCGG (SEQ ID NO 12), AGGCCCGCACCGATCGCCCTTCCCA (SEQ ID NO:13), CAAAATCCCTTAACG (SEQ ID NO:14), TGAAGATCCTTTTTG (SEQ ID NO:15), ATTTTCTCCTTACGC (SEQ ID NO:16), or GTGTCGCCCTTATTC (SEQ ID NO:17). In certain embodiments, said two topoisomerase recognition sequences comprise GTGTCGCCCTTATTC (SEQ ID NO:17). In certain embodiments, said first polynucleotide further comprises an origin of replication.

In a third aspect, provided is a kit for cloning a polynucleotide, comprising: a first polynucleotide, wherein said first polynucleotide comprises a selectable marker, two topoisomerase recognition sequences, two nicking agent recognition sequences, and a counter-selectable marker, a double-stranded break, or a endonuclease recognition sequence, wherein each of said two topoisomerase recognition sequences is within 0-50 nucleotides of at least one of the nicking agent recognition sequences, said counter-selectable marker, double-stranded break, or endonuclease recognition sequence is between said topoisomerase recognition sequences, and one of said topoisomerase recognition sequences is between said selectable marker and said counter-selectable marker, double-stranded break, or endonuclease recognition sequence, a sequence-specific topoisomerase; and instructions directing a user to combine the first polynucleotide, and the sequence-specific topoisomerase, wherein said second polynucleotide comprises a 5' hydroxyl on each end of the polynucleotide.

In certain embodiments, the first polynucleotide is nicked at each of the nicking agent recognition sequences. In certain embodiments, the kit further comprises a sequence-specific nicking agent. In certain embodiments, said sequence-specific nicking agent is a single stranded nicking endonuclease. In certain embodiments, said single stranded nicking endonuclease is Nb.BsmI, Nt.BstNBI, Nb.BsrDI, Nt.BtsI or Nt.AlwI. In certain embodiments, said sequence-specific topoisomerase is vaccinia topoisomerase I.

In certain embodiments, said sequence specific topoisomerase comprises an amino acid sequence identified as SEQ ID NO:9.

In certain embodiments, the counter-selectable marker is sacB, rpsL, tetAR, pheS, thyA, lacY, gata-1, ccdB, kid or barnase. In certain embodiments, the counter-selectable marker is ccdB.

In certain embodiments, said two topoisomerase recognition sequences independently comprise CAACATTTCCGTGTCGCCCTTATTCCCTTTTTTGCGGCAT (SEQ ID NO 11), GCTCGGCCCTTCCGG (SEQ ID NO 12), AGGCCCGCACCGATCGCCCTTCCCA (SEQ ID NO:13), CAAAATCCCTTAACG (SEQ ID NO:14), TGAAGATCCTTTTTG (SEQ ID NO:15), ATTTTCTCCTTACGC (SEQ ID NO:16), or GTGTCGCCCTTATTC (SEQ ID NO:17). In certain embodiments, said two topoisomerase recognition sequences comprise GTGTCGCCCTTATTC (SEQ ID NO:17). In certain embodiments, said first polynucleotide further comprises an origin of replication.

In a fourth aspect, provided is a method for making a vector for cloning a polynucleotide with a topoisomerase, comprising, introducing into a first polynucleotide, said first polynucleotide comprising a selectable marker, a second polynucleotide comprising two topoisomerase recognition sequences and two nicking agent recognition sequences, wherein each of said two topoisomerase recognition sequences is within 0-50 nucleotides of at least one of the nicking agent recognition sequences, wherein nicking at the two nicking agent recognition sequences and binding of a sequence-specific topoisomerase to the two topoisomerase recognition sequences releases a portion of the second polynucleotide.

In certain embodiments, said nicking agent recognition sequences are recognized by a sequence-specific single stranded nicking endonuclease. In certain embodiments, said single stranded nicking endonuclease is Nb.BsmI, Nt.BstNBI, Nb.BsrDI, Nt.BtsI or Nt.AlwI.

In certain embodiments, said sequence-specific topoisomerase is vaccinia topoisomerase I and the topoisomerase recognition sequences are recognized by vaccinia topoisomerase I. In certain embodiments, said sequence-specific topoisomerase comprises an amino acid sequence identified as SEQ ID NO:9.

In certain embodiments, release of said portion of said second polynucleotide results in a single-stranded overhang of between 1 and 50 nucleotides at one or both ends of said first polynucleotide. In certain embodiments, said single-stranded overhang(s) comprise 1, 2, 3, 4, 5, 6, 7, 8, 9, or 10 nucleotides.

In certain embodiments, said second polynucleotide comprises a counter-selectable marker, wherein said counter-selectable marker is between said topoisomerase recognition sequences and between said nicking agent recognition sequences. In certain embodiments, the counter-selectable marker is sacB, rpsL, tetAR, pheS, thyA, lacY, gata-1, ccdB, kid or barnase. In certain embodiments, the counter-selectable marker is ccdB.

In certain embodiments, said second polynucleotide comprises an endonuclease recognition sequence, wherein said endonuclease recognition sequence is between said topoisomerase recognition sequences and between said nicking agent recognition sequences.

In certain embodiments, said two topoisomerase recognition sequences independently comprise CAACATTTCCGTGTCGCCCTTATTCCCTTTTTTGCGGCAT (SEQ ID NO 11), GCTCGGCCCTTCCGG (SEQ ID NO 12), AGGCCCGCACCGATCGCCCTTCCCA (SEQ ID NO:13), CAAAATCCCTTAACG (SEQ ID NO:14), TGAAGATCCTTTTTG (SEQ ID NO:15), ATTTTCTCCTTACGC (SEQ ID NO:16), or GTGTCGCCCTTATTC (SEQ ID NO:17). In certain embodiments, said two topoisomerase recognition sequences comprise GTGTCGCCCTTATTC (SEQ ID NO:17). In certain embodiments, said first polynucleotide further comprises an origin of replication.

In yet another aspect, provided is a kit for making a vector for cloning a polynucleotide with a topoisomerase, comprising a second polynucleotide comprising two topoisomerase recognition sequences and two nicking agent recognition sequences, wherein each of said two topoisomerase recognition sequences is within 0-50 nucleotides of at least one of the nicking agent recognition sequences, wherein nicking at the two nicking agent recognition sequences and binding of a sequence-specific topoisomerase to the two topoisomerase recognition sequences releases a portion of the second polynucleotide, or two primers each comprising a sequence independently selected from the group consisting of 5'-CCCTTATTCGACTC-3' (SEQ ID NO:18), or 5'-CCCTTAGCTGACTC-3' (SEQ ID NO:19), and 5'-CCCTTATTCGATCC-3' (SEQ ID NO:20); and instructions directing introduction of said second polynucleotide into a first polynucleotide comprising a selectable marker or directing PCR amplification of a third polynucleotide with said two primers and introduction of said third polynucleotide into a fourth polynucleotide comprising a selectable marker.

In certain embodiments, said nicking agent recognition sequences are recognized by a sequence-specific single stranded nicking endonuclease. In certain embodiments, said single stranded nicking endonuclease is Nb.BsmI, Nt.BstNBI, Nb.BsrDI, Nt.BtsI or Nt.AlwI. In certain embodiments, said sequence-specific topoisomerase is vaccinia topoisomerase I and the topoisomerase recognition sequences are recognized by vaccinia topoisomerase I. In certain embodiments, said sequence-specific topoisomerase comprises an amino acid sequence identified as SEQ ID NO:9.

In certain embodiments, release of said portion of said second polynucleotide results in a single-stranded overhang of between 1 and 50 nucleotides at one or both ends of said first polynucleotide. In certain embodiments, said singlestranded overhang(s) comprise 1, 2, 3, 4, 5, 6, 7, 8, 9, or 10 nucleotides.

In certain embodiments, said second polynucleotide comprises a counter-selectable marker, wherein said counter-selectable marker is between said topoisomerase recognition sequences and between said nicking agent recognition sequences. In certain embodiments, the counter-selectable marker is sacB, rpsL, tetAR, pheS, thyA, lacY, gata-1, ccdB, kid or barnase. In certain embodiments, the counter-selectable marker is ccdB.

In certain embodiments, said second polynucleotide comprises an endonuclease recognition sequence, wherein said endonuclease recognition sequence is between said topoisomerase recognition sequences and between said nicking agent recognition sequences. In certain embodiments, said two topoisomerase recognition sequences independently comprise CAACATTTCCGTGTCGCCCTTATTCCCTTTTTTGCGGCAT (SEQ ID NO 11), GCTCGGCCCTTCCGG (SEQ ID NO 12), AGGCCCGCACCGATCGCCCTTCCCA (SEQ ID NO:13), CAAAATCCCTTAACG (SEQ ID NO:14), TGAAGATCCTT<u>TTTG</u> (SEQ ID NO:15), ATTTTCTCCTTACGC (SEQ ID NO:16), or GTGTCGCCCTTATTC (SEQ ID NO:17). In certain embodiments, said two topoisomerase recognition sequences comprise GTGTCGCCCTTATTC (SEQ ID NO:17).

In certain embodiments, said first polynucleotide or said fourth polynucleotide further comprises an origin of replication. In certain embodiments, said third polynucleotide comprises a selectable marker or an endonuclease recognition sequence.

5. BRIEF DESCRIPTION OF THE FIGURES

FIG. 1 presents a diagrammatic representation of a method for cleaving both strands of a DNA vector for use in topoisomerase cloning. In this Figure, the cleavage of the two strands are shown temporally separated, but the cleavage of the two strands may occur in either order or it may be performed simultaneously. The 5' and 3' vector sequences are joined, so that the entire vector forms a closed circle. Part A: the vector is cleaved by a nicking agent on the strand that is complementary to the topoisomerase cleavage sequence element. In this Figure, the topoisomerase cleavage sequence element is shown as the pentapyrimidine tract 5'-CCCTT-3', so the vector is cleaved on the strand containing the sequence 5'-AAGGG-3'. Here that cleavage is shown taking place immediately before the first A in the sequence 5'-AAGGG-3', and is indicated with vertical black lines. The cleavage is preferably performed with an agent that leaves a 5'-phosphate. Part B: topoisomerase cleaves the DNA vector at the topoisomerase cleavage sequence element, in this case by forming an adduct with the second T of the sequence 5'-CCCTT-3'. Part C: the result is the formation of a bluntended vector that has a topoisomerase adduct on each 3' end, with the release of the DNA sequences that were originally contained between the two topoisomerase cleavage sequence elements.

Figure 2:
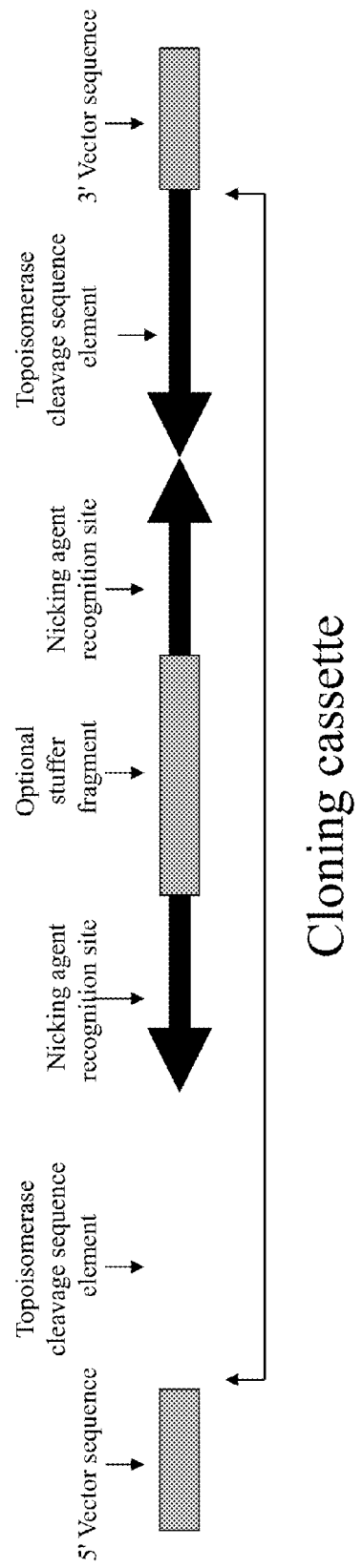

FIG. 2 shows a schematic representation of a DNA vector for 1-step topoisomerase cloning. The cloning cassette comprises two topoisomerase cleavage sequence elements, inverted with respect to one another. Between the two topoisomerase cleavage sequence elements are two sites recognized by one or more DNA nicking agents. Optionally between the two nicking agent recognition sites are additional DNA sequences (a "stuffer" fragment). The 5' and 3' vector sequences are joined, so that the entire vector forms a closed circle.

Figure 3:
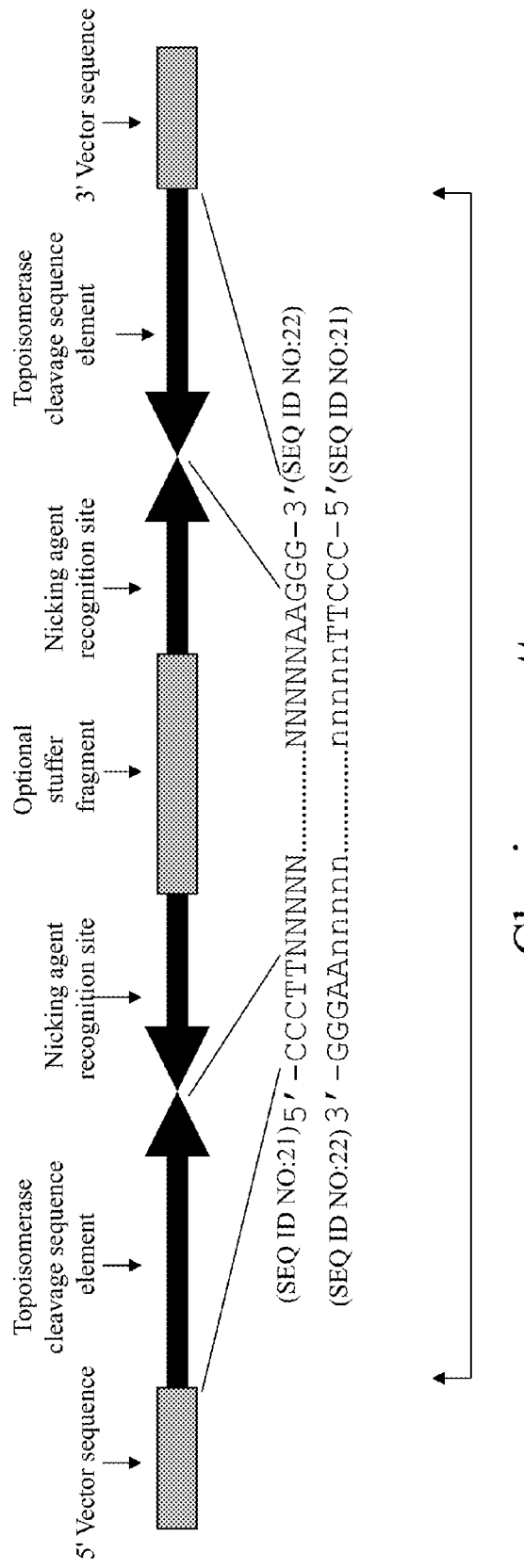

FIG. 3 shows one possible embodiment of the DNA vector from FIG. 2, in which the topoisomerase cleavage sequence elements are defined as the pentapyrimidine tract 5'-CCCTT-3' (Shuman, 1991. Journal/J Biol Chem, 266: 1796-1803; Shuman and Prescott, 1990. Journal/J Biol Chem, 265: 17826-17836.). The 5' and 3' vector sequences are joined, so that the entire vector forms a closed circle. In this Figure, 13 represents any nucleotide, and n represents its complementary base.

Figure 4:
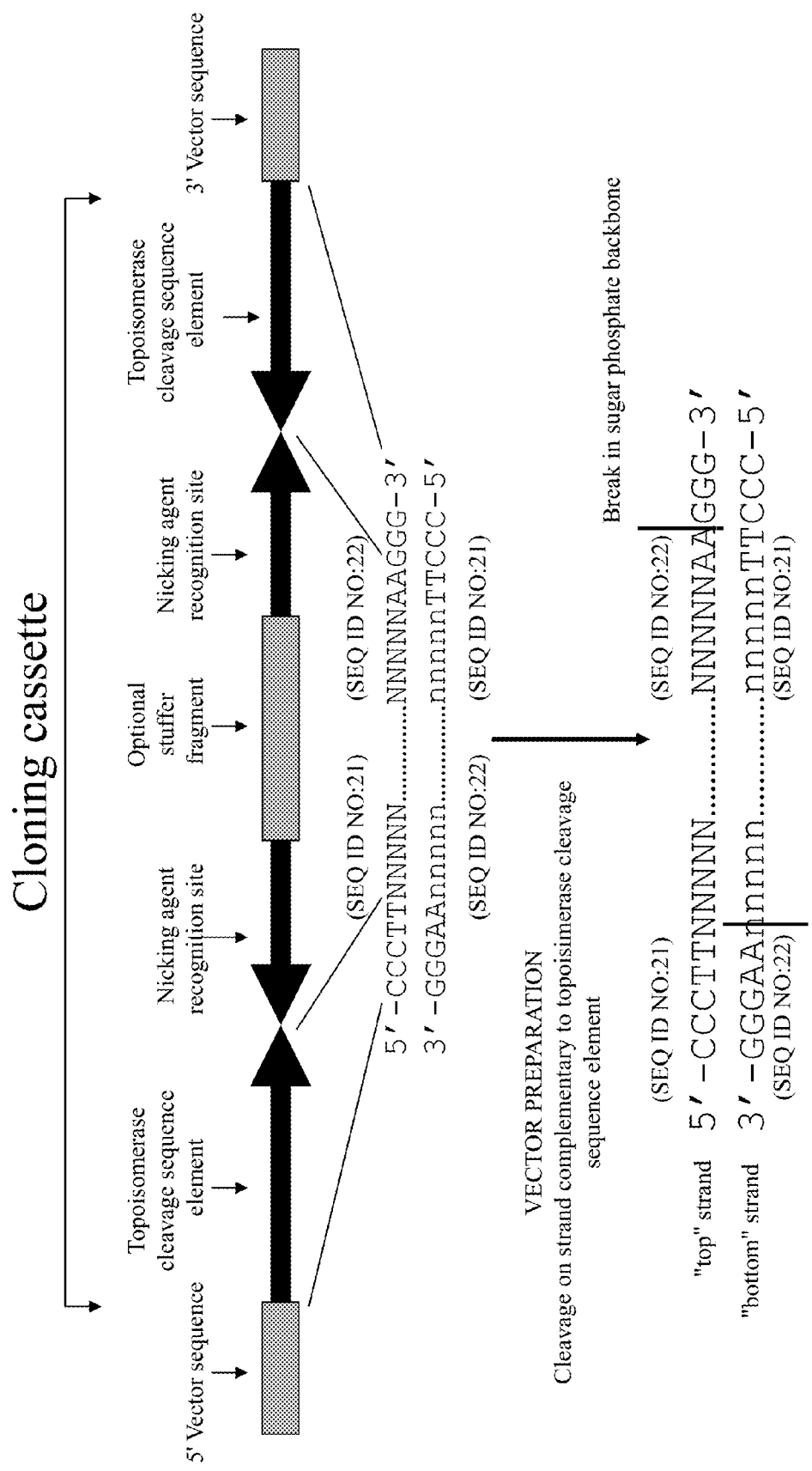

FIG. 4 shows one possible method of preparing the vector shown in FIG. 3. In this method sequences at the nicking agent recognition sites direct a nicking agent to cleave one strand of the sugar phosphate backbone of the DNA. The cleavage is directed to the DNA strand complementary to the strand containing the topoisomerase cleavage sequence elements. In the example shown here, cleavage is exactly opposite the phosphodiester bond that will be cleaved upon addition of topoisomerase (i.e., immediately before the first A in the sequence 5'-AAGGG-3'). The 5' and 3' vector sequences are joined, so that the entire vector forms a closed circle. In this Figure, 13 represents any nucleotide, and n represents its complementary base.

Figure 5:
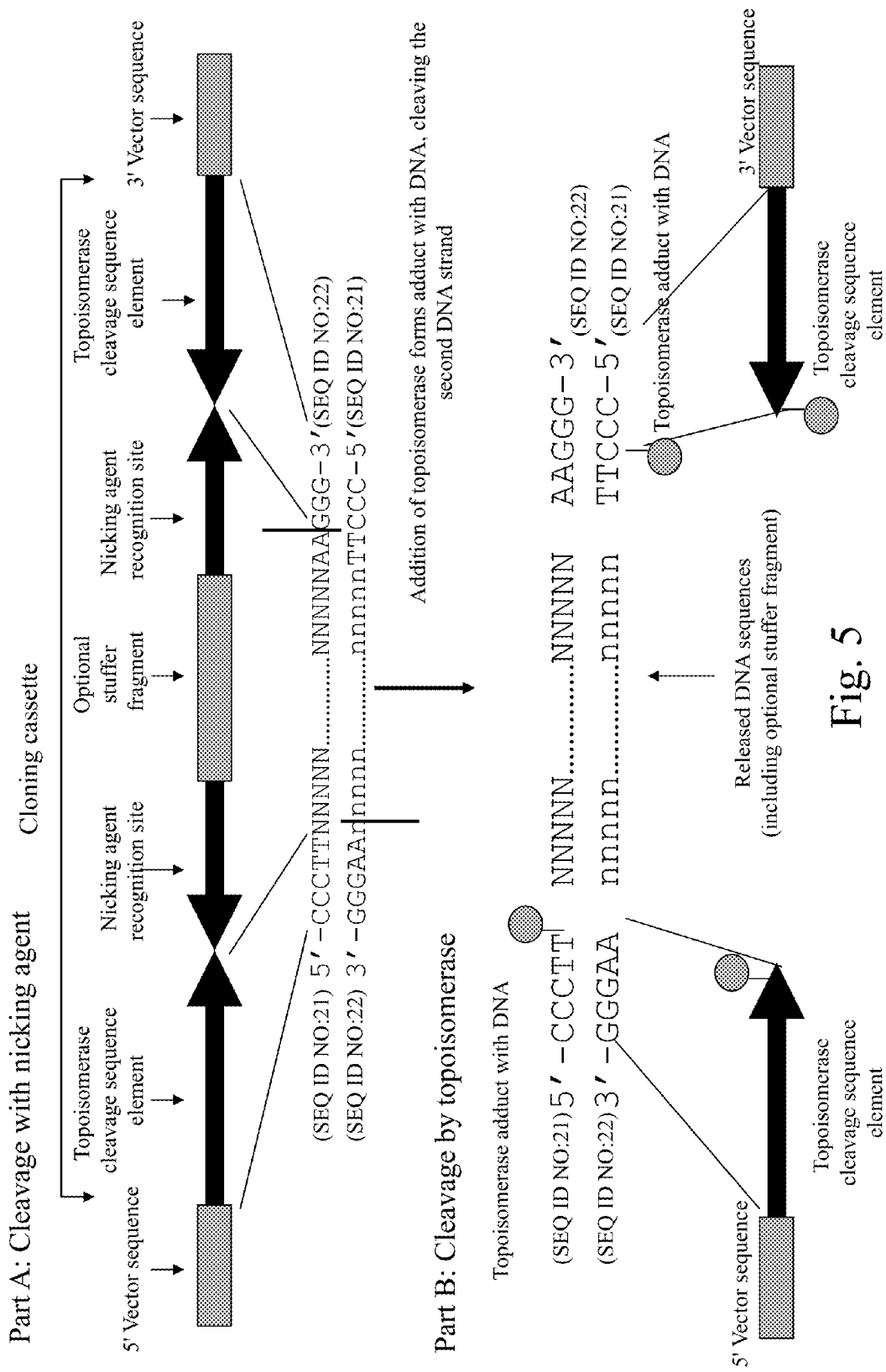

FIG. 5 shows the effect of treating a vector containing a cloning cassette like that shown in FIG. 4, with both a nicking agent and topoisomerase. In this Figure, the cleavage of the two strands are shown temporally separated, but the cleavage of the two strands may occur in either order or it may be performed simultaneously. Part A: the vector is cleaved on one strand by the nicking agent, as shown in FIG. 4. Part B: topoisomerase cleaves the DNA vector at the topoisomerase cleavage sequence element, in this case on the second T of the pentapyrimidine tract 5'-CCCTT-3'. The result is the formation of a vector that has a topoisomerase adduct on each 3' end, with the release of the DNA sequences that were originally contained between the two topoisomerase cleavage sequence elements. The 5' and 3' vector sequences are joined, so that the entire vector forms a closed circle. In this Figure, 13 represents any nucleotide, and n represents its complementary base.

FIG. 6 shows an equilibrium reaction that results from mixing vector DNA nicked by a nicking agent with topoisomerase (the products shown in FIG. 5, part B) and a polynucleotide insert to be cloned. Part A: the actions of nicking agent and topoisomerase cleave the vector DNA at the topoisomerase cleavage sequence elements, producing covalent DNA-topoisomerase adducts and releasing DNA sequences from within the vector. Part B: topoisomerase bound to the vector DNA catalyzes the joining of the vector DNA with either the DNA that was released from the vector when it was cleaved by topoisomerase, or with the polynucleotide insert to be cloned. The 5' and 3' vector sequences are joined, so that the entire vector forms a closed circle. The cleavage of the two strands may occur in either order or it may be performed simultaneously.

Figure 7:
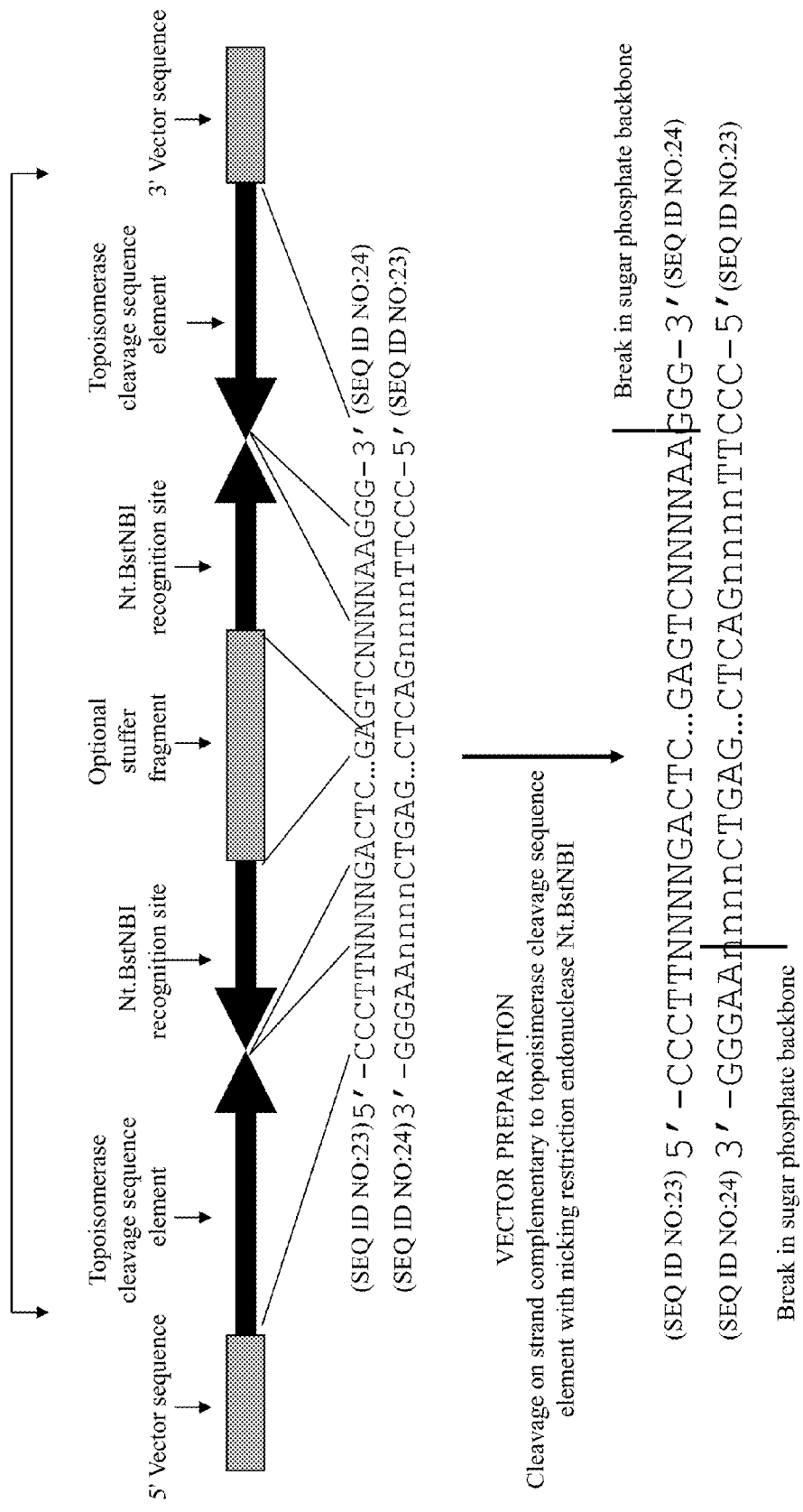

FIG. 7 shows one embodiment of the method of preparing the vector shown in FIG. 4. In this embodiment the nicking agent is a nicking restriction endonuclease Nt.BstNBI. The 5 base recognition site for Nt.BstNBI (5'-GAGTC-3') directs the enzyme to cleave one strand of the DNA helix, 4 bases after the final base (C) of the recognition sequence. When positioned as shown in the Figure, cleavage is directed to the DNA strand complementary to the strand containing the topoisomerase cleavage sequence elements. In the example shown here, cleavage is exactly opposite the phosphodiester bond that will be cleaved upon addition of topoisomerase (i.e., immediately before the first A in the sequence 5'-AAGGG-3'). The 5' and 3' vector sequences are joined, so that the entire vector forms a closed circle. In this Figure, 13 represents any nucleotide, and n represents its complementary base.

Figure 8:
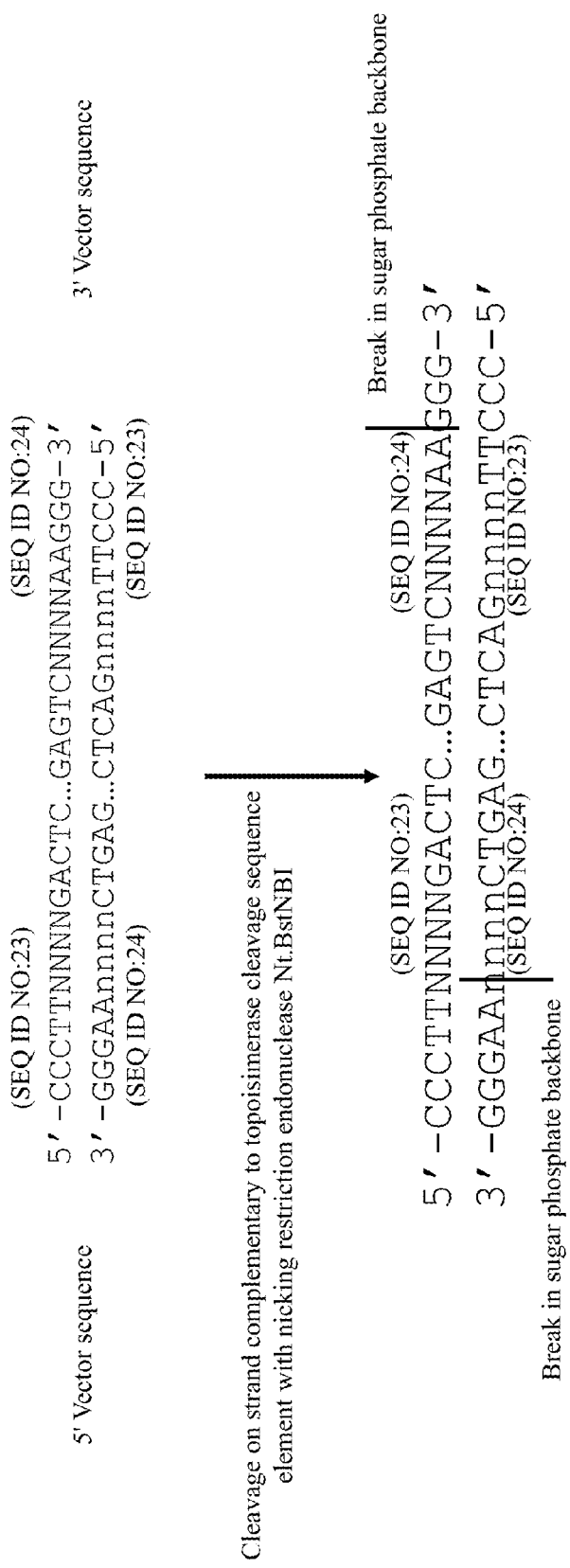

FIG. 8 shows one exemplary method for the cleavage of the vector DNA in the strand that is complementary to the topoisomerase cleavage sequence element. In this method, a nicking endonuclease recognition site is placed on the complementary strand to the topoisomerase cleavage sequence element and in the opposite orientation. In this Figure, the site is 5'-GAGTC-3': the recognition site for the nicking endonuclease Nt.BstNBI. By positioning the site four nucleotides to the 5' of the sequence 5'-AAGGG-3', Nt.BstNBI is directed to make a break in the sugar phosphate DNA backbone immediately before the first A in the sequence 5'-AAGGG-3'. The 5' and 3' vector sequences are joined, so that the entire vector forms a closed circle.

Figure 9:
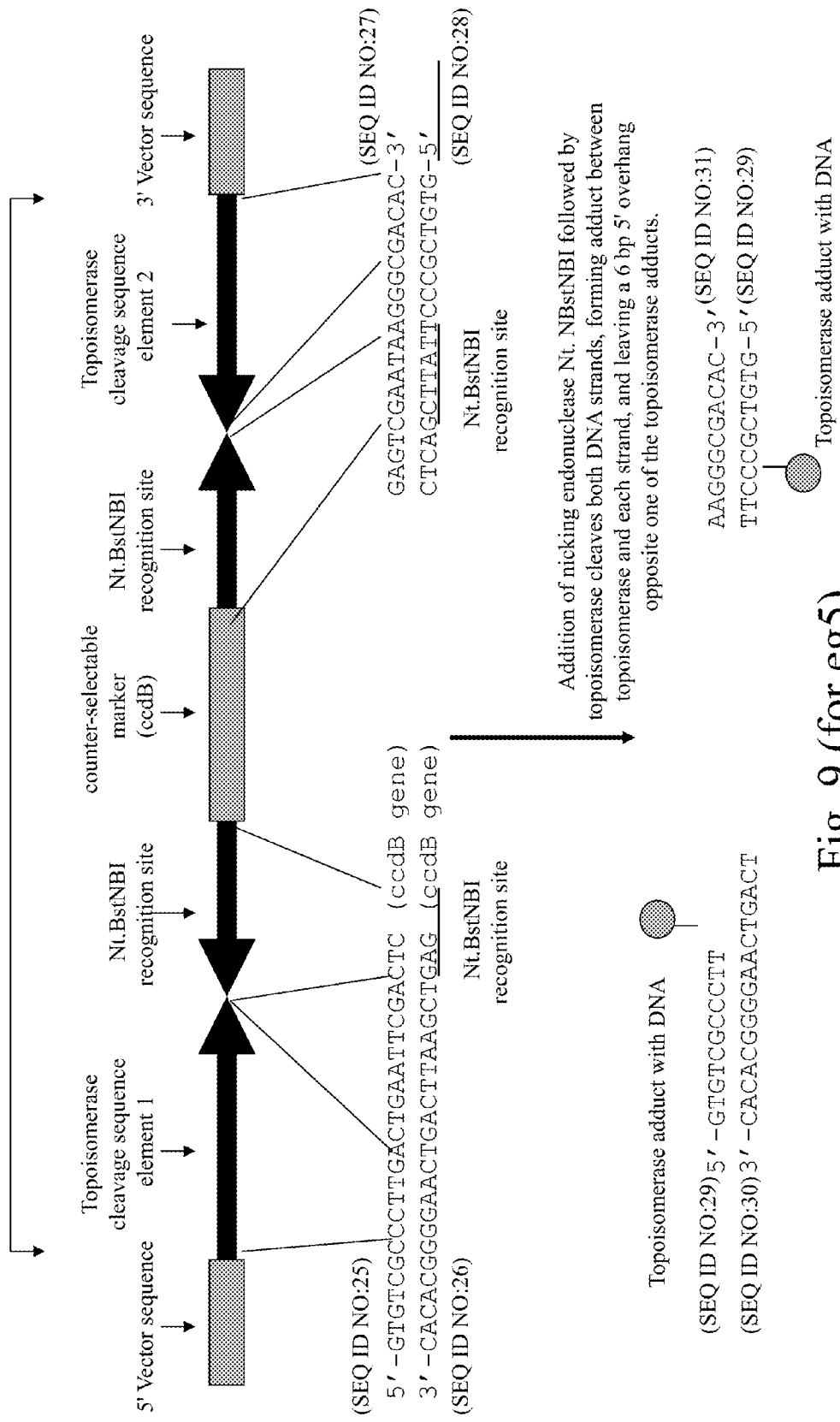

FIG. 9 shows a schematic representation of one embodiment of the DNA vector for 1-step topoisomerase cloning shown in FIG. 2. This embodiment was used in the procedure described in Example 5. The cloning cassette comprises two topoisomerase cleavage sequence elements (5'-CCCTT-3'), inverted with respect to one another. There is a 6 base sequence (5'-GTGTCG-3') immediately 5' of each topoisomerase cleavage sequence element, derived from a high affinity topoisomerase site from pUC19 (Shuman and Prescott, 1990. Journal/J Biol Chem, 265: 17826-17836.). Ten bases to the 3' of topoisomerase cleavage sequence element 1, and four bases to the 3' of topoisomerase cleavage sequence element 2, in an inverted orientation, are sequences recognized by the nicking restriction endonuclease Nt.BstNBI (5'-GAGTC-3'). The restriction endonuclease Nt.BstNBI will nick immediately 5' of the sequence 5'-AAGGG-3' in topoisomerase cleavage sequence element 2, that is opposite the phosphodiester bond that will be cleaved upon addition of topoisomerase. The restriction endonuclease Nt.BstNBI will nick 6 bases 5' of the sequence 5'-AAGGG-3' in topoisomerase cleavage sequence element 1, resulting in a 6 base overhang upon addition of topoisomerase. Between the two Nt.BstNBI sites is a gene encoding the counter-selectable marker ccdB. The 5' and 3' vector sequences are joined, so that the entire vector forms a closed circle. At the bottom of the Figure, the two ends of the vector are shown after nicking with Nt.BstNBI and addition of vaccinia topoisomerase I.

Figure 10:
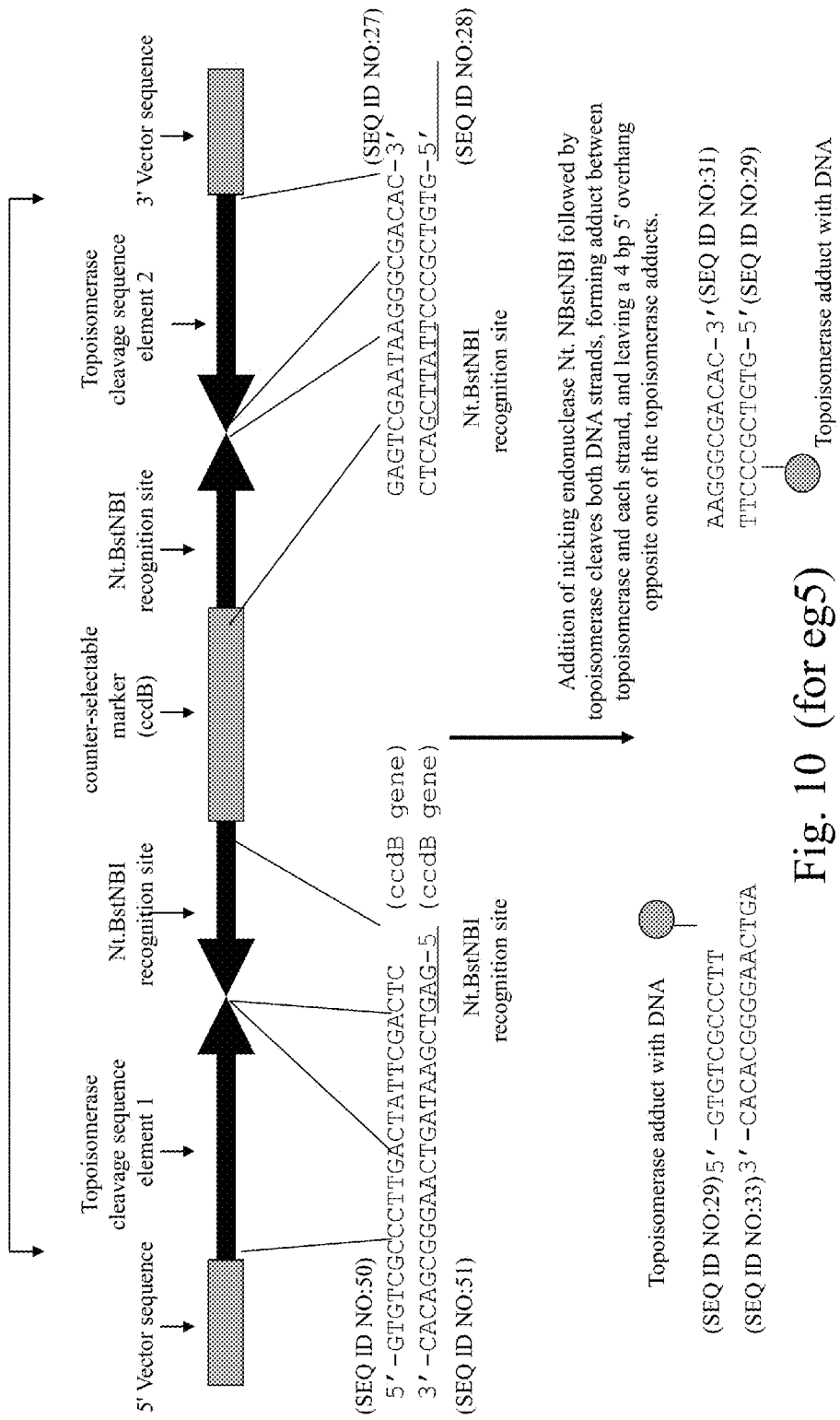

FIG. 10 shows a schematic representation of one embodiment of the DNA vector for 1-step topoisomerase cloning shown in FIG. 2. This embodiment was used in the procedure described in Example 5. The cloning cassette comprises two topoisomerase cleavage sequence elements (5'-CCCTT-3'), inverted with respect to one another. There is a 6 base sequence (5'-GTGTCG-3') immediately 5' of each topoisomerase cleavage sequence element, derived from a high affinity topoisomerase site from pUC19 (Shuman and Prescott, 1990. Journal/J Biol Chem, 265: 17826-17836.). Eight bases to the 3' of topoisomerase cleavage sequence element 1, and four bases to the 3' of topoisomerase cleavage sequence element 2, in an inverted orientation, are sequences recognized by the nicking restriction endonuclease Nt.BstNBI (5'-GAGTC-3'). The restriction endonuclease Nt.BstNBI will nick immediately 5' of the sequence 5'-AAGGG-3' in topoisomerase cleavage sequence element 2, that is opposite the phosphodiester bond that will be cleaved upon addition of topoisomerase. The restriction endonuclease Nt.BstNBI will nick 4 bases 5' of the sequence 5'-AAGGG-3' in topoisomerase cleavage sequence element 1, resulting in a 4 base overhang upon addition of topoisomerase. Between the two Nt.BstNBI sites is a gene encoding the counter-selectable marker ccdB. The 5' and 3' vector sequences are joined, so that the entire vector forms a closed circle. At the bottom of the Figure, the two ends of the vector are shown after nicking with Nt.BstNBI and addition of vaccinia topoisomerase I.

Figure 11:
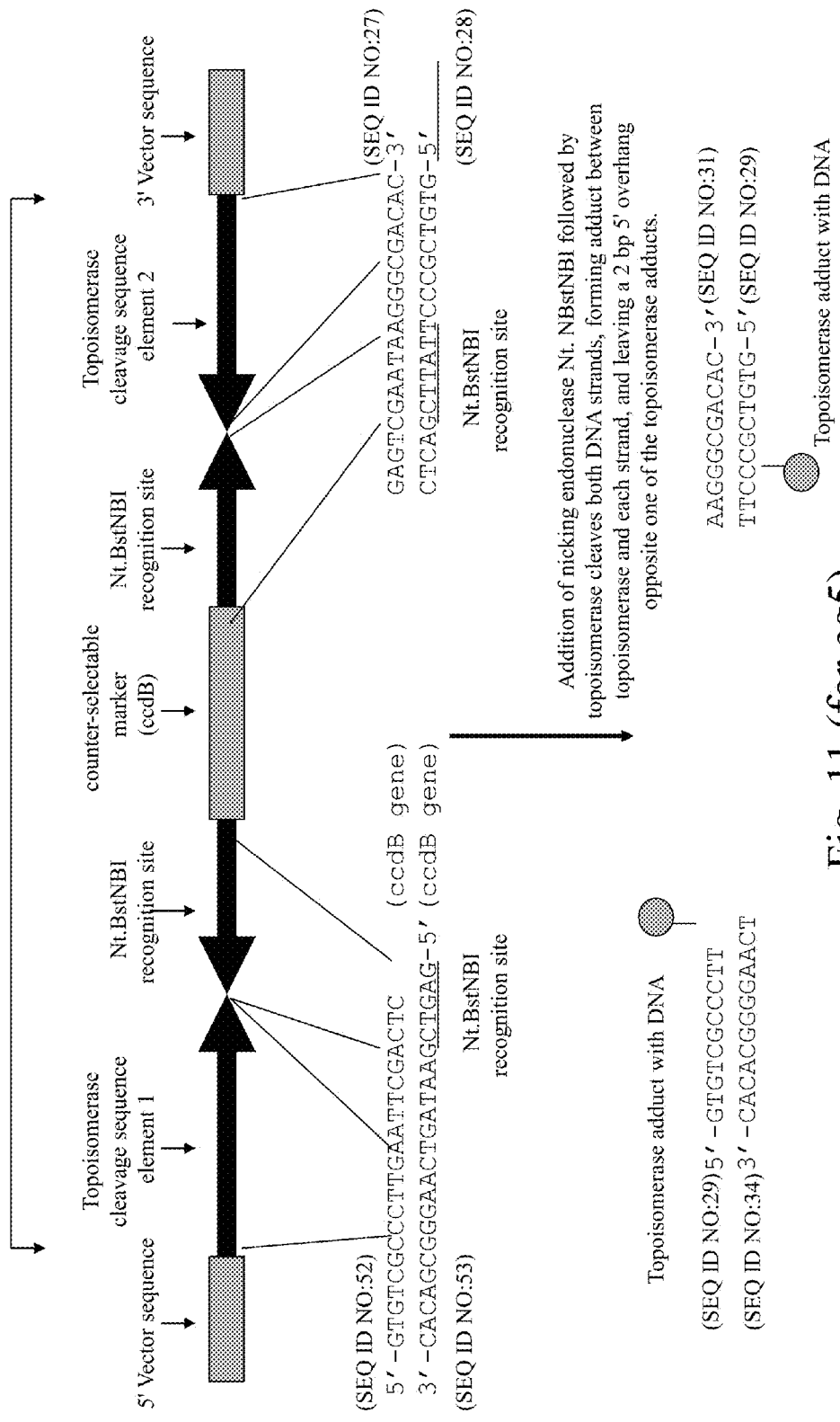

FIG. 11 shows a schematic representation of one embodiment of the DNA vector for 1-step topoisomerase cloning shown in FIG. 2. This embodiment was used in the procedure described in Example 5. The cloning cassette comprises two topoisomerase cleavage sequence elements (5'-CCCTT-3'), inverted with respect to one another. There is a 6 base sequence (5'-GTGTCG-3') immediately 5' of each topoisomerase cleavage sequence element, derived from a high affinity topoisomerase site from pUC19 (Shuman and Prescott, 1990. Journal/J Biol Chem, 265: 17826-17836.). Six bases to the 3' of topoisomerase cleavage sequence element 1, and four bases to the 3' of topoisomerase cleavage sequence element 2, in an inverted orientation, are sequences recognized by the nicking restriction endonuclease Nt.BstNBI (5'-GAGTC-3'). The restriction endonuclease Nt.BstNBI will nick immediately 5' of the sequence 5'-AAGGG-3' in topoisomerase cleavage sequence element 2, that is opposite the phosphodiester bond that will be cleaved upon addition of topoisomerase. The restriction endonuclease Nt.BstNBI will nick 2 bases 5' of the sequence 5'-AAGGG-3' in topoisomerase cleavage sequence element 1, resulting in a 2 base overhang upon addition of topoisomerase. Between the two Nt.BstNBI sites is a gene encoding the counter-selectable marker ccdB. The 5' and 3' vector sequences are joined, so that the entire vector forms a closed circle. At the bottom of the Figure, the two ends of the vector are shown after nicking with Nt.BstNBI and addition of vaccinia topoisomerase I.

Figure 12:
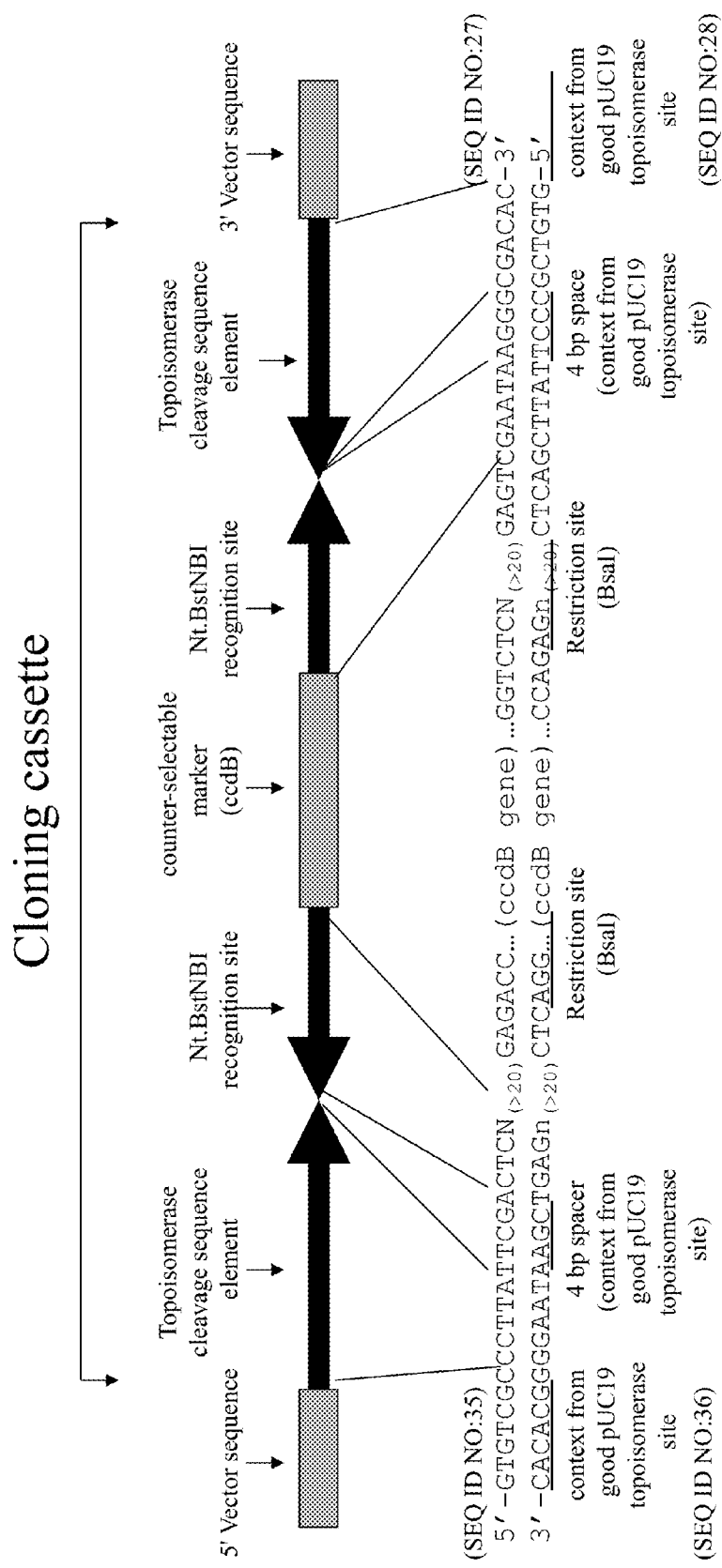

FIG. 12 shows a schematic representation of one embodiment of the DNA vector for 1-step topoisomerase cloning shown in FIG. 2. This embodiment was used in the procedure described in Example 2. The cloning cassette comprises two topoisomerase cleavage sequence elements (5'-CCCTT-3'), inverted with respect to one another. There is a 6 base sequence (5'-GTGTCG-3') immediately 5' of each topoisomerase cleavage sequence element, and a 4 bp spacer sequence (5'-ATTC-3') immediately 3' of each topoisomerase cleavage sequence element. These sequences adjacent to the topoisomerase cleavage sequence element are derived from a high affinity topoisomerase site from pUC19 (Shuman and Prescott, 1990. Journal/J Biol Chem, 265: 17826-17836.). Four bases to the 3' of each topoisomerase cleavage sequence element, in an inverted orientation are sequences recognized by the nicking restriction endonuclease Nt.BstNBI (5'-GAGTC-3'). The presence of the 4 bp spacer ensures that the restriction endonuclease Nt.BstNBI will nick immediately 5' of the sequence 5'-AAGGG-3', that is opposite the phosphodiester bond that will be cleaved upon addition of topoisomerase. Between the two Nt.BstNBI sites is a gene encoding the counter-selectable marker ccdB. In this embodiment the ccdB gene is flanked by two BsaI restriction sites, each of which is at least 20 bp from the nearby Nt.BstNBI site. The 5' and 3' vector sequences are joined, so that the entire vector forms a closed circle.

Figure 13:
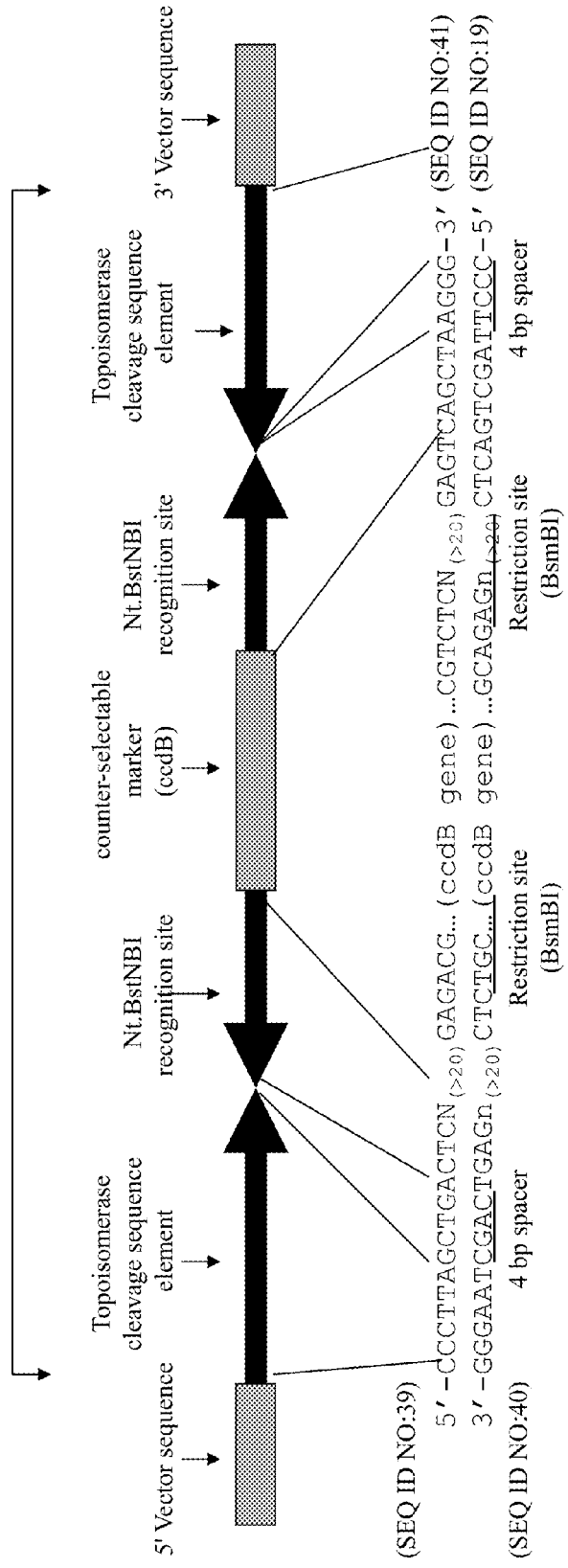

FIG. 13 shows a schematic representation of one embodiment of the DNA vector for 1-step topoisomerase cloning shown in FIG. 2. This embodiment was used in the procedure described in Example 1. The cloning cassette comprises two topoisomerase cleavage sequence elements (5'-CCCTT-3'), inverted with respect to one another. There is a 4 bp spacer sequence (5'-AGCT-3') immediately 3' of each topoisomerase cleavage sequence element. Four bases to the 3' of each topoisomerase cleavage sequence element, in an inverted orientation are sequences recognized by the nicking restriction endonuclease Nt.BstNBI (5'-GAGTC-3'). The presence of the 4 bp spacer ensures that the restriction endonuclease Nt.BstNBI will nick immediately 5' of the sequence 5'-AAGGG-3', that is opposite the phosphodiester bond that will be cleaved upon addition of topoisomerase. Between the two Nt.BstNBI sites is a gene encoding the counter-selectable marker ccdB. In this embodiment the ccdB gene is flanked by two BsmBI restriction sites, each of which is at least 20 bp from the nearby Nt.BstNBI site. The 5' and 3' vector sequences are joined, so that the entire vector forms a closed circle.

Figure 14:
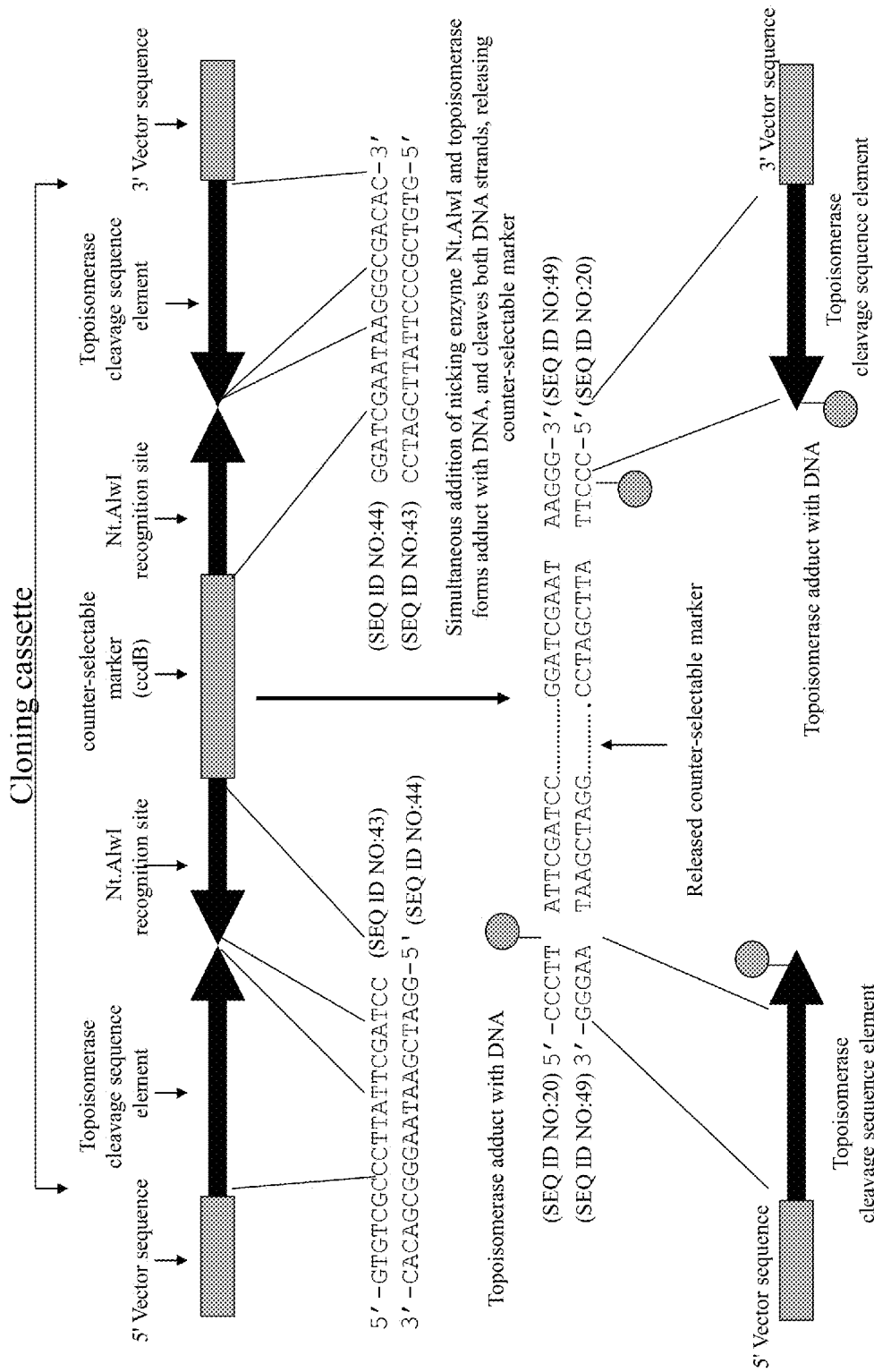

FIG. 14 shows a schematic representation of one embodiment of the DNA vector for 1-step topoisomerase cloning shown in FIG. 2. This embodiment was used in the procedure described in Examples 7 and 8. The cloning cassette comprises two topoisomerase cleavage sequence elements (5'-CCCTT-3'), inverted with respect to one another. There is a 6 base sequence (5'-GTGTCG-3') immediately 5' of each topoisomerase cleavage sequence element, and a 4 bp spacer sequence (5'-ATTC-3') immediately 3' of each topoisomerase cleavage sequence element. These sequences adjacent to the topoisomerase cleavage sequence element are derived from a high affinity topoisomerase site from pUC19 (Shuman and Prescott, 1990. Journal/J Biol Chem, 265: 17826-17836.). Four bases to the 3' of each topoisomerase cleavage sequence element, in an inverted orientation are sequences recognized by the nicking endonuclease Nt.AlwI (5'-GGATC-3'). The presence of the 4 bp spacer ensures that the nicking endonuclease Nt.AlwI will nick immediately 5' of the sequence 5'-AAGGG-3', that is opposite the phosphodiester bond that will be cleaved by vaccinia topoisomerase I. Between the two Nt.AlwI sites is a gene encoding the counter-selectable marker ccdB. The 5' and 3' vector sequences are joined, so that the entire vector forms a closed circle. Simultaneous addition of nicking endonuclease Nt.AlwI and vaccinia topoisomerase I results in the cleavage of both DNA strands, and formation of topoisomerase adducts at each 3' end of the vector DNA with the release of the sequences encoding the ccdB counter-selectable marker that were originally contained between the two topoisomerase cleavage sequence elements. The 5' and 3' vector sequences are joined, so that the entire vector forms a closed circle.

Figure 15:
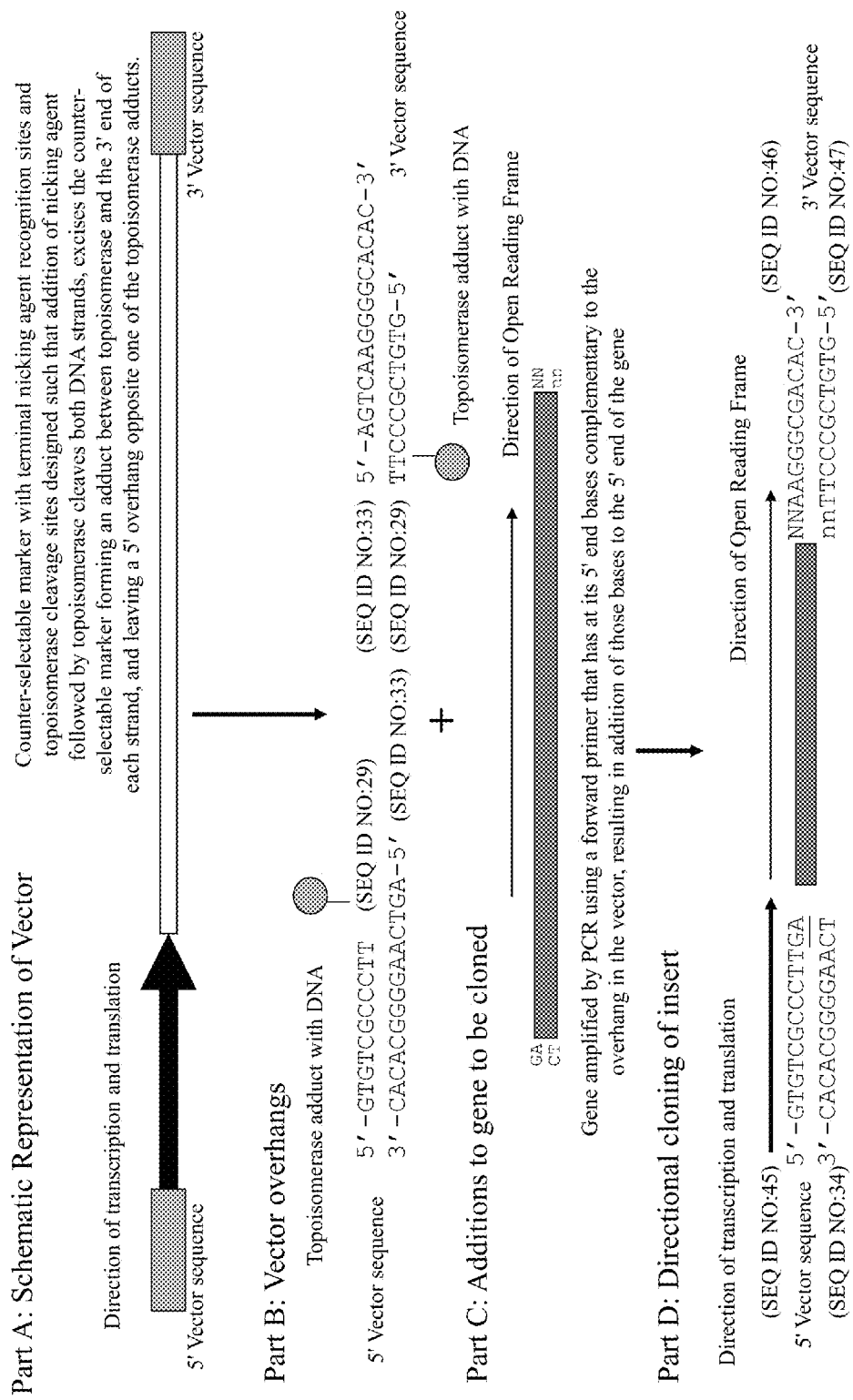

FIG. 15 shows a flow chart representing of one embodiment for directional 1-step topoisomerase cloning for protein expression. Part A: in this embodiment DNA containing an open reading frame (the "gene") is to be cloned into a vector that contains sequence elements that control transcription. Since elements in the vector determine the direction of transcription, the gene will only be expressed if it is cloned into the vector so that the open reading frame is in the same direction as the direction of transcription. This can be achieved by designing a cloning cassette consisting of a counter-selectable marker with terminal nicking agent recognition sites and topoisomerase cleavage sites placed such that addition of nicking agent and topoisomerase cleaves both DNA strands, excises the counter-selectable marker forming an adduct between topoisomerase and the 3' end of each strand, and leaving a 5' overhang opposite one of the topoisomerase adducts (Part B). Part C: the gene is amplified using a forward primer that has at its 5' end bases complementary to the overhang in the vector, resulting in addition of those bases to the 5' end of the gene. Part D: topoisomerase then inserts the gene in a specific orientation, with the end of the gene that has the complementary bases at the overhang end of the vector.

Figure 16:
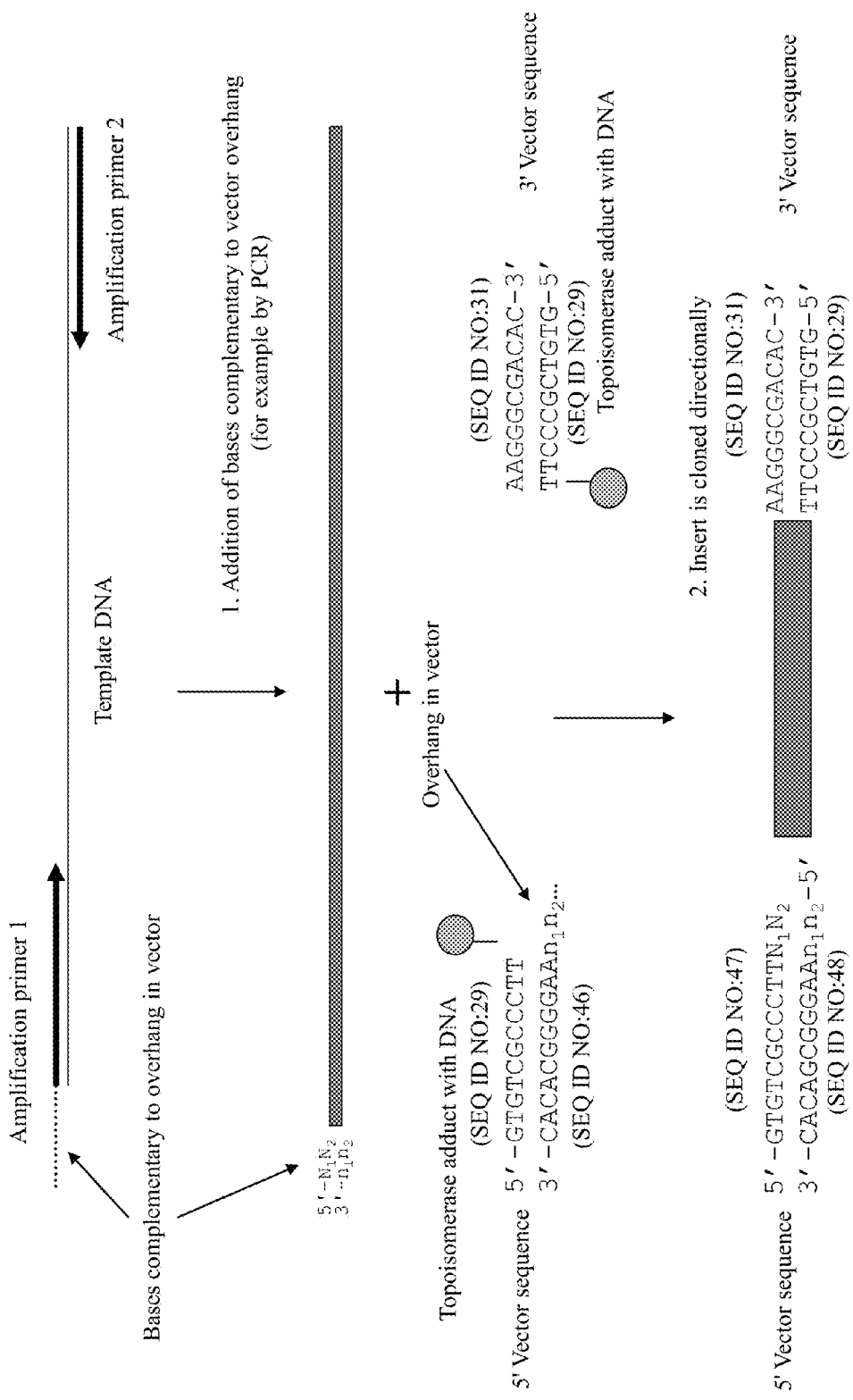

FIG. 16 shows a flow chart representing of one embodiment for directional 1-step topoisomerase cloning for protein expression. In this embodiment, an insert DNA is to be cloned into a vector in a specific orientation. This can be achieved by designing a cloning cassette with terminal nicking agent recognition sites and topoisomerase cleavage sites placed such that addition of nicking agent and topoisomerase cleaves both DNA strands, forming an adduct between topoisomerase and the 3' end of each strand, and leaving a 5' overhang opposite one of the topoisomerase adducts (shown here as 5'-$n_2 n_1$-3'). The insert is amplified using one primer that has at its 5' end bases complementary to the overhang in the vector, resulting in addition of those bases to the 5' end of the gene (shown here as 5'-$N_1 N_2$-3'). Topoisomerase then inserts the gene in a specific orientation, with the end of the gene that has the complementary bases at the overhang end of the vector.

6. DETAILED DESCRIPTION OF THE INVENTION

At the outset of this detailed description, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2nd ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used herein. Although any methods and materials similar or equivalent to those described herein can be used in the practice or testing, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

6.1 DEFINITIONS

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids ("PNAs")) and polymorpholino (commercially available from, for example, the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

Where the polynucleotides are to be used to express encoded proteins, nucleotides that can perform that function or which can be modified (e.g., reverse transcribed) to perform that function can be used. Where the polynucleotides are to be used in a scheme that requires that a complementary strand be formed to a given polynucleotide, nucleotides can be used which permit such formation.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxypyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610 to Collins et al. Other normatural base pairs may be synthesized by the method described in Piccirilli et al. (1990) Nature 343:33-37 for the synthesis of 2,6-diaminopyrimidine and its complement (1-methylpyrazolo-[4,3] pyrimidine-5,7-(4H,6H)-dione. Other such modified nucleotidic units which form unique base pairs are known, such as those described in Leach et al. (1992) J. Am. Chem. Soc. 114:3675-3683 and Switzer et al., supra.

The phrase "DNA sequence" refers to a contiguous deoxyribonucleic acid sequence. The sequence can be either single stranded or double stranded. The sequence can be an oligonucleotide of 2 to 20 nucleotides in length to a full length genomic sequence of thousands or hundreds of thousands of base pairs.

"Amino acids" or "amino acid residues" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "expression system" refers to any in vivo or in vitro biological system that is used to produce one or more protein encoded by a polynucleotide. A "heterologous expression system" is a system in which a gene is expressed in an organism or cell type other than that in which it is naturally expressed.

The term "vector" or "DNA vector" or "polynucleotide vector" refers to a polynucleotide sequence that can be propagated in a host cell. Vectors can be joined to a second DNA segment (the "insert"), thereby allowing the second DNA segment to be propagated in the host cell. Joining of the insert DNA with the vector DNA is often referred to as "cloning" the insert DNA. Generally, a vector can comprise an origin of replication and a selectable marker.

The term "stuffer" or "stuffer fragment" refers to a polynucleotide sequence that is present in a polynucleotide vector, but is removed prior to joining the vector with an insert.

The terms "topoisomerase cleavage sequence element" and "topoisomerase recognition sequence" are used interchangeably and refer to a sequence element that is recognized by a sequence-specific topoisomerase. A sequence-specific topoisomerase will form a covalent adduct with the 3' phosphate of a base in the topoisomerase cleavage sequence element.

The term "topoisomerase cleavage sequence element complementary strand" refers to the DNA strand that is complementary to the topoisomerase cleavage sequence element. Since both strands of a DNA sequence may contain topoisomerase cleavage sequence elements, the complementary strand refers to the strand that is complementary in the local region of the topoisomerase cleavage sequence element.

The term "cleavage agent" or "DNA cleavage agent" refers to a protein, chemical, nucleic acid or other compound or mixture of compounds that cleaves one or both strands of a DNA molecule. Restriction endonucleases and nicking endonucleases are examples of cleavage agents.

The term "nicking agent" or "DNA nicking agent" refers to a protein, chemical, nucleic acid or other compound or mixture of compounds that cleaves one strand of a DNA molecule. Nicking endonucleases are examples of nicking agents.

The term "cleavage agent recognition site" refers to a specific DNA sequence that is recognized by a cleavage agent. A restriction endonuclease site is an example of a cleavage agent recognition site.

The terms "nicking agent recognition site" and "nicking agent recognition sequence" are used interchangeably and refer to a specific DNA sequence that is recognized by a nicking agent. A nicking endonuclease site is an example of a cleavage agent recognition site.

The term "selectable marker" or "marker" refers to a DNA sequence that confers a selective advantage upon a host cell. Antibiotic resistance genes and genes that encode enzymes involved in the synthesis of essential molecules are examples of selectable markers. Selectable markers often confer their selective advantage in specific contexts. For example an antibiotic resistance gene will confer a selective advantage to a host growing in the presence of the antibiotic.

The term "counter-selectable marker" refers to a DNA sequence that confers a selective disadvantage upon a host cell. Examples of counter-selectable markers include sacB, rpsL, tetAR, pheS, thyA, lacY, gata-1, ccdB, kid and barnase (Bernard, 1995. Journal/Gene, 162: 159-160; Bernard et al., 1994. Journal/Gene, 148: 71-74; Gabant et al., 1997. Journal/Biotechniques, 23: 938-941; Gabant et al., 1998. Journal/Gene, 207: 87-92; Gabant et al., 2000. Journal/Biotechniques, 28: 784-788; Galvao and de Lorenzo, 2005. Journal/Appl Environ Microbiol, 71: 883-892; Hartzog et al., 2005. Journal/Yeast, 22: 789-798; Knipfer et al., 1997. Journal/Plasmid, 37: 129-140; Reyrat et al., 1998. Journal/Infect Immun, 66: 4011-4017; Soderholm et al., 2001. Journal/Biotechniques, 31: 306-310, 312; Tamura et al., 2005. Journal/Appl Environ Microbiol, 71: 587-590; Yazynin et al., 1999. Journal/FEBS Lett, 452: 351-354.). Counter-selectable markers often confer their selective disadvantage in specific contexts. For example they may confer sensitivity to compounds that can be added to the environment of the host cell, or they may kill a host with one genotype but not kill a host with a different genotype. Conditions which do not confer a selective disadvantage upon a cell carrying a counter-selectable marker are described as "permissive". Conditions which do confer a selective disadvantage upon a cell carrying a counter-selectable marker are described as "restrictive".

6.2 METHODS FOR USING TOPOISOMERASE TO CLONE DNA

Described herein are methods for using topoisomerase to clone DNA. Generally, the methods comprise use of a vector comprising topoisomerase recognition sites, nicking agent recognition sites, and, optionally, a stuffer fragment, a nicking agent, and a topoisomerase to clone a polynucleotide of interest into the vector. Each of these elements, along with others useful in the practice of the methods, is described below.

6.2.1. Topoisomerases and topoisomerase recognition sites

Topoisomerases catalyze the reversible cleavage of the phosphodiester backbone of DNA. Topoisomerases are categorized as type I, including type IA and type IB topoisomerases, which cleave a single strand of a double stranded nucleic acid molecule, and type II topoisomerases (gyrases), which cleave both strands of a nucleic acid molecule. As disclosed herein, type I and type II topoisomerases, as well as catalytic domains and mutant forms thereof, are useful for generating recombinant nucleic acid molecules as described herein. Type II topoisomerases have not generally been used for generating recombinant nucleic acid molecules or cloning procedures, whereas type IB topoisomerases are used in a variety of procedures.

Type IA and IB topoisomerases cleave one strand of a double stranded nucleic acid molecule. Cleavage of a nucleic acid molecule by type IA topoisomerases generates a 5' phosphate and a 3' hydroxyl at the cleavage site, with the type IA topoisomerase covalently binding to the 5' terminus of a cleaved strand. In comparison, cleavage of a nucleic acid molecule by type IB topoisomerases generates a 3' phosphate and a 5' hydroxyl at the cleavage site, with the type IB topoisomerase covalently binding to the 3' terminus of a cleaved strand. Type IA topoisomerases include, for example, $E. coli$ topoisomerase I and topoisomerase III, eukaryotic topoisomerase II, and archeal reverse gyrase (see Berger, Biochim. Biophys. Acta 1400:3-18, 1998).

Type IB topoisomerases include the nuclear type I topoisomerases present in all eukaryotic cells and those encoded by Vaccinia and other cellular poxviruses (see Cheng et al., Cell 92:841-850, 1998). The eukaryotic type IB topoisomerases are exemplified by those expressed in yeast, $Drosophila$ and mammalian cells, including human cells (see Caron and Wang, Adv. Pharmacol. 29B:271-297, 1994; Gupta et al., Biochim. Biophys. Acta 1262:1-14, 1995; see, also, Berger, supra, 1998). Viral type IB topoisomerases are exemplified by those produced by the vertebrate poxviruses (Vaccinia, Shope fibroma virus, ORF virus, fowlpox virus, and molluscum contagiosum virus), and the insect poxvirus (Amsacta moorei entomopoxvirus) (see Shuman, Biochim. Biophys. Acta 1400:321-337, 1998; Petersen et al., Virology 230:197-206, 1997; Shuman and Prescott, Proc. Natl. Acad. Sci., USA 84:7478-7482, 1987; Shuman, J. Biol. Chem. 269: 32678-32684, 1994; U.S. Pat. No. 5,766,891; PCT/US95/16099; PCT/US98/12372; see, also, Cheng et al., supra, 1998).

Type II topoisomerases include, for example, bacterial gyrase, bacterial DNA topoisomerase IV, eukaryotic DNA topoisomerase II, and T-even phage encoded DNA topoisomerases (Roca and Wang, Cell 71:833-840, 1992; Wang, J. Biol. Chem. 266:6659-6662, 1991; see also Berger, supra, 1998). Like the type IB topoisomerases, the type II topoisomerases have both cleaving and ligating activities. In addition, like type IB topoisomerase, substrate nucleic acid molecules can be prepared such that the type II topoisomerase can form a covalent linkage to one strand at a cleavage site. For example, calf thymus type II topoisomerase can cleave a substrate nucleic acid molecule containing a 5' recessed topoisomerase recognition site positioned three nucleotides from the 5' end, resulting in dissociation of the three nucleic acid molecule 5' to the cleavage site and covalent binding of the topoisomerase to the 5' terminus of the nucleic acid molecule (Andersen et al., supra, 1991). Furthermore, upon contacting such a type II topoisomerase-charged nucleic acid molecule with a second nucleic acid molecule containing a 3' hydroxyl group, the type II topoisomerase can ligate the sequences together, and then is released from the recombinant nucleic acid molecule. As such, type II topoisomerases also are useful for performing the methods described herein.

Structural analysis of topoisomerases indicates that the members of each particular topoisomerase families, including type IA, type IB and type II topoisomerases, share common structural features with other members of the family (Berger, supra, 1998). In addition, sequence analysis of various type IB topoisomerases indicates that the structures are highly conserved, particularly in the catalytic domain (Shuman, supra, 1998; Cheng et al., supra, 1998; Petersen et al., supra 1997). For example, a domain comprising amino acids 81 to 314 of the 314 amino acid Vaccinia topoisomerase shares substantial homology with other type IB topoisomerases, and the isolated domain has essentially the same activity as the full length topoisomerase, although the isolated domain has a slower turnover rate and lower binding affinity to the recognition site (see Shuman, supra, 1998; Cheng et al., supra, 1998).

In addition, a mutant Vaccinia topoisomerase, which is mutated in the amino terminal domain (at amino acid residues 70 and 72) displays identical properties as the full length topoisomerase (Cheng et al., supra, 1998). In fact, mutation analysis of Vaccinia type IB topoisomerase reveals a large number of amino acid residues that can be mutated without affecting the activity of the topoisomerase, and has identified several amino acids that are required for activity (Shuman, supra, 1998). In view of the high homology shared among the Vaccinia topoisomerase catalytic domain and the other type IB topoisomerases, and the detailed mutation analysis of Vaccinia topoisomerase, it will be recognized that isolated catalytic domains of the type IB topoisomerases and type IB topoisomerases having various amino acid mutations can be used in the methods described herein and thus are also considered to be topoisomerases.

The various topoisomerases exhibit a range of sequence specificity. For example, type II topoisomerases can bind to a variety of sequences, but cleave at a highly specific recognition site (see Andersen et al., J. Biol. Chem. 266:9203-9210, 1991, which is incorporated herein by reference.). In comparison, the type IB topoisomerases include site specific topoisomerases, which bind to and cleave a specific nucleotide sequence ("topoisomerase recognition site"). Upon cleavage of a nucleic acid molecule by a topoisomerase, for example, a type IB topoisomerase, the energy of the phosphodiester bond is conserved via the formation of a phosphotyrosyl linkage between a specific tyrosine residue in the topoisomerase and the 3' nucleotide of the topoisomerase recognition site. Where the topoisomerase cleavage site is near the 3' terminus of the nucleic acid molecule, the downstream sequence (3' to the cleavage site) can dissociate, leaving a nucleic acid molecule having the topoisomerase covalently bound to the newly generated 3' end.

The covalently bound topoisomerase also can catalyze the reverse reaction, for example, covalent linkage of the 3' nucleotide of the recognition sequence, to which a type IB topoisomerase is linked through the phosphotyrosyl bond, and a nucleic acid molecule containing a free 5' hydroxyl group. As such, methods have been developed for using a type IB topoisomerase to produce recombinant nucleic acid molecules. Nucleic acid molecules such as those comprising a cDNA library, or restriction fragments, or sheared genomic DNA sequences that are to be cloned into such a vector are treated, for example, with a phosphatase to produce 5' hydroxyl termini, then can be added to the linearized vector under conditions that allow the topoisomerase to ligate the nucleic acid molecules at the 5' terminus containing the hydroxyl group and the 3' terminus containing the covalently bound topoisomerase. A nucleic acid molecule such as a PCR amplification product, which is produced containing 5' hydroxyl ends, can be cloned into a topoisomerase-charged vector in a rapid joining reaction (approximately 5 min at room temperature). The rapid joining and broad temperature range inherent to the topoisomerase joining reaction makes the use of topoisomerase-charged vectors ideal for high throughput applications, which generally are performed using automated systems.

Vaccinia virus encodes a 314 amino acid type I topoisomerase enzyme capable of site-specific single-strand nicking of double stranded DNA, as well as 5' hydroxyl driven religation. Site-specific type I topoisomerases include, but are not limited to, viral topoisomerases such as pox virus topoisomerase. Examples of pox virus topoisomerases include Shope fibroma virus and ORF virus. Other site-specific topoisomerases are well known to those skilled in the art and can be used in the methods and compositions described herein.

Examples of other site-specific type I topoisomerases are well known in the art. These enzymes are encoded by many organisms including, but not limited to Saccharomyces cerevisiae, Saccharomyces pombe and Tetrahymena, however, the topoisomerase I enzymes of these species have less specificity for a consensus sequence than does the Vaccinia topoisomerase. (Lynn et al., Proc. Natl. Acad. Sci. USA 86: 3559-3563, 1989; Eng et al., J. Biol. Chem. 264: 13373-13376, 1989; Busk et al., Nature 327: 638-640, 1987).

The compositions and methods described herein are exemplified generally herein with reference to the use of type IB topoisomerase such as the Vaccinia topoisomerase. However, it will be recognized that the methods also can be performed using other topoisomerases merely by adjusting the components accordingly. For example, methods are disclosed for incorporating a type IB topoisomerase recognition site at one or both 3' termini of a nucleic acid molecule. Accordingly, in view of the present disclosure, the artisan will recognize that a topoisomerase recognition site for a type IA or type II topoisomerase similarly can be incorporated into a nucleic acid molecule. It should also be noted that more than one topoisomerase can be used in connection with a single polynucleotide by adjusting the components appropriately, e.g. by including appropriate recognition sites for the different topoisomerases in the vector to be used. Thus, the topoisomerases used in the methods can be the same, for example, two type IB topoisomerases, including two Vaccinia type IB topoisomerases, or can be different, including, for example, two type IB topoisomerases from different organisms or a type IB topoisomerase and a type IA or a type II topoisomerase.

Vaccinia DNA topoisomerase I exhibits a high level of sequence specificity; cleavage occurs at a consensus pentapyrimidine element 5'-(C/T)CCTT-3' in the scissile strand. In the cleavage reaction, bond energy is conserved via the formation of a covalent adduct between the 3' phosphate of the incised strand and a tyrosyl residue (Tyr-274) of the protein. Vaccinia topoisomerase can religate the covalently held strand across the same bond originally cleaved (as occurs during DNA relaxation) or it can religate to a heterologous acceptor DNA and thereby create a recombinant molecule.

Vaccinia topoisomerase I thus forms an adduct with DNA by a covalent linkage between a 3'-phosphate and a tyrosine within the protein. In the reverse reaction, vaccinia topoisomerase I will therefore catalyze formation of a covalent bond between that 3' phosphate and the 5' hydroxyl of another DNA segment. However vaccinia topoisomerase I will not efficiently catalyze formation of a covalent bond between that 3' phosphate and the 5' phosphate of another DNA segment. In preferred embodiments, the nicking agent used to break the DNA strand complementary to the topoisomerase cleavage sequence element, as discussed below, (for example as shown in FIG. 4) leaves a phosphate group attached to the 5' position of the deoxyribose sugar on one side of the break and a hydroxyl group attached to the 3' position of the deoxyribose sugar on the other side of the break (i.e. the cleavage agent "leaves a 5' phosphate"). This prevents vaccinia topoisomerase I from efficiently catalyzing circularization of the topoisomerase-charged vector, instead favoring joining of the vector DNA with a DNA segment that has a hydroxyl group on the 5' base.

Topoisomerase cleavage sequence elements include 5'-CCCTT-3', 5'-TCCTT-3', 5'-CCCTA-3' (Shuman, 1991. Journal/J Biol Chem, 266: 1796-1803.). Further, it is likely that relative affinity of sequence-specific topoisomerases is modulated by flanking sequence context (Shuman and Prescott, 1990. Journal/J Biol Chem, 265: 17826-17836.). In some embodiments, it may therefore be advantageous to design the sequences adjacent to the topoisomerase cleavage sequence element to modify the affinity between the topoisomerase and the topoisomerase cleavage sequence element. Six high affinity sites for vaccinia topoisomerase I in the plasmid pUC19 are: CAACATTTCCGTGTCGCCCTTATTCCCTTTTTTGCGGCAT (SEQ ID NO 11), GCTCGGCCCTTCCGG (SEQ ID NO 12), AGGCCCGCACCGATCGCCCTTCCCA (SEQ ID NO:13), CAAAATCCCTTAACG (SEQ ID NO:14), TGAAGATCCTTTTTG (SEQ ID NO:15), and ATTTTCTCCTTACGC (SEQ ID NO:16).

One preferred topoisomerase cleavage site is GTGTCGCCCTTATTC (SEQ ID NO:17).

6.2.2. Nicking the Topoisomerase Cleavage Sequence Element Complementary Strand

Vaccinia topoisomerase I cleaves only 1 strand of the DNA duplex. A vector that can accept a double-stranded polynucleotide insert should have a break in both strands.

Methods currently known in the art achieve this by a complex series of restriction digestions and oligonucleotide ligations (see for example (Heyman et al., 1999. Journal/Genome Res, 9: 383-392.), and U.S. Pat. No. 6,916,632). However an alternative method of preparing a vector that can accept a double-stranded polynucleotide insert is to cleave the other strand (the "topoisomerase cleavage sequence element complementary strand") with a nicking agent, as shown schematically in FIG. 1. In a preferred embodiment, such cleavage is achieved using a nicking endonuclease. Nicking endonucleases such as Nb.BsrDI, Nb.BbvCI, Nb.BsmI, Nt.BbvCI, NtCvPII, Nb.BtsI, Nt.AlwI and Nt.BstNBI are commercially available and can be used to create a break in one strand of the DNA backbone. Additional new nicking enzymes appear likely to be engineered, as a general method for their engineering has been described (Xu et al., 2001. Journal/Proc Natl Acad Sci USA, 98: 12990-12995; Zhu et al., 2004. Journal/J Mol Biol, 337: 573-583.).

Nicking endonucleases bind to a specific DNA sequence (the recognition sequence) and then cleave only one of the DNA strands at a predictable and specific site within or close to the recognition sequence. An example of placement of such a restriction site (in this example a site recognized by Nt.BstNBI) in relation to the topoisomerase cleavage sequence element is shown in FIG. 8. In FIG. 8, the nicking endonuclease recognition site is placed such that the nicking endonuclease Nt.BstNBI can break the DNA strand complementary to the DNA strand that will form an adduct with vaccinia DNA topoisomerase I. In FIG. 8, the nicking endonuclease recognition sequence is placed so that the nicking with Nt.BstNBI will cleave the DNA strand immediately 5' of the sequence 5'-AAGGG-3'. In other embodiments, the placement of the nicking enzyme site can be arranged relative to the topoisomerase cleavage sequence element to result in 5' or 3' overhangs following nicking and cleavage by topoisomerase. Such embodiments may be preferred for applications, for example, when the insert is to be cloned directionally.

In certain embodiments, the nicking agent recognition sites are placed in such a way that they direct the nicking agent to break a phosphodiester bond in the DNA backbone close to the topoisomerase cleavage sequence element, but on the opposite strand. One example of such an embodiment is shown in FIG. 4. In this Figure, one topoisomerase cleavage sequence element 5'-CCCTT-3' is present on the "top" strand, and a proximal nicking agent recognition site directs a nicking agent to cleave the "bottom" strand immediately 5' of the sequence 5'-AAGGG-3'. A second topoisomerase cleavage sequence element 5'-CCCTT-3' is present on the "bottom" strand, and a proximal nicking agent recognition site directs a nicking agent to cleave the "top" strand immediately 5' of the sequence 5'-AAGGG-3'. When a vector containing such a cloning cassette is cleaved in such a way and exposed to vaccinia topoisomerase I, both DNA strands are cleaved with the release of DNA sequences between the two topoisomerase cleavage sequence elements, as shown schematically in FIG. 5.

In certain preferred embodiments, nicking endonucleases are used as the nicking agent. These enzymes are directed to break one strand of the DNA by the presence of a recognition sequence within the DNA. FIG. 7 shows an embodiment as shown in FIG. 4, in which the cleavage agent used is the nicking endonuclease Nt.BstNBI which recognizes the sequence 5'-GAGTC-3' and cleaves after the fourth nucleotide following the recognition sequence. One skilled in the art will readily recognize that any endonuclease that cleaves only one strand of the DNA duplex can be used, and that the precise placement of the nicking endonuclease recognition site will determine exactly where the DNA is nicked.

FIGS. 4, 5 and 7 show certain preferred embodiments. In these embodiments, addition of nicking agent and topoisomerase results in two double-stranded breaks in the cloning cassette, wherein the 3' end of each strand is charged with topoisomerase (see FIG. 5). The placement of nicking agent recognition sites in this preferred embodiment is such that the double stranded breaks that result from treatment of the DNA with nicking agent and topoisomerase produce blunt ended DNA fragments.

In other preferred embodiments, the nicking agent recognition sites can be placed so that the double stranded breaks that result from treatment of the DNA with nicking agent followed by addition of topoisomerase produce DNA breaks with 5' or 3' overhangs. Different nicking agents can be used to cleave near the two topoisomerase cleavage sequence elements. Furthermore the nicking agent recognition sites can be placed so that the two DNA breaks are different from one another, for example one break may have a 5' overhang while the other break is blunt (see for example FIGS. 9, 10 and 11), or both breaks could have 5' or 3' overhangs but the overhang at one break may have a different sequence from the overhang at the other break. Similarly, one break may result in a 5' overhang while the other results in a 3' overhang of the same or different sequences. The overhangs may comprise, for example, from 1 to 100 nucleotides, from 1 to 75 nucleotides, from 1 to 50 nucleotides, from 1 to 25 nucleotides, from 1 to 15 nucleotides, from 1 to 10 nucleotides, or from 1 to 8 nucleotides. In certain embodiments, the overhang comprises 1, 2, 3, 4, 5, 6, 7, 8, 9, or 10 nucleotides.

In some preferred embodiments one or more nicking agent recognition sites can be placed so that the double stranded breaks that result from treatment of the DNA with nicking agent followed by addition of topoisomerase produce DNA breaks with 5' or 3' overhangs to facilitate directional cloning. Examples of such cleavages leaving 5' overhangs of 6, 4 or 2 bases are shown respectively in FIGS. 9, 10 and 11. Directional cloning can then be achieved by adding the sequence complementary to the 5' overhang to the end of the DNA to be cloned: the end that is complementary to the vector overhang will be preferentially joined to that end of the vector. In one preferred embodiment, complementary bases can be added by amplifying the DNA to be cloned using the polymerase chain reaction. Addition of a sequence complementary to the 5' overhang of the vector to the 5' end of one of the PCR primers used for the DNA amplification can result in addition of those bases to the amplified DNA.

It should be noted that the entire vector sequence should be checked for the presence of additional topoisomerase cleavage sequence elements or nicking agent recognition sites. Preferably, such sites should not be close enough together to produce a double stranded break in the vector DNA that will result in undesired dissociation of portions of the vector DNA. The presence of additional topoisomerase cleavage sequence elements or nicking agent recognition sites within the vector that do not result in undesired dissociation of portions of the vector DNA should not interfere with the cloning methods described herein. This is because breaks in only 1 strand of the DNA will be repaired upon transformation into the host cell. In the cloning cassette configuration for cloning using sequence-specific topoisomerase (for example as shown in FIG. 2), a nicking agent recognition site and its associated topoisomerase cleavage sequence element are juxtaposed such that they produce breaks in both DNA strands within 20 nucleotides of each other, more preferably within 10 nucleotides of each other, even more preferably within 5 nucleotides of each other. The resulting overhang is so short that cleavage is accompanied by spontaneous dissociation of the downstream portions of the cleaved strands. Nicking or topoisomerase addition at other sites in the molecule that does not result in spontaneous dissociation of the DNA strands should thus not have a strong adverse effect on the cloning reaction.

Current methods described in the art for cloning using sequence-specific topoisomerase require laborious and time-consuming procedures to prepare the vector. Some of these procedures are required to produce a DNA vector molecule with the desired breaks at the ends and a topoisomerase adduct at each of the 3' ends (Heyman et al., 1999. Journal/Genome Res, 9: 383-392.)(see U.S. Pat. Nos. 5,766,891; 6,548,277; 6,653,106; 6,916,632 and 7,026,141). The use of sequence-directed cleavage agents as described herein greatly reduces the time and effort required to obtain such a topoisomerase-charged vector DNA molecule.

6.2.3. Cloning Cassettes

A cloning cassette can thus be constructed to permit cloning using vaccinia topoisomerase I. A general schematic representation of such a cloning cassette is shown in FIG. 2. In this cassette design, two topoisomerase cleavage sequence elements are placed in opposite orientation to each other. Topoisomerase cleavage sequence elements include 5'-CCCTT-3',5'-TCCTT-3',5'-CCCTA-3'. In proximity to each of these two topoisomerase cleavage sequence elements are sequence elements that direct a nicking agent to cleave the strand of DNA containing the complement of the topoisomerase cleavage sequence. In preferred embodiments these nicking agent recognition sites flank an additional region of DNA sequence: a "stuffer" sequence that is removed when the desired insert is cloned. A more specific embodiment of this kind of cloning cassette is shown in FIG. 3. In this embodiment 5'-CCCTT-3' is used as the topoisomerase cleavage sequence element. This Figure is shown to demonstrate that one embodiment of placing the topoisomerase cleavage sequence elements in opposite orientation results in a cloning cassette whose sequence is 5'-CCCTTN$_{(j)}$AAGGG-3', where N$_{(j)}$ represents any number of nucleotides.

As described above, it is likely that relative affinity of sequence-specific topoisomerases is modulated by flanking sequence context. Accordingly, in certain embodiments, the cloning cassette can comprise one or more of six high affinity sites for vaccinia topoisomerase I in the plasmid pUC19: CAACATTTCCGTGTCGCCCTTATTC-CCTTTTTTGCGGCAT (SEQ ID NO 11), GCTCGGCCCT-TCCGG (SEQ ID NO 12), AGGCCCGCACCGATCGC-CCTTCCCA (SEQ ID NO:13), CAAAATCCCTTAACG (SEQ ID NO:14), TGAAGATCCTT<u>TTTG</u> (SEQ ID NO:15), or ATTTTCTCCTTACGC (SEQ ID NO:16).

Accordingly, in certain embodiments, the sequences adjacent to the topoisomerase cleavage sequence element can be selected to more closely resemble the context of a high affinity topoisomerase site. An example of such a cloning cassette is shown in FIG. 12 and the sequence of such a cloning cassette is provided as SEQ ID NO:4. In certain embodiments six bases to the 5' and four bases to the 3' of the topoisomerase cleavage sequence element SEQ ID NO 11 are sufficient to yield a high affinity site for use in topoisomerase cloning. In certain embodiments, the cloning cassette comprises one or more topoisomerase recognition sites that have the sequence 5'-GTGTCGCCCTTATTC-3' (SEQ ID NO:17).

The cloning cassette can further comprise a pair of nicking agent recognition sites as described herein. The nicking agent recognition sites can be oriented relative to the topoisomerase recognition sites to result in blunt ends following nicking and cleavage by topoisomerase as described herein. Alternately, the nicking agent recognition sites can be oriented relative to the topoisomerase recognition sites to result in a 5' or 3' overhang following nicking and cleavage by topoisomerase as described herein. In certain embodiments, the cloning cassette comprises one or more topoisomerase recognition sites and nicking agent sites that have the sequence 5'-CCCTTAT-TCGACTC-3' (SEQ ID NO:18), or 5'-CCCTTAGCT-GACTC-3' (SEQ ID NO:19), or 5'-CCCTTATTCGATCC-3' (SEQ ID NO:20).

The cloning cassette can further comprise a stuffer fragment as described herein. Optionally, the stuffer fragment can comprise a marker, a counter-selectable marker, and/or a cleavage site, as described below.

6.2.4. Stuffer Fragments, Markers, and Counter-Selectable Markers

For cloning to be most useful, it is helpful to distinguish between transformants that carry the desired insert from those that do not. In the methods described herein, this involves primarily distinguishing between transformants propagating vector carrying sequences that were originally present in the vector (and that were then released from the vector by the actions of the nicking agent and topoisomerase, and subsequently re-joined into the vector by topoisomerase), and the desired insert. Accordingly, one aspect of the methods is the design of sequences within the cloning cassette that result in a specific phenotype when present in a host cell. One example of such a phenotype is a change in color. For example, if the vector contains a stuffer fragment that directs the cell to synthesize a fluorescent protein, then all of the colonies that contain the fluorescent protein are carrying vector stuffer fragment sequences and are therefore unlikely to be carrying the desired insert. Thus the cells that will be selected for further analysis are those that do not contain the fluorescent protein. Similarly the stuffer fragment could contain a protein that participates in catalyzing a chromogenic reaction, for example, hydrolysis of 5-bromo-4-chloroindoxyl-beta-galactoside (X-gal). Any such fluorescent proteins and chromogenic substrates known in the art can be used in the methods, compositions, and kits described herein.

A stuffer fragment that results in (or inhibits) a chromogenic reaction or is detected by, for example, fluorescence, is generally used to screen transformants to identify those that are likely to contain the desired insert. In more preferred embodiments, the stuffer fragment encodes an activity that either prevents the growth of a host cell or kills a host cell into which the stuffer fragment is transformed. A DNA segment encoding such an activity is often referred to as a counter-selectable marker. Many counter-selectable markers are known in the art including ccdB, kid and barnase (Bernard, 1995. Journal/Gene, 162: 159-160; Bernard et al., 1994. Journal/Gene, 148: 71-74; Gabant et al., 1997. Journal/Biotechniques, 23: 938-941; Gabant et al., 1998. Journal/Gene, 207: 87-92; Gabant et al., 2000. Journal/Biotechniques, 28: 784-788; Galvao and de Lorenzo, 2005. Journal/Appl Environ Microbiol, 71: 883-892; Hartzog et al., 2005. Journal/Yeast, 22: 789-798; Knipfer et al., 1997. Journal/Plasmid, 37: 129-140; Reyrat et al., 1998. Journal/Infect Immun, 66: 4011-4017; Soderholm et al., 2001. Journal/Biotechniques, 31: 306-310, 312; Tamura et al., 2005. Journal/Appl Environ Microbiol, 71: 587-590; Yazynin et al., 1999. Journal/FEBS Lett, 452: 351-354.).

If a counter-selectable marker is used in the stuffer fragment of a vector used as described herein, then any cell that is transformed with a vector into which the stuffer fragment has been re-inserted, and then grown under restrictive conditions, will not grow. Thus the transformants that grow will predominantly be those carrying vector into which the desired insert has been cloned. Using a stuffer fragment containing a counter-selectable marker therefore means that vector DNA, insert DNA and sequence-specific topoisomerase can all be mixed together; the resulting reaction mixture can be transformed into host cells without removal of the stuffer fragment or purification of topoisomerase-charged vector and the majority of transformants that grow will be those carrying the desired insert polynucleotide.

As described above, the sequences released from the vector by the actions of the topoisomerase and the nicking agent that cleaves the topoisomerase cleavage sequence element complementary strand preferably are prevented from being re-inserted into the vector by the topoisomerase and then producing viable transformed host cells. This goal can be accomplished by using a stuffer fragment that contains a counter-selectable marker. Alternately, it can be accomplished by treating the vector DNA with a DNA cleavage agent that cleaves the vector within the stuffer fragment. In this embodiment, at least one end of each resulting DNA fragment should be in a form that prevents topoisomerase from joining them to the ends of the vector DNA. In a preferred embodiment, the cleavage agent is one or more nicking endonuclease or restriction endonuclease whose combined actions cause one or more double-stranded breaks in the DNA of the stuffer fragment. Restriction endonucleases cleave DNA so that the resulting DNA ends have a 5'-phosphate and a 3'-hydroxyl group. Vaccinia topoisomerase I will join a 3'-phosphate of a donor polynucleotide to a 5'-hydroxyl of an acceptor polynucleotide. DNA fragments with ends resulting from the action of restriction endonucleases which have 5'-phosphate groups are therefore not substrates for joining by vaccinia topoisomerase I. Methods for design and synthesis of stuffer fragments containing restriction recognition sequences that will result in double-stranded breaks within the stuffer but not in the remainder of the vector are well known in the art; any such method can be used in accordance with the methods described herein.

In another preferred embodiment, one or more DNA segments from the stuffer fragment can be removed by treatment with one or more cleavage agents. Optionally the vector DNA can then be purified to separate the vector DNA from the DNA segments removed from the stuffer fragment. In certain embodiments, the cleavage agent used is a restriction endonuclease and the vector DNA is purified by agarose gel electrophoresis. Such methods are well known in the art. In such embodiment, the vector DNA that has been cleaved one or more times within the stuffer can preferably be purified, for example by size fractionation on an agarose gel followed by extraction from the agarose, before treatment with a nicking agent that cleaves the vector DNA on the topoisomerase cleavage sequence element complementary strand (examples of which nicking are shown in FIGS. 1, 8, 4 and 7). This is because methods and protocols for DNA purification, particularly purification from agarose gels, can cause dissociation between parts of the DNA strands in a DNA duplex. Dissociation of the topoisomerase cleavage sequence element complementary strand from the topoisomerase cleavage sequence element could therefore happen if DNA purification is performed after treatment of the vector DNA with the nicking agent designed to cleave the topoisomerase cleavage sequence element complementary strand close to the topoisomerase cleavage sequence element. Such dissociation would decrease the efficiency of the reaction, since vaccinia topoisomerase I prefers a double-stranded DNA substrate.

In embodiments where a cleavage agent is used to introduce a double-stranded break in the stuffer fragment, the cleavage agent is preferably selected such that the stuffer fragment but not the vector polynucleotide is cleaved. Thus, in certain embodiments, the stuffer fragment is constructed to contain a sequence cleaved by a cleavage agent that is not present in the vector outside of the stuffer fragment. In certain embodiments, the cleavage agent is a restriction endonuclease that recognizes a larger than average sequence, for example, 5 or 6 or 7 or 8 or more nucleotides in the recognition sequence.

6.2.5. Preparation of the Insert Polynucleotide

Any method known by one skilled in the art can be used to prepare a second polynucleotide to be cloned as described herein. In certain advantageous embodiments, the polymerase chain reaction (PCR) can be used to prepare the insert.

6.2.6. Directional Topoisomerase Cloning

In some embodiments, it may be desirable to control the orientation of the cloned insert relative to sequence elements within the vector. Examples include transcription and translation signals (see FIG. 15) which may be present in a vector to direct the production of polyribonucleotides or polypeptides encoded by the DNA to be cloned.

The orientation of an insert cloned using topoisomerase can be controlled by creating a 5' or 3' overhang at one end of the vector, preferably a 5' overhang. The overhang is preferably between 2 and 6 bases in length (see for example FIGS. 9, 10 and 11). Such overhangs may be produced by offsetting the nicking agent recognition site relative to the topoisomerase cleavage sequence element, so that the nicking agent does not nick directly opposite the bond that will be broken by topoisomerase.

The end of the insert that is to be oriented towards the part of the vector containing the 5' or 3' overhang, should have bases complementary to the vector overhang on its 5' to 3' strand. In a preferred embodiment, these bases may be added by amplifying the insert by the polymerase chain reaction using a primer to which the extra bases have been added to the 5' end. See for example FIG. 16.

6.2.7. Simultaneous Mixing of Vector, Insert & Topoisomerase Protein

Another laborious and difficult aspect of previous methods described in the art for cloning using sequence-specific topoisomerase is that they require the purification of a DNA-protein adduct. Described herein are methods, compositions, and kits that obviate this requirement as described below. Treatment of a vector DNA configured as shown in FIG. 2 with a nicking agent and a sequence-specific topoisomerase results in two double stranded breaks in the DNA. An example of this is shown in FIG. 5. Preparing a single mixture that contains vector DNA (that has been pre-treated with the nicking agent), topoisomerase and the polynucleotide insert to be cloned will result in an equilibrium reaction. In this reaction, the topoisomerase will form an adduct with the vector DNA and release the DNA sequences that were contained between the two topoisomerase cleavage sequence elements. This DNA segment will then compete with the polynucleotide insert to be cloned in the reverse reaction in which topoisomerase joins the 5'-hydroxyl group of the acceptor DNA to the 3'-phosphate of the donor DNA (in this case the vector DNA). This equilibrium is shown in FIG. 6. The result is a mixture of linear DNA segments including the topoisomerase-bound vector DNA and circular vector DNA (FIG. 6 part A), as well as circular vector containing either the sequences that were originally part of the vector (e.g., the stuffer fragment) or the polynucleotide insert to be cloned (FIG. 6 part B). Transformation of this mixture into a host cell will result in replication and propagation of both of the circular plasmids, but not of the linear topoisomerase-bound vector.

Preferred mixtures of vector, insert and topoisomerase for cloning contain vector concentrations between 1 pM and 1 µM, more preferred mixtures contain vector concentrations between 10 pM and 100 nM, more preferred mixtures contain vector concentrations between 100 pM and 10 nM. In such mixtures, the insert DNA is preferably present at a molar concentration greater than or equal to the molar concentration of the vector DNA, more preferably the insert DNA is present at a molar concentration at least twice the molar concentration of the vector DNA, even more preferably the insert DNA is present at a molar concentration at least four times the molar concentration of the vector DNA. In such mixtures the topoisomerase is preferably present at a molar concentration of greater than or equal to the molar concentration of the vector DNA, more preferably the topoisomerase is present at a molar concentration of at least 5 times the molar concentration of the vector DNA, even more preferably the topoisomerase is present at a molar concentration of at least 10 times the molar concentration of the vector DNA. If the topoisomerase concentration is not defined but instead the manufacturer describes the activity of the topoisomerase in units (Unit Definition: One unit of Vaccinia Topoisomerase I will convert 1 µg of supercoiled DNA (Form I) to relaxed closed circular DNA (Form II) in 1 hour at 37° C. in 40 mM Tris-acetate (pH 8.3), 1 mM EDTA, 2.5 mM $MgCl_2$, and 100 mM NaCl), then preferred mixtures of vector, insert and topoisomerase contain between 50-fold and 1,000-fold excess of enzyme (expressed in U/ml) over vector (expressed in nM): for example for vector concentrations of 0.1 nM, preferred mixtures contain between 5 and 100 U/ml of topoisomerase; for vector concentrations of 1 nM, preferred mixtures contain between 500 and 10,000 U/ml of topoisomerase.

In further embodiments, the methods can further include contacting the vector and insert with a third nucleic acid, wherein one end of the third nucleic acid has a second topoisomerase covalently bound at the 3' terminus and the other end has a 5' hydroxyl. The contacting can be performed, for example, under conditions such that the 5' nucleotide sequence of the insert acid can selectively hybridize to a 5' overhang of the end of the third nucleic acid having the 3' topoisomerase bound thereto, whereby the topoisomerase can covalently link the 3' terminus of the third nucleic acid with the 5' terminus of the insert. The topoisomerases bound to the vector and the third nucleic acid can be the same or different and, if desired, the vector or third nucleic acid, instead of having topoisomerase bound thereto, can contain a topoisomerase recognition site. A method can be performed such that the first nucleic acid molecule is directionally linked to the second nucleic acid molecule and, thereafter, the third nucleic acid molecule is directionally or non-directionally linked to the second nucleic acid molecule, or all of the reactants can be included together at the same time.

6.2.8. Temporal Order of Events

The sequence of events shown in some of the drawings (for example FIG. 1, FIG. 5) is that the vector DNA is first treated with a nicking agent and then mixed with topoisomerase and the polynucleotide insert to be cloned. The steps are represented sequentially in these Figures to clarify teaching regarding the described reactions and should not be construed to represent a requirement for a temporal order in which the reactions are performed.

In some embodiments, the nicking agent to be used has a different temperature optimum from the optimum temperature for the topoisomerase-catalyzed reactions. Nicking endonuclease Nb.BsmI has a maximal activity at 65° C., Nt.BstNBI has a maximal activity at 55° C., but vaccinia topoisomerase I has maximal activity between 30° C. and 37° C. Therefore in embodiments where the nicking agent is the nicking endonuclease Nb.BsmI, Nt.BstNBI or a nicking agent whose maximal activity occurs at temperatures that are higher than 37° C. it may be advantageous to perform the nicking step prior to the addition of topoisomerase and the polynucleotide insert to be cloned.

In other embodiments, the nicking agent to be used has a similar temperature optimum to the optimum temperature for the topoisomerase-catalyzed reactions. Nicking endonucleases Nb.BsrDI, Nt.BtsI and Nt.AlwI have maximal activity at 37° C. Therefore in embodiments where the nicking agent is the nicking endonuclease Nb.BsrDI, Nt.BtsI and Nt.AlwI or a nicking agent whose maximal activity occurs at temperatures between 30° C. and 37° C., it may be advantageous to perform the nicking step simultaneously with the addition of topoisomerase and the polynucleotide insert to be cloned.

In some embodiments, therefore, it is possible to mix in a single tube the vector DNA, nicking agent, sequence-specific topoisomerase and the polynucleotide insert to be cloned. Incubation of the mixture at a temperature where the nicking agent and topoisomerase are both active will result in cloning of the polynucleotide insert.

6.3 VECTORS AND METHODS FOR PREPARING VECTORS FOR ONE-STEP TOPOISOMERASE CLONING

Any vector can be converted to a vector capable of supporting one-step topoisomerase cloning. This can be done by designing and synthesizing a nucleic acid sequence for a cloning cassette as described herein, then cloning that cassette into the vector to be converted. Such design and synthesis methods are well known in the art. The conversion of vectors to allow one-step topoisomerase cloning is expressly contemplated. Further, use of such vectors as described below in the methods, compositions, and kits described herein is expressly contemplated.

DNA cloning cassettes of the form shown in FIG. 2 can also be designed and synthesized with unique restriction sites to permit their cloning into other vectors. The use of such cloning cassettes to convert other vectors to one-step topoisomerase cloning vectors, or the use of such cassettes as a component of kits for conversion of vectors to allow one-step topoisomerase cloning are also expressly contemplated.

Of course, one of skill in the art will recognize that alternate methods can be used to construct a vector suitable for use in the methods, compositions, and kits described herein. For example, oligonucleotides containing appropriate topoisomerase recognition sequences and nicking agent recognition sequences can be synthesized and introduced into the vector using standard techniques.

Vectors that can be converted for use in the methods described herein are legion. In one embodiment, the vector can be a cloning vector or an expression vector. The vector can include elements such as a bacterial origin of replication, a eukaryotic origin of replication, antibiotic resistance genes, and the like. The vector can be a plasmid vector, a cosmid vector, an artificial chromosome (e.g., a bacterial artificial chromosome, a yeast artificial chromosome, a mammalian artificial chromosome, etc.) or a viral vector such as a bacteriophage, baculovirus, retrovirus, lentivirus, adenovirus, Vaccinia virus, semliki forest virus and adeno-associated virus vector, all of which are well known and can be purchased from commercial sources (Promega, Madison Wis.; Stratagene, La Jolla Calif.; GIBCO/BRL, Gaithersburg Md.). Viral expression vectors can be particularly useful where a method is practiced for the purpose of generating a recombinant nucleic acid molecule that is to be introduced into a cell, particularly a cell in a subject. Viral vectors provide the advantage that they can infect host cells with relatively high efficiency and can infect specific cell types or can be modified to infect particular cells in a host.

Viral vectors have been developed for use in particular host systems and include, for example, baculovirus vectors, which infect insect cells; retroviral vectors, other lentivirus vectors such as those based on the human immunodeficiency virus (HIV), adenovirus vectors, adeno-associated virus (AAV) vectors, herpesvirus vectors, Vaccinia virus vectors, and the like, which infect mammalian cells (see Miller and Rosman, BioTechniques 7:980-990, 1992; Anderson et al., Nature 392: 25-30 Suppl., 1998; Verma and Somia, Nature 389:239-242, 1997; Wilson, New Engl. J. Med. 334:1185-1187, 1996, each of which is incorporated herein by reference). For example, a viral vector based on an HIV can be used to infect T cells, a viral vector based on an adenovirus can be used, for example, to infect respiratory epithelial cells, and a viral vector based on a herpesvirus can be used to infect neuronal cells. Other vectors, such as AAV vectors can have greater host cell range and, therefore, can be used to infect various cell types, although viral or non-viral vectors also can be modified with specific receptors or ligands to alter target specificity through receptor mediated events.

The vector also can contain, for example, expression control elements required for replication in a prokaryotic host cell, a eukaryotic host cell, or both, and can contain a nucleotide sequence encoding a polypeptide that confers antibiotic resistance or the like, or such elements can be introduced into the vector using conventional techniques. Furthermore, the vector can contain one, two, or more site specific integration recognition site such as an att site or lox site. The incorporation, for example, of attB or attP sequences into an isolated nucleic acid molecule allows for the convenient manipulation of the nucleic acid molecule using the GATEWAY™ Cloning System (Invitrogen Corp., La Jolla Calif.).

The vectors can further be used to transcribe RNA or express a polypeptide from an open reading from a cDNA or an isolated genomic DNA sequence by operatively linking one or more expression control elements to the putative coding sequence. Examples of expression control elements include, for example, transcriptional expression control elements, translational expression control elements, elements that facilitate the transport or localization of a nucleic acid molecule or polypeptide in (or out of) a cell, elements that confer a detectable phenotype, and the like. Transcriptional expression control elements include, for example, promoters such as those from cytomegalovirus, Moloney leukemia virus, and herpes virus, as well as those from the genes encoding metallothionein, skeletal actin, phosphoenolpyruvate carboxylase, phosphoglycerate, dihydrofolate reductase, and thymidine kinase, as well as promoters from viral long terminal repeats (LTRs) such as Rous sarcoma virus LTR; enhancers, which can be constitutively active such as an immunoglobulin enhancer, or inducible such as SV40 enhancer; and the like. For example, a metallothionein promoter is a constitutively active promoter that also can be induced to a higher level of expression upon exposure to a metal ion such as copper, nickel or cadmium ion. In comparison, a tetracycline (tet) inducible promoter is an example of a promoter that is induced upon exposure to tetracycline, or a tetracycline analog, but otherwise is inactive.

A transcriptional expression control element also can be a tissue specific expression control element, for example, a muscle cell specific expression control element, such that expression of an encoded product is restricted to the muscle cells in an individual, or to muscle cells in a mixed population of cells in culture, for example, an organ culture. Muscle cell specific expression control elements including, for example, the muscle creatine kinase promoter (Sternberg et al., Mol. Cell. Biol. 8:2896-2909, 1988) and the myosin light chain enhancer/promoter (Donoghue et al., Proc. Natl. Acad. Sci., USA 88:5847-5851, 1991) are well known in the art. Other tissue specific promoters, as well as expression control elements only expressed during particular developmental stages of a cell or organism are well known in the art.

Expression control or other elements useful in the vectors can be obtained in various ways. In particular, many of the elements are included in commercially available vectors and can be isolated therefrom and can be modified as disclosed herein. In addition, the sequences of or encoding the elements useful herein generally are well known and disclosed in publications. In many cases, the elements, for example, transcriptional and translational expression control elements, as well as cell compartmentalization domains, are relatively short sequences and, therefore, are amenable to chemical synthesis of the element or a nucleotide sequence encoding the element.

In certain embodiments, the vectors prepared for use in the methods described herein can encode a cell compartmentalization domain, such as a plasma membrane localization domain, a nuclear localization signal, a mitochondrial membrane localization signal, an endoplasmic reticulum localization signal, or the like, or a protein transduction domain such as the human immunodeficiency virus TAT protein transduction domain, which can facilitate translocation of a peptide linked thereto into a cell (see Schwarze et al., Science 285: 1569-1572, 1999; Derossi et al., J. Biol. Chem. 271:18188, 1996; Hancock et al., EMBO J. 10:4033-4039, 1991; Buss et al., Mol. Cell. Biol. 8:3960-3963, 1988; U.S. Pat. No. 5,776, 689). Such a domain can be useful to target a fusion polypeptide comprising the domain and a polypeptide encoded by an insert nucleic acid, to which it is linked, e.g., directionally linked, as described herein, to a particular compartment in the cell, or for secretion from or entry into a cell. As such, provided herein are means to generate linked, for example, directionally linked, recombinant nucleic acid molecules that encode a chimeric polypeptide.

A fusion polypeptide expressed from a recombinant nucleic acid molecule also can comprise a peptide having the characteristic of a detectable label or a tag such that the expressed fusion polypeptide can be detected, isolated, or the like. For example, a vector containing a topoisomerase recognition site, or cleavage product thereof, as disclosed herein, can encode an enzyme such as alkaline phosphatase, β-galactosidase, chloramphenicol acetyltransferase, luciferase, or other enzyme; or can encode a peptide tag such as a polyhistidine sequence (e.g., hexahistidine), a V5 epitope, a c-myc epitope; a hemagglutinin A epitope, a FLAG epitope, or the like. Expression of a fusion polypeptide comprising a detectable label can be detected using the appropriate reagent, for example, by detecting light emission upon addition of luciferin to a fusion polypeptide comprising luciferase, or by detecting binding of nickel ion to a fusion polypeptide comprising a polyhistidine tag. Of course, when embodiments are used where the stuffer fragment comprises a marker, a different marker should be used to detect the fusion-protein product.

The vector can also encode a polyhistidine tag comprising from about two to about ten contiguous histidine residues (e.g., two, three, four, five, six, seven, eight, nine, or ten contiguous histidine residues). The tag can also be a peptide tag which binds nickel ions, as well as other metal ions (e.g., copper ion), and can be used for metal chelate affinity chromatography. Examples of such tags include peptides having the formula: $R_1$-(His-X)$_n$—$R_2$, wherein (His-X) n represents a metal chelating peptide and n is a number between two through ten (e.g., two, three, four, five, six, seven, eight, nine, or ten), and X is an amino acid selected from the group consisting of alanine, arginine, aspartic acid, asparagine, cysteine, glutamic acid, glutamine, glycine, histidine, iso-leucine, leucine, lysine, methionine, phenylalanine, proline, serine, threonine, tryptophan, tyrosine and valine. Further, $R_2$ may be a polypeptide which is covalently linked to the metal chelating peptide and $R_1$ may be either a hydrogen or one or more (e.g., one, two, three, four, five, six, seven, eight, nine, ten, twenty, thirty, fifty, sixty, etc.) amino acid residues. In addition, $R_1$ may be a polypeptide which is covalently linked to the metal chelating peptide and $R_2$ may be either a hydrogen or one or more (e.g., one, two, three, four, five, six, seven, eight, nine, ten, twenty, thirty, fifty, sixty, etc.) amino acid residues. Tags of this nature are described in U.S. Pat. No. 5,594,115.

Similarly, isolation of a fusion polypeptide comprising a tag can be performed, for example, by passing a fusion polypeptide comprising a myc epitope over a column having an anti-c-myc epitope antibody bound thereto, then eluting the bound fusion polypeptide, or by passing a fusion polypeptide comprising a polyhistidine tag over a nickel ion or cobalt ion affinity column and eluting the bound fusion polypeptide. Methods for detecting or isolating such fusion polypeptides will be well known to those in the art, based on the selected detectable label or tag (see, for example, Hopp et al., Bio-Technology 6:1204, 1988; U.S. Pat. No. 5,011,912).

In one embodiment, the recombinant nucleic acid molecules encode chimeric polypeptides useful for performing a two hybrid assay. In such a method, the vector encodes a polypeptide, or a relevant domain thereof, that is suspected of having or being examined for the ability to interact specifically with one or more (e.g., 1, 2, 3, 4, 5, 6, 7, 8, 9, 10, etc.) other polypeptides. The insert nucleic acid, to which the vector is to be linked as described herein, can encode a transcription activation domain or a DNA binding domain. For example, a first nucleic acid molecules to be directionally linked is modified, for example, to contain an 5' overhang on a first end and a topoisomerase recognition site, or cleavage product thereof, at or near the first end. A second nucleic acid molecules to be linked contains, or is modified to contain, a 5' sequence complementary to the 5' overhang at the first end of the first nucleic acid molecule. Upon contact of the first and second nucleic acid molecules with a topoisomerase, the directionally linked nucleic acid molecule encodes a first hybrid useful for performing a two hybrid assay (see, for example, Fields and Song, Nature 340:245-246, 1989; U.S. Pat. No. 5,283,173; Fearon et al., Proc. Natl. Acad. Sci., USA 89:7958-7962, 1992; Chien et al., Proc. Natl. Acad. Sci. USA 88:9578-9582, 1991; Young, Biol. Reprod. 58:302-311 (1998). Similar methods are used to generate the second hybrid protein, which can comprise a plurality of polypeptides to be tested for the ability to interact with the polypeptide, or domain thereof, of the first hybrid protein. Such methods similarly can be used to construct directionally linked nucleic acid molecules encoding fusion protein useful for a modified form of a two hybrid assay such as the reverse two hybrid assay (Leanna and Hannink, Nucl. Acids Res. 24:3341-3347, 1996), the repressed transactivator system (U.S. Pat. No. 5,885,779), the protein recruitment system (U.S. Pat. No. 5,776,689), and the like.

The vectors can be used to construct, for example, a DNA library. In such embodiments, the insert can be one of a plurality of nucleic acid molecules, for example, a cDNA library, a combinatorial library of nucleic acid molecules, or a population of variegated nucleic acid molecules. As such, the methods are particularly useful for generating recombinant polynucleotides encoding chimeric polypeptides for performing a high throughput two hybrid assay for identifying protein-protein interactions that occur among populations of polypeptides (see U.S. Pat. No. 6,057,101 and U.S. Pat. No. 6,083,693). In such a method, each of the hybrid proteins of the two hybrid assay is generated using a different one of two populations (pluralities) of nucleic acid molecules encoding polypeptides, each plurality having a complexity of from a few related but different nucleic acid molecules to as high as tens of thousands of such molecules. By, for example, using a PCR primer pair to amplify each nucleic acid molecule in a plurality, directionally linked recombinant polynucleotides encoding a population of chimeric bait polypeptides and a population of chimeric prey polypeptides readily can be generated. Such populations are generated by contacting the amplified pluralities of nucleic acid molecules, each of which comprises an appropriate end, with a topoisomerase and a nucleic acid molecule which contains a topoisomerase recognition site at or near its ends and encodes a transcription activation domain or a DNA binding domain.

A vector useful in the methods described herein also can encode a ribonucleic acid (RNA) molecule, which can function, for example, as a riboprobe, an antisense nucleic acid molecule, a ribozyme, or a triplexing nucleic acid molecule, or can be used in an in vitro translation reaction, and the second nucleic acid molecule can encode an expression control element useful for expressing an RNA from the first nucleic acid molecule. For example, where it is desired to produce a large amount of RNA, a second nucleic acid molecule component for performing a method as described herein can comprise an RNA polymerase promoter such as a T7, T3 or SP6 RNA polymerase promoter. Where the RNA molecule is to be expressed in a cell, for example, an antisense molecule to be expressed in a mammalian cell, the second (or other) nucleic acid molecule can include a promoter that is active in a mammalian cell, particularly a tissue specific promoter, which is active only in a target cell. Furthermore, where the RNA molecule is to be translated, for example, in a coupled in vitro transcription/translation reaction, the first nucleic acid molecule or second (or other) nucleic acid molecule can contain appropriate translational expression control elements.

In many of the embodiments described herein, the vectors can contain an origin of replication. However, it should be understood that the methods and compositions can work with vectors that do not comprise an origin of replication, e.g., vectors that integrate into a nucleic acid, e.g., the genome, of a host following appropriate introduction into the host. Any such vector known to one skilled in the art without limitation can be used in the methods, compositions, and kits.

6.4 KITS FOR ONE-STEP TOPOISOMERASE CLONING

Further provided are kits for one-step topoisomerase cloning. In certain embodiments, the kit comprises a vector that will support one-step topoisomerase cloning, a nicking agent and a sequence-specific topoisomerase. In certain embodiments, the kits comprise one or more (e.g., 1, 2, 3, 4, 5, 6, 7, 8, 9, 10, etc.) reagents useful for performing a method as described herein. In one embodiment, the kit comprises a nucleic acid, e.g., a vector, suitable for use in a method as described herein. One or more topoisomerases, which can be the same or different, also can be a component of the kit. The nucleic acid in the kit can, but need not be a vector, and can contain one or more (e.g., 1, 2, 3, 4, 5, 6, 7, 8, 9, 10, etc.) expression control elements. In certain embodiments, the kit comprises instructions for using kit components.

A kit also can include a plurality of second nucleic acid molecules, wherein each nucleic acid molecule in the plurality has a first blunt end, and wherein the first blunt end includes a 5' nucleotide sequence complementary to a 5' overhang of the first nucleic acid molecule, e.g., the vector. The second nucleic acid molecules in the plurality can encode a plurality of transcriptional regulatory elements, translational regulatory elements, or a combination thereof, or can encode a plurality of peptides such as peptide tags, cell compartmentalization domains, and the like.

A nucleic acid molecule component of a kit can be, for example, a circularized or linearized vector such as a cloning vector or expression vector. If desired, such a kit can contain a plurality of nucleic acid molecules, each comprising a different expression control element or other element such as, but not limited to, a sequence encoding a tag or other detectable molecule or a cell compartmentalization domain. The different elements can be different types of a particular expression control element, for example, constitutive or inducible promoters or tissue specific promoters, or can be different types of elements including, for example, transcriptional and translational expression control elements, epitope tags, and the like. Such nucleic acid molecules may be topoisomerase-activated or can be activated with topoisomerase, and contain 5' overhanging sequences, or sequences that become 5' overhanging sequences after topoisomerase activation. In addition, the plurality of nucleic acid molecules can have 5' overhanging sequences that are unique to a particular expression control element, or that are common to plurality of related expression control elements, for example, to a plurality of different promoter elements. The 5' overhanging sequences of nucleic acid molecules can be designed such that one or more expression control elements contained on the nucleic acid molecule can be operatively directionally linked to provide a useful function, for example, an element comprising a Kozak sequence and an element comprising a translation start site can have complementary 5' overhangs such that the elements can be operatively linked as described herein.

Further provided are kits for linking nucleic acid molecules using methods described herein. Thus, kits may comprise one or more components for performing methods described herein. In particular embodiments, the kits may comprise one or more component selected from the group consisting of instructions for use of kits components, one or more buffers, one or more nucleic acid molecules (e.g., one or more nucleic acid molecules having a 5' overhang, a 3' overhang, a 5' overhang and a 3' overhang, two 3' overhangs, two 5' overhangs, etc.), one or more topoisomerases, one or more ligase, one or more recombinase, one or more adapter linker for preparing molecules having a 5' overhang and/or a 3' overhang, and/or one or more containers in which to perform methods described herein. In certain embodiments, the kits comprise a buffer compatible with both a topoisomerase, for example, vaccina topoisomerase I and with a nicking agent, for example, the nicking endonuclease Nt.AlwI.

6.5 USES OF CLONED NUCLEIC ACIDS

A directionally or non-directionally linked recombinant nucleic acid molecule can be used for various purposes for which recombinant vectors containing a directionally or non-directionally inserted nucleic acid molecule are generally used. Thus, the directionally or non-directionally linked nucleic acid molecule can be used, for example, for expressing a polypeptide in a cell, for diagnosing or treating a pathologic condition, or the like. For administration to a living subject, the directionally or non-directionally linked recombinant nucleic acid molecule generally is formulated in a pharmaceutical composition suitable for administration to the subject. Thus, further provided are pharmaceutical compositions containing a directionally or non-directionally linked recombinant nucleic acid molecule generated as described herein and expression products of this nucleic acid molecule. As such, the nucleic acid molecule can be useful as a medicament for treating a subject suffering from a pathological condition.

Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition, which can be, for example, orally or parenterally such as intravenously, and by injection, intubation, or other such method known in the art. The pharmaceutical composition also can contain a second reagent such as a diagnostic reagent, nutritional substance, toxin, or therapeutic agent, for example, a cancer chemotherapeutic agent.

The recombinant nucleic acid molecule can be incorporated within an encapsulating material such as into an oil-in-water emulsion, a microemulsion, micelle, mixed micelle, liposome, microsphere or other polymer matrix (see, for example, Gregoriadis, Liposome Technology, Vol. 1 (CRC Press, Boca Raton, Fla. 1984); Fraley, et al., Trends Biochem. Sci., 6:77 (1981),). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212) are an example of such encapsulating materials particularly useful for preparing a pharmaceutical composition, and other "masked" liposomes similarly can be used, such liposomes extending the time that a nucleic acid molecule remains in the circulation. Cationic liposomes, for example, also can be modified with specific receptors or ligands (Morishita et al., J. Clin. Invest., 91:2580-2585 (1993)). The nucleic acid molecule also can be introduced into a cell by complexing it with an adenovirus-polylysine complex (see, for example, Michael et al., J. Biol. Chem. 268:6866-6869 (1993)). Such compositions can be particularly useful for introducing a nucleic acid molecule into a cell in vivo or in vitro, including ex vivo, wherein the cell containing the nucleic acid molecule is administered back to the subject (see U.S. Pat. No. 5,399,346). A nucleic acid molecule also can be introduced into a cell using a biolistic method (see, for example, Sykes and Johnston, supra, 1999).

Recombinant nucleic acid molecules generated as described herein can be linear or circular. However, a nucleic acid molecule that is generated as a linear molecule can be circularized, for example, where it is to be used as a plasmid or cosmid vector. In addition, a linear nucleic acid molecule can be further cloned into a vector, which can be a plasmid vector or a viral vector such as a bacteriophage, baculovirus, retrovirus, lentivirus, adenovirus, Vaccinia virus, semliki forest virus and adeno-associated virus vector, all of which are well known and can be purchased from commercial sources (Invitrogen Corp., La Jolla Calif.; Promega, Madison Wis.; Stratagene, La Jolla Calif.; GIBCO/BRL, Gaithersburg Md.). In certain embodiments, a cloned acid molecule generated as described herein contains a nick, which can be resolved, for example, by contacting the nicked recombinant nucleic acid molecule with a ligase. Such a nucleic acid molecule that is covalently linked in both strands can be used as a template for an amplification reaction such as PCR. As such, a large amount of the construct can be generated. Furthermore, an amplification reaction can provide an in vitro selection method for obtaining only a desired product, without obtaining partial reaction products. For example, a method can be used to generate a recombinant nucleic acid molecule comprising, operatively linked in a 5' to 3' orientation, a first nucleic acid molecule comprising a promoter, a second nucleic acid molecule comprising a coding region, and a third nucleic acid molecule comprising a polyadenylation signal, wherein the nicks in the generated recombinant nucleic acid molecule are ligated.

By selecting a PCR primer pair including a first primer complementary to a nucleotide sequence upstream of the promoter sequence, and a second primer complementary to a nucleotide sequence downstream of the polyadenylation signal, a functional amplification product comprising the promoter, coding region and polyadenylation signal can be generated. In contrast, partial reaction products that lack either the first nucleic acid molecule or third nucleic acid can not be amplified because either the first or second primer, respectively, will not hybridize to the partial product. In addition, a construct lacking the second nucleic acid molecule would not be generated due to the lack of complementarity of the 5' overhanging sequences of the first and third nucleic acid molecules. As such, further provided, in part, is a means to obtain a desired functional, optionally directionally linked, recombinant nucleic acid molecule.

The use of an amplification reaction such as PCR in such a manner further provides a means to screen a large number of nucleic acid molecules to identify constructs of interest. Since methods for utilizing PCR in automated high throughput analyses are routine and well known, it will be recognized that the methods described herein can be readily adapted to use in a high throughput system. Using such a system, a large number of constructs can be screened in parallel, and partial or incomplete reaction products can be identified and disposed of, thereby preventing a waste of time and expense that would otherwise be required to characterize the constructs or examine the functionality of the constructs in further experiments.

The methods can also be used to detectably label a nucleic acid molecule with a chemical or small organic or inorganic moiety such that the nucleic acid molecule is useful as a probe. For example, a first nucleic acid molecule, for example, a vector, which has a topoisomerase recognition site, or cleavage product thereof, at a 3' terminus, can have bound thereto a detectable moiety such as a biotin, which can be detected using avidin or streptavidin, a fluorescent compound (e.g., Cy3, Cy5, Fam, fluorescein, or rhodamine), a radionuclide (e.g., sulfur-35, technicium-99, phosphorus-32, or tritium), a paramagnetic spin label (e.g., carbon-13), a chemiluminescent compound, an epitope, for example a peptide epitope, which can be detected using an antibody that recognizes the epitope, or the like, such that, upon generating a recombinant nucleic acid molecule as described herein, the nucleic acid product will be labeled. Methods of detectably labeling a nucleic acid molecule with such moieties are well known in the art (see, for example, Hermanson, "Bioconjugate Techniques" (Academic Press 1996)). It should be recognized that such elements as disclosed herein or otherwise known in the art, including nucleic acid molecules encoding cell compartmentalization domains, or detectable labels or tags, or comprising transcriptional or translation expression control elements can be useful components of a kit as disclosed herein.

In embodiments involving a linking a third nucleic acid molecule to the insert nucleic acid, the methods can be used to directionally or non-directionally link the two nucleic acid molecules. The method typically is used to directionally link the second nucleic acid molecule and the third nucleic acid molecule. However, the method can be used to non-directionally link the third nucleic acid molecule and the second nucleic acid molecule in the following embodiments: 1) Where a second nucleotide sequence is present at or near the 5' terminus of the second end of the third nucleic acid molecule, that is capable of hybridizing to the 5' complementary nucleotide sequence at the second end of the second nucleic acid molecule; and 2) Where a nucleotide sequence is present at or near the 5' terminus of both the first end and the second end of the second nucleic acid molecule that is capable of hybridizing to the 5' overhang at the first end of the third nucleic acid molecule. In these embodiments involving non-directional linking, the second end of the third nucleic acid molecule and the second end of the second nucleic acid molecule can be either blunt, or include an overhang.

7. EXAMPLES

The following examples are intended to illustrate the methods, compositions, and kits disclosed herein and should not be construed as limiting in any way. Various equivalents will be apparent to one skilled in the art from the following examples; such equivalents are also contemplated to be part of the invention disclosed herein.

7.1 Example 1

One-Step Topoisomerase Cloning of Red Fluorescent Protein

A gene for red fluorescent protein under control of the β-lactamase promoter was amplified by the polymerase chain reaction. The oligonucleotides used to amplify the gene and promoter were not phosphorylated on their 5' base. This was used as a test insert DNA fragment. The sequence of the test fragment is provided as SEQ ID NO:2.

A DNA cloning vector was used that resembled the one shown schematically in FIG. 13. The sequence of the cloning cassette is provided as SEQ ID NO:1. The stuffer fragment of the cloning cassette contained the counter-selectable marker ccdB. This cloning vector also carried a gene conferring resistance to the antibiotic kanamycin, and a ColE1 origin of DNA replication. We prepared the vector in 4 alternative ways. (A: uncut) 2.5 μg of vector was incubated in 50 μl of 100 mM sodium chloride, 50 mM Tris-chloride, 10 mM magnesium chloride, 1 mM dithiothreitol (pH7.9 @ 25° C.) at 55° C. for 1 hour. (B: nicked) 2.5 μg of vector was incubated in 50 μl of 100 mM sodium chloride, 50 mM Tris-chloride, 10 mM magnesium chloride, 1 mM dithiothreitol (pH7.9 @ 25° C.) with 10 U Nt.BstNBI (from New England Biolabs) at 55° C. for 1 hour. (C: cut) 2.5 μg of vector was incubated in 50 μl of 100 mM sodium chloride, 50 mM Tris-chloride, 10 mM magnesium chloride, 1 mM dithiothreitol (pH7.9 @ 25° C.) with 10 U BsmBI (from New England Biolabs) at 55° C. for 1 hour. (D: cut & nicked) 2.5 μg of vector was incubated in 50 μl of 100 mM sodium chloride, 50 mM Tris-chloride, 10 mM magnesium chloride, 1 mM dithiothreitol (pH7.9 @ 25° C.) with 10 U BsmBI and 10 U Nt.BstNBI (from New England Biolabs) at 55° C. for 1 hour. Each reaction was terminated after 1 hour by the addition of 250 μl of Qiagen PB buffer. The digested vector DNA was purified by loading onto a Qiagen PCR purification column, washing according to the manufacturer's instructions and eluting in 60 μl of elution buffer (EB).

Eight reactions, each of 25 μl were set up. In each reaction one of the vector preparations was mixed with the red fluorescent protein gene test insert. Each 25 μl reaction contained 40 ng (~30 fmol) of vector DNA, 50 mM potassium acetate, 20 mM Tris-acetate, 10 mM magnesium acetate, 1 mM dithiothreitol (pH7.9 @ 25° C.) and 20 U of Vaccinia DNA Topoisomerase I (from Epicentre Biotechnologies). Reactions also contained either 100 ng (~300 fmol) of the test insert DNA fragment, or no additional DNA. A total of 8 reactions were performed, with each of the 4 vector preparations being tested both with and without the test insert DNA fragment. Reactions were incubated for 1 hour at 37° C., then 5 μl of each reaction was transformed into 50 μl of chemically competent TOP10 cells (genotype F-mcrA Δ(mrr-hsdRMS-mcrBC) Φ80lacZΔM15 ΔlacX74 recA1 araΔ139 Δ(ara-leu) 7697 galU galK rpsL (StrR) endA1 nupG) from Invitrogen. After a 1 hour recovery at 37° C. in 450 μl SOC medium, 100 μl of cells were plated onto LB agar plates containing 25 μg/ml kanamycin and incubated overnight at 37° C.

Vector Preparation

| Reaction | BsmBI cut | Nt.BstNBI cut | Insert | # Transformants |
|---|---|---|---|---|
| 1 | No | No | No | 10 |
| 2 | No | No | Yes | 6 |
| 3 | No | Yes | No | 29 |
| 4 | No | Yes | Yes | >400 |
| 5 | Yes | No | No | 10 |
| 6 | Yes | No | Yes | 7 |
| 7 | Yes | Yes | No | 46 |
| 8 | Yes | Yes | Yes | >1,000 |

Only reactions 4 and 8, in which the vector had been digested with the nicking enzyme Nt.BstNBI and was then incubated in the presence of insert DNA and vaccinia topoisomerase I resulted in significantly more transformants than vector without insert (samples 1, 3, 5 and 7). The transformation rate was somewhat improved when the stuffer fragment within the cloning cassette was cut twice with the restriction endonuclease BsmBI (sample 8).

Eight transformants from reaction 4 were picked, grown for 16 hours in LB+25 µg/ml kanamycin and plasmid prepared from the cultures. The sequences of the inserts were determined using an ABI 3730 sequencer. All 8 sequences were identical to the red fluorescent protein under control of the β-lactamase promoter that had been used as the test insert. Four of the inserts were found in one orientation with respect to the vector sequences, the other 4 were in the opposite orientation.

These results show that incubation of vector DNA, insert DNA and vaccinia topoisomerase I in a single tube results in the insert DNA becoming joined with the vector DNA in a way that leads to stable propagation as a plasmid in a host cell. For this to succeed it was necessary to nick the vector DNA in the DNA strand complementary to the topoisomerase cleavage sequence element (see FIG. 8), so that topoisomerase cleavage at the topoisomerase cleavage sequence element resulted in a blunt double stranded break (see FIG. 5).

7.2 Example 2

One-Step Topoisomerase Cloning of β-Lactamase

A gene for β-lactamase protein under control of the β-lactamase promoter was amplified by the polymerase chain reaction. The oligonucleotides used to amplify the gene and promoter were not phosphorylated on their 5' base. This was used as a test insert DNA fragment. The sequence is provided as SEQ ID NO:3.

Two different DNA cloning vectors were used, with cloning cassettes that resembled the one shown schematically in FIG. 12. The sequence of the cloning cassette is provided as SEQ ID NO:4. Note that the 6 bases to the 5' of each of the Topoisomerase cleavage sequence elements and the 4 bases to the 3' were chosen to be identical to those bases that flank a high affinity topoisomerase cleavage sequence in the plasmid pUC19. One of these cloning vectors (V1) also carried a gene conferring resistance to the antibiotic kanamycin, and a ColE1 origin of DNA replication. The other of these cloning vectors (V2) also carried genes conferring resistance to the antibiotics kanamycin, ampicillin, chloramphenicol and gentamycin and a ColE1 origin of DNA replication.

Each vector was prepared in 2 alternative ways.

A: (gel purified) 2.5 µg of vector was incubated in 50 µl of 100 mM sodium chloride, 50 mM Tris-chloride, 10 mM magnesium chloride, 1 mM dithiothreitol (pH7.9 @ 25° C.) with 20 U of restriction endonuclease BsaI at 50° C. for 1 hour. BsaI digestion released a stuffer fragment of ~660 bp which was separated from the vector DNA by agarose gel purification. The purified vector DNA was then incubated in 100 µl of 100 mM sodium chloride, 50 mM Tris-chloride, 10 mM magnesium chloride, 1 mM dithiothreitol (pH7.9 @ 25° C.) with 10 U of nicking endonuclease Nt.BstNBI at 55° C. for 1 hour. Each reaction was terminated after 1 hour by the addition of 250 µl of Qiagen PB buffer. The digested vector DNA was purified by loading onto a Qiagen PCR purification column, washing according to the manufacturer's instructions and eluting in 60 µl of elution buffer (EB).

B: (not gel purified) 2.5 µg of vector was incubated in 50 µl of 100 mM sodium chloride, 50 mM Tris-chloride, 10 mM magnesium chloride, 1 mM dithiothreitol (pH7.9 @ 25° C.) with 20 U of restriction endonuclease BsaI at 50° C. for 1 hour. Each reaction was terminated after 1 hour by the addition of 250 µl of Qiagen PB buffer. The digested vector DNA was purified by loading onto a Qiagen PCR purification column, washing according to the manufacturer's instructions and eluting in 60 µl of elution buffer (EB). BsaI digestion released a stuffer fragment of ~660 bp, but no effort was made to separate the released stuffer fragment from the vector DNA. The vector+stuffer DNA was then incubated in 100 µl of 100 mM sodium chloride, 50 mM Tris-chloride, 10 mM magnesium chloride, 1 mM dithiothreitol (pH7.9 @ 25° C.) with 10 U of nicking endonuclease Nt.BstNBI at 55° C. for 1 hour. Each reaction was terminated after 1 hour by the addition of 250 µl of Qiagen PB buffer. The digested vector DNA was purified by loading onto a Qiagen PCR purification column, washing according to the manufacturer's instructions and eluting in 60 µl of elution buffer (EB).

Eight reactions, each of 10 µl were set up. In each reaction one of the vector preparations was mixed with the β-lactamase gene test insert. Each 10 µl reaction contained 12.5 ng (~10 fmol) of vector DNA, 50 mM potassium acetate, 20 mM Tris-acetate, 10 mM magnesium acetate, 1 mM dithiothreitol (pH7.9 @ 25° C.) and 10 U of Vaccinia DNA Topoisomerase I (from Epicentre Biotechnologies). Reactions also contained either 50 ng (~80 fmol) of the test insert DNA fragment, or no additional DNA. Reactions were incubated for 1 hour at 37° C., then 2.5 µl of each reaction was transformed into 25 µl of chemically competent TOP10 cells (genotype F-mcrA Δ(mrr-hsdRMS-mcrBC) Φ80lacZΔM15 ΔlacX74 recA1 araΔ139 Δ(ara-leu)7697 galU galK rpsL (StrR) endA1 nupG) from Invitrogen. After a 1 hour recovery at 37° C. in 150 µl SOC medium, all of the transformed and recovered cells were plated onto LB agar plates containing 25 µg/ml kanamycin and incubated overnight at 37° C.

| Reaction | Vector | Gel purified | Insert | # Transformants |
|---|---|---|---|---|
| 1 | V1 | Yes | Yes | >10,000 |
| 2 | V2 | Yes | Yes | >5,000 |
| 3 | V1 | No | Yes | >5,000 |
| 4 | V2 | No | Yes | >2,000 |
| 5 | V1 | Yes | No | 34 |
| 6 | V2 | Yes | No | 8 |
| 7 | V1 | No | No | 6 |
| 8 | V2 | No | No | 1 |

These results show that incubation of vector DNA, insert DNA and vaccinia topoisomerase I in a single tube results in the insert DNA becoming joined with the vector DNA in a way that leads to stable propagation as a plasmid in a host cell. If the vector stuffer fragment is cleaved, there is little effect of removing the stuffer by gel purification.

7.3 Example 3

Time Course for Topoisomerase Cloning of β-Lactamase

A gene for β-lactamase protein under control of the β-lactamase promoter was amplified by the polymerase chain reaction. The oligonucleotides used to amplify the gene and promoter were not phosphorylated on their 5' base. This was used as a test insert DNA fragment. The sequence is provided as SEQ ID NO:3.

One DNA cloning vectors were used, with a cloning cassette that resembled the one shown schematically in FIG. 12. The sequence of the cloning cassette is provided as SEQ ID NO:4. The cloning vector also carried a gene conferring resistance to the antibiotic kanamycin, and a ColE1 origin of DNA replication.

We prepared the vector as follows: 2.5 μg of vector was incubated in 50 μl of 100 mM sodium chloride, 50 mM Tris-chloride, 10 mM magnesium chloride, 1 mM dithiothreitol (pH7.9 @ 25° C.) with 20 U of restriction endonuclease BsaI at 50° C. for 1 hour. The reaction was terminated after 1 hour by the addition of 250 μl of Qiagen PB buffer. The digested vector DNA was purified by loading onto a Qiagen PCR purification column, washing according to the manufacturer's instructions and eluting in 60 μl of elution buffer (EB). The eluted DNA was then incubated in 100 μl of 100 mM sodium chloride, 50 mM Tris-chloride, 10 mM magnesium chloride, 1 mM dithiothreitol (pH7.9 @ 25° C.) with 10 U of nicking endonuclease Nt.BstNBI at 55° C. for 1 hour. The reaction was terminated after 1 hour by the addition of 250 μl of Qiagen PB buffer. The digested vector DNA was purified by loading onto a Qiagen PCR purification column, washing according to the manufacturer's instructions and eluting in 60 μl of elution buffer (EB).

Five reactions, each of 10 μl were set up. Each reaction contained 12.5 ng (~10 fmol) of vector DNA, 50 mM potassium acetate, 20 mM Tris-acetate, 10 mM magnesium acetate, 1 mM dithiothreitol (pH7.9 @ 25° C.) and 10 U of Vaccinia DNA Topoisomerase I (from Epicentre Biotechnologies). Reactions also contained 50 ng (~80 fmol) of the test insert DNA fragment.

Reactions were incubated for various times at 37° C., then 2.5 μl of each reaction was transformed into 25 μl of chemically competent TOP10 cells (genotype F-mcrA Δ(mrr-hsdRMS-mcrBC) Φ80lacZΔM15 ΔlacX74 recA1 araΔ139 Δ(ara-leu)7697 galU galK rpsL (StrR) endA1 nupG) from Invitrogen. After a 1 hour recovery at 37° C. in 150 μl SOC medium, all of the transformed and recovered cells were plated onto LB agar plates containing 25 μg/ml kanamycin and incubated overnight at 37° C.

| Reaction | Incubation time (minutes) | # Transformants |
|---|---|---|
| 1 | 0 | 10 |
| 2 | 5 | ~500 |
| 3 | 15 | ~2,000 |
| 4 | 30 | ~5,000 |
| 5 | 60 | >10,000 |

These results show that incubation of vector DNA, insert DNA and vaccinia topoisomerase I in a single tube results in the insert DNA becoming joined with the vector DNA in a way that leads to stable propagation as a plasmid in a host cell. A suitable number of transformants may be obtained after a 5 minute incubation.

7.4 Example 4

Effect of Reaction Component Concentrations for Topoisomerase Cloning of β-Lactamase A gene for β-lactamase protein under control of the β-lactamase promoter was amplified by the polymerase chain reaction. The oligonucleotides used to amplify the gene and promoter were not phosphorylated on their 5' base. This was used as a test insert DNA fragment. The sequence is provided as SEQ ID NO:3.

One DNA cloning vectors was used, with a cloning cassette that resembled the one shown schematically in FIG. 12. The sequence of the cloning cassette is provided as SEQ ID NO:4. The cloning vector also carried a gene conferring resistance to the antibiotic kanamycin, and a ColE1 origin of DNA replication.

The vector was prepared as follows: 2.5 μg of vector was incubated in 50 μl of 100 mM sodium chloride, 50 mM Tris-chloride, 10 mM magnesium chloride, 1 mM dithiothreitol (pH7.9 @ 25° C.) with 20 U of restriction endonuclease BsaI at 50° C. for 1 hour. The reaction was terminated after 1 hour by the addition of 250 μl of Qiagen PB buffer. The digested vector DNA was purified by loading onto a Qiagen PCR purification column, washing according to the manufacturer's instructions and eluting in 60 μl of elution buffer (EB). The eluted DNA was then incubated in 100 μl of 100 mM sodium chloride, 50 mM Tris-chloride, 10 mM magnesium chloride, 1 mM dithiothreitol (pH7.9 @ 25° C.) with 10 U of nicking endonuclease Nt.BstNBI at 55° C. for 1 hour. The reaction was terminated after 1 hour by the addition of 250 μl of Qiagen PB buffer. The digested vector DNA was purified by loading onto a Qiagen PCR purification column, washing according to the manufacturer's instructions and eluting in 60 μl of elution buffer (EB).

Ten reactions, each of 10 μl were set up. Each reaction contained 50 mM potassium acetate, 20 mM Tris-acetate, 10 mM magnesium acetate and 1 mM dithiothreitol (pH7.9 @ 25° C.) and 10 ng (~16 fmol) test insert DNA. Reactions also contained either 10, 3 or 1 ng (~8, 2.7 or 0.8 fmol) of vector DNA and 10, 5, 2.5 or 0 U of Vaccinia DNA Topoisomerase I (from Epicentre Biotechnologies).

Reactions were incubated for 30 minutes at 37° C., then 2.5 μl of each reaction was transformed into 25 μl of chemically competent TOP10 cells (genotype F-mcrA Δ(mrr-hsdRMS-mcrBC) Φ80lacZΔM15 ΔlacX74 recA1 araΔ139 Δ(ara-leu) 7697 galU galK rpsL (StrR) endA1 nupG) from Invitrogen. After a 1 hour recovery at 37° C. in 150 μl SOC medium, all of the transformed and recovered cells were plated onto LB agar plates containing 25 μg/ml kanamycin and incubated overnight at 37° C.

| Reaction | Vector concentration (μg/ml) | Topoisomerase concentration (U/ml) | # Transformants |
|---|---|---|---|
| 1 | 1 | 1,000 | ~700 |
| 2 | 1 | 500 | ~500 |
| 3 | 1 | 250 | 170 |
| 4 | 1 | 0 | 10 |
| 5 | 0.5 | 1,000 | 252 |
| 6 | 0.5 | 500 | 380 |
| 7 | 0.5 | 250 | ~500 |
| 8 | 0.25 | 1,000 | 95 |
| 9 | 0.25 | 500 | 224 |
| 10 | 0.25 | 250 | 328 |

These results show that incubation of vector DNA, insert DNA and vaccinia topoisomerase I in a single tube results in the insert DNA becoming joined with the vector DNA in a way that leads to stable propagation as a plasmid in a host cell.

7.5 Example 5

Directional Cloning Directed by 2, 4 or 6 Base Overhangs

A 445 bp gene (The sequence is provided as SEQ ID NO:4) was amplified by the polymerase chain reaction. The oligonucleotides used to amplify the gene and promoter were not phosphorylated on their 5' base. Three different "forward" primers were used to amplify the gene: in addition to the bases identical to the 5' end of the gene, one of these forward primers had 6 additional bases at its 5' end (GACTGA), one had 4 additional bases at its 5' end (GACT), and one had 2 additional bases at its 5' end (GA). These 3 inserts ("+6", "+4", and "+2") were used as test inserts.

Three DNA cloning vectors were used, with cloning cassettes that resembled those shown schematically in FIGS. 9, 10 and 11; the sequences of the cloning cassettes are provided as SEQ ID NO:6, SEQ ID NO:7 and SEQ ID NO:8 respectively. The cloning vector also carried a gene conferring resistance to the antibiotic kanamycin, and a ColE1 origin of DNA replication.

We prepared the vector as follows: 2 µg of each vector (SEQ ID NOS:6, 7, and 8, respectively) were incubated in 100 µl of 100 mM sodium chloride, 50 mM Tris-chloride, 10 mM magnesium chloride, 1 mM dithiothreitol (pH7.9 @ 25° C.) with 10 U of nicking endonuclease Nt.BstNBI at 55° C. for 1 hour. The reactions were terminated after 1 hour by the addition of 500 µl of Qiagen PB buffer. The digested vector DNAs were purified by loading onto Qiagen PCR purification columns, washing according to the manufacturer's instructions and eluting in 100 µl of elution buffer (EB).

Nine reactions, each of 10 µl were set up. Each reaction contained 50 mM potassium acetate, 20 mM Tris-acetate, 10 mM magnesium acetate and 1 mM dithiothreitol (pH7.9 @ 25° C.) and 50 ng (~160 fmol) test insert DNA (three reactions each of the +6, +4 or +2 inserts). Reactions also contained 20 ng (~15 fmol) of vector DNA: for the +6 insert, the vector containing cloning cassette SEQ ID NO:6 was used; for the +4 insert, the vector containing cloning cassette SEQ ID NO:7 was used; for the +2 insert, the vector containing cloning cassette SEQ ID NO:8 was used. To one reaction for each insert-vector pair was added 2.5 U Vaccinia DNA Topoisomerase I (from Epicentre Biotechnologies). To a second reaction for each insert-vector pair was added 5.8 ng (~70 fmol) of a fusion protein between maltose binding protein and Vaccinia DNA Topoisomerase I (the sequence of the protein is shown as SEQ ID NO:9). No topoisomerase was added to the third reaction for each vector-insert pair.

Reactions were incubated for 30 minutes at 37° C., then 2.5 µl of each reaction was transformed into 25 µl of chemically competent TOP10 cells (genotype F-mcrA Δ(mrr-hsdRMS-mcrBC) Φ80lacZΔM15 ΔlacX74 recA1 araΔ139 Δ(ara-leu) 7697 galU galK rpsL (StrR) endA1 nupG) from Invitrogen. After a 1 hour recovery at 37° C. in 150 µl SOC medium, all of the transformed and recovered cells were plated onto LB agar plates containing 25 µg/ml kanamycin and incubated overnight at 37° C.

| Reaction | Vector | Insert | Topoisomerase | # Transformants |
|---|---|---|---|---|
| 1 | SEQ ID NO: 6 | +6 | 2.5 U Epicenter topoisomerase | 100 |
| 2 | SEQ ID NO: 6 | +6 | 5.8 ng MBP-topoisomerase fusion | 246 |
| 3 | SEQ ID NO: 6 | +6 | none | 64 |
| 4 | SEQ ID NO: 7 | +4 | 2.5 U Epicenter topoisomerase | 158 |
| 5 | SEQ ID NO: 7 | +4 | 5.8 ng MBP-topoisomerase fusion | ~500 |
| 6 | SEQ ID NO: 7 | +4 | none | 18 |
| 7 | SEQ ID NO: 8 | +2 | 2.5 U Epicenter topoisomerase | 86 |
| 8 | SEQ ID NO: 8 | +2 | 5.8 ng MBP-topoisomerase fusion | ~1,000 |
| 9 | SEQ ID NO: 8 | +2 | none | 2 |

Eight transformants from each of reactions 2, 5 and 8 were picked, grown for 16 hours in LB+25 µg/ml kanamycin and plasmid prepared from the cultures. The sequences of the inserts were determined using an ABI 3730 sequencer.

Four of 8 clones picked from reaction 2 had sequences identical to the test gene sequence (SEQ ID NO:4) with the addition of 6 bases (GACTGA) at the 5' end, the other 4 had sequences of the cloning cassette SEQ ID NO:6. Of the 4 clones that contained the test gene sequence, all 4 were oriented such that the 6 additional bases were located at the same position as the 6 base overhang in the vector. That is the insert was found to have been cloned only in the direction guided by the overhang in the vector.

Four of 8 clones picked from reaction 5 had sequences identical to the test gene sequence (SEQ ID NO:4) with the addition of 4 bases (GACT) at the 5' end, the other 4 had sequences of the cloning cassette SEQ ID NO:7. Of the 4 clones that contained the test gene sequence, all 4 were oriented such that the 4 additional bases were located at the same position as the 4 base overhang in the vector. That is the insert was found to have been cloned only in the direction guided by the overhang in the vector.

Seven of 8 clones picked from reaction 8 had sequences identical to the test gene sequence (SEQ ID NO:4) with the addition of 2 bases (GA) at the 5' end, the other 1 had sequences of the cloning cassette SEQ ID NO:7. Of the 7 clones that contained the test gene sequence, all 7 were oriented such that the 2 additional bases were located at the same position as the 2 base overhang in the vector. That is the insert was found to have been cloned only in the direction guided by the overhang in the vector.

These results show that inserts may be cloned in a specific direction into the cloning cassette by positioning the nicking agent recognition site such that a nick is produced at one end offset from the position of the topoisomerase cleavage site. A 5' overhang in the vector that results from nicking the vector and treating with topoisomerase, that is as short as 2 bp, is sufficient to completely specify the cloning direction of an insert that begins with a sequence complementary to the overhang.

7.6 Example 6

Use of a Fusion Between Maltose Binding Protein and Vaccinia Topoisomerase I for Topoisomerase Cloning The aim of this example was to test the suitability of a protein that was a fusion between maltose binding protein and vaccinia topoisomerase I to catalyze cloning.

A gene for β-lactamase protein under control of the β-lactamase promoter was amplified by the polymerase chain reaction. The oligonucleotides used to amplify the gene and promoter were not phosphorylated on their 5' base. This was used as a test insert DNA fragment. The sequence is provided as SEQ ID NO:3.

One DNA cloning vector was used, with a cloning cassette that resembled the one shown schematically in FIG. 12. The sequence of the cloning cassette is provided as SEQ ID NO:4. The cloning vector also carried a gene conferring resistance to the antibiotic kanamycin, and a ColE1 origin of DNA replication.

We prepared the vector as follows: 2.5 µg of vector was incubated in 50 µl of 100 mM sodium chloride, 50 mM Tris-chloride, 10 mM magnesium chloride, 1 mM dithiothreitol (pH7.9 @ 25° C.) with 20 U of restriction endonuclease BsaI at 50° C. for 1 hour. The reaction was terminated after 1 hour by the addition of 250 µl of Qiagen PB buffer. The digested vector DNA was purified by loading onto a Qiagen PCR purification column, washing according to the manufacturer's instructions and eluting in 60 µl of elution buffer (EB). The eluted DNA was then incubated in 100 µl of 100 mM sodium chloride, 50 mM Tris-chloride, 10 mM magnesium chloride, 1 mM dithiothreitol (pH7.9 @ 25° C.) with 10 U of nicking endonuclease Nt.BstNBI at 55° C. for 1 hour. The reaction was terminated after 1 hour by the addition of 250 µl of Qiagen PB buffer. The digested vector DNA was purified by loading onto a Qiagen PCR purification column, washing according to the manufacturer's instructions and eluting in 60 µl of elution buffer (EB).

Ten reactions, each of 10 µl were set up. Each reaction contained 50 mM potassium acetate, 20 mM Tris-acetate, 10 mM magnesium acetate and 1 mM dithiothreitol (pH7.9 @ 25° C.) and 50 ng (~80 fmol) test insert DNA. Reactions also contained 4 ng (~2.5 fmol) of vector DNA. Reactions contained different preparations of topoisomerase enzyme.

One reaction contained 2.5 U of Vaccinia DNA Topoisomerase I (from Epicentre Biotechnologies). Other reactions contained either 2.9 µg (~37 pmol), 725 ng (~9.3 pmol), 181 ng (~2.3 pmol), 45 ng (~570 pmol), 11 ng (~144 fmol), 2.8 ng (~36 fmol), 0.7 ng (~9 fmol) or 0.17 ng (~2 fmol) of a fusion between maltose binding protein and Vaccinia DNA Topoisomerase I, the amino acid sequence of this protein is provided as SEQ ID NO:9. One reaction contained no topoisomerase.

Reactions were incubated for 30 minutes at 37° C., then 2.5 µl of each reaction was transformed into 25 µl of chemically competent TOP10 cells (genotype F-mcrA Δ(mrr-hsdRMS-mcrBC) Φ80lacZΔM15 ΔlacX74 recA1 araΔ139 Δ(ara-leu)7697 galU galK rpsL (StrR) endA1 nupG) from Invitrogen. After a 1 hour recovery at 37° C. in 150 µl SOC medium, all of the transformed and recovered cells were plated onto LB agar plates containing 25 µg/ml kanamycin and incubated overnight at 37° C.

| Reaction | MBP-Topoisomerase concentration (µg/ml) | Epicenter Topoisomerase concentration (U/ml) | # Transformants |
|---|---|---|---|
| 1 | 290 | 0 | 38 |
| 2 | 73 | 0 | 65 |
| 3 | 18 | 0 | 36 |
| 4 | 4.5 | 0 | 223 |
| 5 | 1.1 | 0 | ~4,000 |
| 6 | 0.28 | 0 | ~3,000 |
| 7 | 0.07 | 0 | 96 |
| 8 | 0.02 | 0 | 18 |
| 9 | 0 | 250 | 120 |
| 10 | 0 | 0 | 2 |

These results show that a protein that is a fusion of maltose binding protein with vaccinia topoisomerase I can catalyze the cloning of insert DNA.

7.7 Example 7

One-Step Topoisomerase Cloning by Simultaneous Action of Nicking Endonuclease and Topoisomerase The aim of this example was to clone an insert DNA by incubating with vector DNA, nicking endonuclease and topoisomerase in a single reaction.

A 445 bp gene (The sequence is provided as SEQ ID NO:4) was amplified by the polymerase chain reaction. The oligonucleotides used to amplify the gene and promoter were not phosphorylated on their 5' base.

One DNA cloning vector was used, with a cloning cassette that resembled the one shown schematically in FIG. 14. The sequence of the cloning cassette is provided as SEQ ID NO:10. The cloning vector also carried a gene conferring resistance to the antibiotic kanamycin, and a ColE1 origin of DNA replication.

The vector DNA was grown in and purified from SCS110 cells (genotype rpsL (Str$^J$) thr leu endA thi-1 lacY galK galT ara tonA tsx dam dcm supE44 Δ(lac-proAB) [F' traD36 proAB lacIqZΔM15], because Nt.AlwI nicking is blocked by dam methylation or overlapping dcm methylation.

In one reaction, nicked vector DNA was used. Vector DNA was nicked by treating 2.5 µg of vector in 100 µl of 50 mM potassium acetate, 20 mM Tris-acetate, 10 mM magnesium acetate, 1 mM dithiothreitol (pH7.9 @ 25° C.) with 10 U of Nt.AlwI for 1 hour at 37° C. The reaction was terminated after 1 hour by the addition of 500 µl of Qiagen PB buffer. The nicked vector DNA was purified by loading onto a Qiagen PCR purification column, washing according to the manufacturer's instructions and eluting in 100 µl of elution buffer (EB).

Five reactions, each of 10 µl were set up. Each 10 µl reaction contained 50 mM potassium acetate, 20 mM Tris-acetate, 10 mM magnesium acetate, 1 mM dithiothreitol (pH7.9 @ 25° C.), 40 ng (~130 fmol) of the test insert DNA fragment, 2.5 U of Vaccinia DNA Topoisomerase I (from Epicentre Biotechnologies) and either 2.5 ng (~2 fmol) of pre-nicked vector DNA or 95 ng (~75 fmol) of vector DNA that had not been pre-nicked. Reactions with un-nicked vector DNA also contained either 10, 5 or 2.5 U of Nt.AlwI. Reactions were incubated for 30 minutes at 37° C., then 2.5 µl of each reaction was transformed into 25 µl of chemically competent DH10B cells [genotype: F⁻ mcrA Δ(mrr-hsdRMS-mcrBC) φ80dlacZΔM15 ΔlacX74 deoR recA1 araD139 Δ(ara leu)7697 galU galK rpsL endA1 nupG] from Invitrogen. After a 1 hour recovery at 37° C. in 150 µl SOC medium, all of the transformed and recovered cells were plated onto LB agar plates containing 25 µg/ml kanamycin and incubated overnight at 37° C.

| Reaction | Vector (un-nicked) | Vector (pre-nicked) | Nt.AlwI | # Transformants |
|---|---|---|---|---|
| 1 | 95 ng | 0 | 0 | 0 |
| 2 | 95 ng | 0 | 10 U | 0 |
| 3 | 95 ng | 0 | 5 U | 0 |
| 4 | 95 ng | 0 | 2.5 U | 10 |
| 5 | 0 | 2.5 ng | 0 | 379 |

Ten transformants from reaction 4 were picked, grown for 16 hours in LB+25 µg/ml kanamycin and plasmid prepared from the cultures. The sequences of the inserts were determined using an ABI 3730 sequencer. Eight out of ten inserts had the correct sequence, sequencing reactions failed for the other two clones.

These results show that incubation of vector DNA, insert DNA, vaccinia topoisomerase I and nicking agent in a single tube results in the insert DNA becoming joined with the vector DNA in a way that leads to stable propagation as a plasmid in a host cell.

7.8 Example 8

One-Step Topoisomerase Cloning by Simultaneous Action of Nicking Endonuclease and Topoisomerase The aim of this example was to clone an insert DNA by incubating with vector DNA, nicking endonuclease and topoisomerase in a single reaction.

A 445 bp gene (The sequence is provided as SEQ ID NO:4) was amplified by the polymerase chain reaction. The oligonucleotides used to amplify the gene and promoter were not phosphorylated on their 5' base.

One DNA cloning vector was used, with a cloning cassette that resembled the one shown schematically in FIG. 14. The sequence of the cloning cassette is provided as SEQ ID NO:10. The cloning vector also carried a gene conferring resistance to the antibiotic kanamycin, and a ColE1 origin of DNA replication.

The vector DNA was grown in and purified from SCS110 cells (genotype rpsL (Str$^r$) thr leu endA thi-1 lacY galK galT ara tonA tsx dam dcm supE44 Δ(lac-proAB) [F' traD36 proAB lacIqZΔM15], because Nt.AlwI nicking is blocked by dam methylation or overlapping dcm methylation.

In one reaction, nicked vector DNA was used. Vector DNA was nicked by treating 2.5 µg of vector in 100 µl of 50 mM potassium acetate, 20 mM Tris-acetate, 10 mM magnesium acetate, 1 mM dithiothreitol (pH7.9 @ 25° C.) with 10 U of Nt.AlwI for 1 hour at 37° C. The reaction was terminated after 1 hour by the addition of 500 µl of Qiagen PB buffer. The nicked vector DNA was purified by loading onto a Qiagen PCR purification column, washing according to the manufacturer's instructions and eluting in 100 µl of elution buffer (EB).

Eight reactions, each of 10 µl were set up. Each 10 µl reaction contained 50 mM potassium acetate, 20 mM Tris-acetate, 10 mM magnesium acetate, 1 mM dithiothreitol (pH7.9 @ 25° C.), and either 2.5 ng (~2 fmol) of pre-nicked vector DNA or 95 ng (~75 fmol) of vector DNA that had not been pre-nicked and 16 ng (~200 fmol) of a fusion between maltose binding protein and Vaccinia DNA Topoisomerase I, the amino acid sequence of this protein is provided as SEQ ID NO:9. Reactions with un-nicked vector DNA also contained either 5, 2.5, 12.5, 0.63, 0.31 or 0.15 U of Nt.AlwI. Reactions were incubated for either 30 minutes or 1 hour at 37° C., then 2.5 µl of each reaction was transformed into 25 µl of chemically competent DH10B cells [genotype: F⁻ mcrA Δ(mrr-hsdRMS-mcrBC) φ80dlacZΔM15 ΔlacX74 deoR recA1 araD139 Δ(ara leu)7697 galU galK rpsL endA1 nupG] from Invitrogen. After a 1 hour recovery at 37° C. in 150 µl SOC medium, all of the transformed and recovered cells were plated onto LB agar plates containing 25 µg/ml kanamycin and incubated overnight at 37° C.

| Reaction | Vector (un-nicked) | Vector (pre-nicked) | Nt.AlwI | # Transformants (30 minutes) | # Transformants (60 minutes) |
|---|---|---|---|---|---|
| 1 | 95 ng | 0 | 0 | 4 | 9 |
| 2 | 95 ng | 0 | 5 U | 0 | 0 |
| 3 | 95 ng | 0 | 2.5 U | 110 | 248 |
| 4 | 95 ng | 0 | 1.25 U | 252 | 326 |
| 5 | 95 ng | 0 | 0.63 U | 261 | 563 |
| 6 | 95 ng | 0 | 0.31 U | 186 | 361 |
| 7 | 95 ng | 0 | 0.15 U | 58 | 120 |
| 8 | 0 | 2.5 ng | 0 | ~300 | >1,000 |

Ten transformants from reaction 4 were picked, grown for 16 hours in LB+25 µg/ml kanamycin and plasmid prepared from the cultures. The sequences of the inserts were determined using an ABI 3730 sequencer. Eight out of ten inserts had the correct sequence, sequencing reactions failed for the other two clones.

These results show that incubation of vector DNA, insert DNA, a fusion between maltose binding protein and vaccinia topoisomerase I and nicking agent in a single tube results in the insert DNA becoming joined with the vector DNA in a way that leads to stable propagation as a plasmid in a host cell.

SEQUENCES

SEQ ID NO: 1 (vector cloning cassette)
```
GGGGCCCTTAGCTGACTCTATAGGGAAGTTCCTATTCTCTAGAAAGTATAGGAACTTCTGAA
GGGGGAGAGACGACGCCGCGTGGATCCGGCTTACTAAAAGCCAGATAACAGTATGCGTATT
TGCGCGCTGATTTTTGCGGTATAAGAATATATACTGATATGTATACCCGAAGTATGTCAAAA
AGAGGTATGCTATGAAGCAGCGTATTACAGTGACAGTTGACAGCGACAGCTATCAGTTGCTC
AAGGCATATATGATGTCAATATCTCCGGTCTGGTAAGCACAACCATGCAGAATGAAGCCCGT
CGTCTGCGTGCCGAACGCTGGAAAGCGGAAAATCAGGAAGGGATGGCTGAGGTCGCCCGGTT
TATTGAAATGAACGGCTCTTTTGCTGACGAGAACAGGGGCTGGTGAAATGCAGTTTAAGGTT
TACACCTATAAAAGAGAGCCGTTATCGTCTGTTTGTGGATGTACAGAGTGATATTATTGA
CACGCCCGGGCGACGGATGGTGATCCCCCTGGCCAGTGCACGTCTGCTGTCAGATAAAGTCT
CCCGTGAACTTTACCCGGTGGTGCATATCGGGGATGAAAGCTGGCGCATGATGACCACCGAT
ATGGCCAGTGTGCCGGTTTCCGTTATCGGGGAAGAAGTGGCTGATCTCAGCCACCGCGAAAA
TGACATCAAAAACGCCATTAACCTGATGTTCTGGGGAATATAAGGTCTCCGAGCGGTATCAG
CTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGCGCTCTCCTGTT
```

CCGACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCC
AACCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGGCTAACTACGGCTACACTAGAA
GAACAGTATTTGGTATCTGCGCTCTGCTGAAGCCAGTTACCTTCGGAAAAAGAGTTGGTAGC
TCTTGATCCGGCAAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGGGGTCTGACGCTC
AGTGGAACGACGCGCGTAACTCACGTTAAGGGATTTTGGTCATGAGCGTCTCCAAATGA
AGGGAAGTTCCTATACTTTCTAGAGAATAGGAACTTCTATAGGGAGTCAGCTAAGGGAAAA

SEQ ID NO: 2 (RFP test fragment)
GGTGTTAGGAGGAAAAAAAAATGGTTTCCAAGGGCGAGGAGGATAACATGGCTATCATTAAA
GAGTTCATGCGCTTCAAAGTTCACATGGAGGGTTCTGTTAACGGTCACGAGTTCGAGATCGA
AGGCGAAGGCGAGGGCCGTCCGTATGAAGGCACCCAGACCGCCAAACTGAAAGTGACTAAAG
GCGGCCCGCTGCCTTTTGCGTGGGACATCCTGAGCCCGCAATTTATGTACGGTTCTAAAGCT
TATGTTAAACACCCAGCGGATATCCCGGACTATCTGAAGCTGTCTTTTCCGGAAGGTTTCAA
GTGGGAACGCGTAATGAATTTTGAAGATGGTGGTGTCGTGACCGTCACTCAGGACTCCTCCC
TGCAGGATGGCGAGTTCATCTATAAAGTTAAACTGCGTGGTACTAATTTTCCATCTGATGGC
CCGGTGATGCAGAAGAAGACGATGGGTTGGGAGGCGTCTAGCGAACGCATGTATCCGGAAGA
TGGTGCGCTGAAAGGCGAAATTAAACAGCGCCTGAAACTGAAAGATGGCGGCCATTATGACG
CTGAAGTGAAAACCACGTACAAAGCCAAGAAACCTGTGCAGCTGCCTGGCGCGTACAATGTG
AATATTAAACTGGACATCACCTCTCATAATGAAGATTATACGATCGTAGAGCAATATGAGCG
CGCGGAGGGTCGTCATTCTACCGGTGGCATGGATGAGCTGTACAAATAA SEQ ID NO: 3 (beta lactamase test fragment)
ATAACTTCGTATAGCATACATTATACGAACGGTATCAGAATTGGTTAATTGGTTGTAACACT
GACCCCTATTTGTTTATTTTTCTAAATACATTCAAATATGTATCCGCTCATGAGACAATAAC
CCTGATAAATGCTTCAATAATATTGAAAAAGGAAGAATATGAGTATTCAACATTTCCGTGTC
GCCCTTATTCCCTTTTTTGCGGCATTTTGCCTTCCTGTTTTTGCTCACCCAGAAACGCTGGT
GAAAGTAAAAGATGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATGATGAGCACTTTT
AAAGTTCTGCTATGTGGCGCGGTATTATCCCGTATTGACGCCGGGCAAGAGCAACTCGGTCG
CCGCATACACTATTCTCAGAATGACTTGGTTGAGTACTCACCAGTCACAGAAAAGCATCTTA
CGGATGGCATGACAGTAAGAGAATTATGCAGTGCTGCCATAACCATGAGTGATAACACTGCG
GCCAACTTACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCATACCAAACG
ACGAGCGTGACACCACGATGCCTGTAGCGATGGCAACAACGTTGCGCAAACTATTAACTGGC
GAACTACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCCGGAGCCG
GTGAGCGTGGTTCTCGCGGTATCATCGCAGCGCTGGGGCCAGATGGTAAGCCCTCCCGTATC
GTAGTTATCTACACGACGGGGAGTCAGGCAACTATGGATGAACGAAATAGACAGATCGCTGA
GATAGGTGCCTCACTGATTAAGCATTGGTAAATAACTTCGTATAGGATACTTTATACGAAGT
TAT SEQ ID NO: 4 (vector cloning cassette with pUC sites)
GGGGGTGTCGCCCTTATTCGACTCTATAGTGAAGTTCCTATTCTCTAGAAAGTATAGGAACT
TCTGAAGTGGGGAGAGACCACGCCGCGTGGATCCGGCTTACTAAAAGCCAGATAACAGTATG
CGTATTTGCGCGCTGATTTTTGCGGTATAAGAATATATACTCGGTAAGTGTATACCCGAAGTATG
TCAAAAAGAGGTATGCTATGAAGCAGCGTATTACAGTGACAGTTGACAGCGACAGCTATCAG
TTGCTCAAGGCATATATGATGTCAATATCTCCGGTCTGGTAAGCACAACCATGCAGAATGAA
GCCCGTCGTCTGCGTGCCGAACGCTGGAAAGCGGAAAATCAGGAAGGGATGGCTGAGGTCGC
CCGGTTTATTGAAATGAACGGCTCTTTTGCTGACGAGAACAGGGGCTGGTGAAATGCAGTTT
AAGGTTTACACCTATAAAAGAGAGAGCCGTTATCGTCTGTTTGTGGATGTACAGAGTGATAT
TATTGACACGCCCGGGCGACGGATGGTGATCCCCCTGGCCAGTGCACGTCTGCTGTCAGATA
AAGTCTCCCGTGAACTTTACCCGGTGGTGCATATCGGGGATGAAAGCTGGCGCATGATGACC
ACCGATATGGCCAGTGTGCCGGTTTCCGTTATCGGGGAAGAAGTGGCTGATCTCAGCCACCG
CGAAAATGACATCAAAAACGCCATTAACCTGATGTTCTGGGGAATATAAGGTCTCCAAAATG
AAGTGAAGTTCCTATACTTTCTAGAGAATAGGAACTTCTATAGTGAGTCGAATAAGGGCGAC
ACAAAA SEQ ID NO: 5 (directional cloning insert)
ATGGTCTGCCAAACACCTATAACACTATCATCAGCCGCATGGGTCAGTGGTACATGATTGAC
ATCTGCCTGGGTTACAAGGGTAAACGCAAGATCCACACTGTTATTTATGATTCCCTGAAAAA
GCTGCCGTTTCCGGTTAAAAAAATTGCTAAAGACTTCAAACTGACTGTTCTGAAAGGTGATA
TCGACTATCACAAAGAACGTCGGTCGGCTACAAAATCACGCCGGAAGAATACGCATACATT
AAAAACGATATCCAGATCATCGCCGAAGCCCTGCTGATCCAGTTCAAACAGGGTCTGGACCG
TATGACCGCAGGTTCCGATTCTCTGAAAGGTTTCAAGGATATCATTACCACTAAAAAGTTCA
AAAAGTTTTCCCGACTCTGTCTCTGGGTCTGGATAAGGAAGTTCGCTACGCCTACCGCGGT
GGCTTCACTTG SEQ ID NO: 6 (directional cloning 6 bp overhang cassette)
TTTTGTGTCGCCCTT<u>GACTGA</u>ATTCGACTCTTATATTCCCCAGAACATCAGGTTAATGGCGT
TTTTGATGTCATTTTCGCGGTGGCTGAGATCAGCCACTTCTTCCCCGATAACGGAAACCGGC
ACACTGGCCATATCGGTGGTCATCATGCGCCAGCTTTCATCCCCGATATGCACCACCGGGTA
AAGTTCACGGGAGACTTTATCTGACAGCAGACGTGCACTGGCCAGGGGATCACCATCCGTC
GCCCGGGCGTGTCAATAATATCACTCTGTACATCCACAAACAGACGATAACGGCTCTCTCTT

```
                              SEQUENCES
TTATAGGTGTAAACCTTAAACTGCATTTCACCAGCCCCTGTTCTCGTCAGCAAAAGAGCCGT
TCATTTCAATAAACCGGGCGACCTCAGCCATCCCTTCCTGATTTTCCGCTTTCCAGCGTTCG
GCACGCAGACGACGGGCTTCATTCTGCATGGTTGTGCTTACCAGACCGGAGATATTGACATC
ATATATGCCTTGAGCAACTGATAGCTGTCGCTGTCAACTGTCACTGTAATACGCTGCTTCAT
AGCATACCTCTTTTTGACATACTTCGGGTATACATATCAGTATATATTCTTATACCGCAAAA
ATCAGCGCGCAAATACGCATACTGTTATCTGGCTTTTAGTAAGCCGGATCCACGCGGCGTGA
GTCGAATAAGGGCGACACCCC

SEQ ID NO: 7 (directional cloning 4 bp overhang cassette)
TTTTGTGTCGCCCTTGACTATTCGACTCTTATATTCCCCAGAACATCAGGTTAATGGCGTTT
TTGATGTCATTTTCGCGGTGGCTGAGATCAGCCACTTCTTCCCCGATAACGGAAACCGGCAC
ACTGGCCATATCGGTGGTCATCATGCGCCAGCTTTCATCCCCGATATGCACCACCGGGTAAA
GTTCACGGGAGACTTTATCTGACAGCAGACGTGCACTGGCCAGGGGGATCACCATCCGTCGC
CCGGGCGTGTCAATAATATCACTCTGTACATCCACAAACAGACGATAACGGCTCTCTCTTTT
ATAGGTGTAAACCTTAAACTGCATTTCACCAGCCCCTGTTCTCGTCAGCAAAAGAGCCGTTC
ATTTCAATAAACCGGGCGACCTCAGCCATCCCTTCCTGATTTTCCGCTTTCCAGCGTTCGGC
ACGCAGACGACGGGCTTCATTCTGCATGGTTGTGCTTACCAGACCGGAGATATTGACATCAT
ATATGCCTTGAGCAACTGATAGCTGTCGCTGTCAACTGTCACTGTAATACGCTGCTTCATAG
CATACCTCTTTTTGACATACTTCGGGTATACATATCAGTATATATTCTTATACCGCAAAAAT
CAGCGCGCAAATACGCATACTGTTATCTGGCTTTTAGTAAGCCGGATCCACGCGGCGTGAGT
CGAATAAGGGCGACACCCC SEQ ID NO: 8 (directional cloning 2 bp overhang cassette)
TTTTGTGTCGCCCTTGAATTCGACTCTTATATTCCCCAGAACATCAGGTTAATGGCGTTTTT
GATGTCATTTTCGCGGTGGCTGAGATCAGCCACTTCTTCCCCGATAACGGAAACCGGCACAC
TGGCCATATCGGTGGTCATCATGCGCCAGCTTTCATCCCCGATATGCACCACCGGGTAAAGT
TCACGGGAGACTTTATCTGACAGCAGACGTGCACTGGCCAGGGGGATCACCATCCGTCGCCC
GGGCGTGTCAATAATATCACTCTGTACATCCACAAACAGACGATAACGGCTCTCTCTTTTAT
AGGTGTAAACCTTAAACTGCATTTCACCAGCCCCTGTTCTCGTCAGCAAAAGAGCCGTTCAT
TTCAATAAACCGGGCGACCTCAGCCATCCCTTCCTGATTTTCCGCTTTCCAGCGTTCGGCAC
GCAGACGACGGGCTTCATTCTGCATGGTTGTGCTTACCAGACCGGAGATATTGACATCATAT
ATGCCTTGAGCAACTGATAGCTGTCGCTGTCAACTGTCACTGTAATACGCTGCTTCATAGCA
TACCTCTTTTTGACATACTTCGGGTATACATATCAGTATATATTCTTATACCGCAAAAATCA
GCGCGCAAATACGCATACTGTTATCTGGCTTTTAGTAAGCCGGATCCACGCGGCGTGAGTCG
AATAAGGGCGACACCCC SEQ ID NO: 9 (MBP-topoisomerase)
MKTEEGKLVIWINGDKGYNGLAEVGKKFEKDTGIKVTVEHPDKLEEKFPQVAATGDGPDIIF
WAHDRFGGYAQSGLLAEITPDKAFQDKLYPFTWDAVRYNGKLIAYPIAVEALSLIYNKDLLP
NPPKTWEEIPALDKELKAKGKSALMFNLQEPYFTWPLIAADGGYAFKYENGKYDIKDVGVDN
AGAKAGLTFLVDLIKNKHMNADTDYSIAEAAFNKGETAMTINGPWAWSNIDTSKVNYGVTVL
PTFKGQPSKPFVGVLSAGINAASPNKELAKEFLENYLLTDEGLEAVNKDKPLGAVALKSYEE
ELAKDPRIAATMENAQKGEIMPNIPQMSAFWYAVRTAVINAASGRQTVDEALKDAQTNLEVL
FQGPRALFYKDGKLFTDNNFLNPVSDDNPAYEVLQHVKIPTHLTDVVVYEQTWEEALTRLIF
VGSDSKGRRQYFYGKMHVQNRNAKRDRIFVRVYNVMKRINCFINKNIKKSSTDSNYQLAVFM
LMETMFFIRFGKMKYLKENETVGLLTLKNKHIEISPDEIVIKFVGKDKVSHEFVVHKSNRLY
KPLLKLTDDSSPEEFLFNKLSERKVYECIKQFGIRIKDLRTYGVNYTFLYNFWTNVKSISPL
PSPKKLIALTIKQTAEVVGHTPSISKRAYMATTILEMVKDKNFLDVVSKTTFDEFLSIVVDH
VKSSTDG SEQ ID NO: 10 (NtAlwI-cassette)
TTTTGTGTCGCCCTTATTCGATCCTTATATTCCCCAGAACATCAGGTTAATGGCGTTTTTGA
TGTCATTTTCGCGGTGGCTGAGATCAGCCACTTCTTCCCCGATAACGGAAACCGGCACACTG
GCCATATCGGTGGTCATCATGCGCCAGCTTTCATCCCCGATATGCACCACCGGGTAAAGTTC
ACGGGAGACTTTATCTGACAGCAGACGTGCACTGGCCAGGGGGATCACCATCCGTCGCCCGG
GCGTGTCAATAATATCACTCTGTACATCCACAAACAGACGATAACGGCTCTCTCTTTTATAG
GTGTAAACCTTAAACTGCATTTCACCAGCCCCTGTTCTCGTCAGCAAAAGAGCCGTTCATTT
CAATAAACCGGGCGACCTCAGCCATCCCTTCCTGATTTTCCGCTTTCCAGCGTTCGGCACGC
AGACGACGGGCTTCATTCTGCATGGTTGTGCTTACCAGACCGGAGATATTGACATCATATAT
GCCTTGAGCAACTGATAGCTGTCGCTGTCAACTGTCACTGTAATACGCTGCTTCATAGCATA
CCTCTTTTTGACATACTTCGGGTATACATATCAGTATATATTCTTATACCGCAAAAATCAGC
GCGCAAATACGCATACTGTTATCTGGCTTTTAGTAAGCCGGATCGAATAAGGGCGACACCCC SEQ ID NO 11: (Topoisomerase Recognition Sequence)
5'-CAACATTTCCGTGTCGCCCTTATTCCCTTTTTTGCGGCAT-3'

SEQ ID NO 12: (Topoisomerase Recognition Sequence)
5'-GCTCGGCCCTTCCGG-3'

SEQ ID NO 13: (Topoisomerase Recognition Sequence)
5'-CGATCGCCCTTCCCA-3'

SEQ ID NO 14: (Topoisomerase Recognition Sequence)
5'-CAAAATCCCTTAACG-3'

SEQ ID NO 15: (Topoisomerase Recognition Sequence)
5'-TGAAGATCCTTTTTG-3'
```

-continued

SEQUENCES

SEQ ID NO 16: (Topoisomerase Recognition Sequence)
5'-ATTTTCTCCTTACGC-3'

SEQ ID NO 17: (Topoisomerase Recognition Sequence)
5'-GTGTCGCCCTTATTC-3'

SEQ ID NO 18: (Topoisomerase Recognition Sequence plus NtBstNBI nicking agent recognition sequence)
5'-CCCTTATTCGACTC-3'

SEQ ID NO 19: (Topoisomerase Recognition Sequence plus NtBstNBI nicking agent recognition sequence)
5'-CCCTTAGCTGACTC-3'

SEQ ID NO 20: (Topoisomerase Recognition Sequence plus NtAlwI nicking agent recognition sequence)
CCCTTATTCGATCC

REFERENCES

Each reference cited herein, whether patents, patent publication, literature references, or any other document, is hereby incorporated by reference in its entirety for all purposes.

Bernard, P. (1995). New ccdB positive-selection cloning vectors with kanamycin or chloramphenicol selectable markers. Gene 162, 159-160.

Bernard, P., Gabant, P., Bahassi, E. M., and Couturier, M. (1994). Positive-selection vectors using the F plasmid ccdB killer gene. Gene 148, 71-74.

Cha, J., Bishai, W., and Chandrasegaran, S. (1993). New vectors for direct cloning of PCR products. Gene 136, 369-370.

Cheng, C., Kussie, P., Pavletich, N., and Shuman, S. (1998). Conservation of structure and mechanism between eukaryotic topoisomerase I and site-specific recombinases. Cell 92, 841-850.

Gabant, P., Dreze, P. L., Van Reeth, T., Szpirer, J., and Szpirer, C. (1997). Bifunctional lacZ alpha-ccdB genes for selective cloning of PCR products. Biotechniques 23, 938-941.

Gabant, P., Szpirer, C. Y., Couturier, M., and Faelen, M. (1998). Direct selection cloning vectors adapted to the genetic analysis of gram-negative bacteria and their plasmids. Gene 207, 87-92.

Gabant, P., Van Reeth, T., Dreze, P. L., Faelen, M., Szpirer, C., and Szpirer, J. (2000). New positive selection system based on the parD (kis/kid) system of the R1 plasmid. Biotechniques 28, 784-788.

Galvao, T. C., and de Lorenzo, V. (2005). Adaptation of the yeast URA3 selection system to gram-negative bacteria and generation of a {delta}betCDE Pseudomonas putida strain. Appl Environ Microbiol 71, 883-892.

Geng, L., Xin, W., Huang, D. W., and Feng, G. (2006). A universal cloning vector using vaccinia topoisomerase I. Mol Biotechnol 33, 23-28.

Hartley, J. L., Temple, G. F., and Brasch, M. A. (2000). DNA cloning using in vitro site-specific recombination. Genome Res 10, 1788-1795.

Hartzog, P. E., Nicholson, B. P., and McCusker, J. H. (2005). Cytosine deaminase MX cassettes as positive/negative selectable markers in Saccharomyces cerevisiae. Yeast 22, 789-798.

Heyman, J. A., Cornthwaite, J., Foncerrada, L., Gilmore, J. R., Gontang, E., Hartman, K. J., Hernandez, C. L., Hood, R., Hull, H. M., Lee, W. Y., et al. (1999). Genome-scale cloning and expression of individual open reading frames using topoisomerase I-mediated ligation. Genome Res 9, 383-392.

Ichihara, Y., and Kurosawa, Y. (1993). Construction of new T vectors for direct cloning of PCR products. Gene 130, 153-154.

Ido, E., and Hayami, M. (1997). Construction of T-tailed vectors derived from a pUC plasmid: a rapid system for direct cloning of unmodified PCR products. Biosci Biotechnol Biochem 61, 1766-1767.

Knipfer, N., Seth, A., and Shrader, T. E. (1997). Unmarked gene integration into the chromosome of Mycobacterium smegmatis via precise replacement of the pyrF gene. Plasmid 37, 129-140.

Reyrat, J. M., Pelicic, V., Gicquel, B., and Rappuoli, R. (1998). Counterselectable markers: untapped tools for bacterial genetics and pathogenesis. Infect Immun 66, 4011-4017.

Shuman, S. (1991). Site-specific DNA cleavage by vaccinia virus DNA topoisomerase I. Role of nucleotide sequence and DNA secondary structure. J Biol Chem 266, 1796-1803.

Shuman, S. (1994). Novel approach to molecular cloning and polynucleotide synthesis using vaccinia DNA topoisomerase. J Biol Chem 269, 32678-32684.

Shuman, S. (1998). Polynucleotide ligase activity of eukaryotic topoisomerase I. Mol Cell, 741-748.

Shuman, S., and Prescott, J. (1990). Specific DNA cleavage and binding by vaccinia virus DNA topoisomerase I. J Biol Chem 265, 17826-17836.

Soderholm, J., Bevis, B. J., and Glick, B. S. (2001). Vector for pop-in/pop-out gene replacement in Pichia pastoris. Biotechniques 31, 306-310, 312.

Tamura, G. S., Bratt, D. S., Yim, H. H., and Nittayajarn, A. (2005). Use of glnQ as a counterselectable marker for creation of allelic exchange mutations in group B streptococci. Appl Environ Microbiol 71, 587-590.

Xu, Y., Lunnen, K. D., and Kong, H. (2001). Engineering a nicking endonuclease N.AlwI by domain swapping. Proc Natl Acad Sci USA 98, 12990-12995.

Yazynin, S., Lange, H., Mokros, T., Deyev, S., and Lemke, H. (1999). A new phagemid vector for positive selection of recombinants based on a conditionally lethal barnase gene. FEBS Lett 452, 351-354.

Zhou, M. Y., and Gomez-Sanchez, C. E. (2000). Universal TA cloning. Curr Issues Mol Biol 2, 1-7.

Zhu, Z., Samuelson, J. C., Zhou, J., Dore, A., and Xu, S. Y. (2004). Engineering strand-specific DNA nicking enzymes from the type IIS restriction endonucleases BsaI, BsmBI, and BsmAI. J Mol Biol 337, 573-583.

What is claimed is:

1. A composition comprising
   (i) a first polynucleotide having a first strand and a second strand, wherein said first polynucleotide is a first vector that comprises (a) a stuffer sequence, (b) a first topoisomerase recognition sequence and a second topoisomerase recognition sequence, (c) a first nicking agent recognition sequence and a second nicking agent recognition sequence, and a (d) selectable marker,
   (ii) a sequence-specific topoisomerase that reversibly cleaves a single strand of double stranded nucleic acid of the first polynucleotide at said first topoisomerase recognition sequence or said second topoisomerase recognition sequence, and
   (iii) a second polynucleotide, wherein
   the first topoisomerase recognition sequence and the first nicking agent recognition sequence comprises the sequence CCCTTNNNNGACTC (SEQ ID NO: 23) or GTGTCGCCCTTATTCGATCC (SEQ ID NO: 43), such that the first topoisomerase recognition sequence is in said first strand and said first nicking agent recognition sequence directs a nicking agent to nick said second strand of said first vector,
   the second topoisomerase recognition sequence is in within fifty nucleotides of the second nicking agent recognition sequence,
   the second topoisomerase recognition sequence is in said second strand and said second nicking agent recognition sequence directs a nicking agent to nick said first strand of said first vector,
   the stuffer sequence is between said first topoisomerase recognition sequence and said second topoisomerase recognition sequence,
   the stuffer sequence comprises a counter-selectable marker, a double stranded break site, a gene that encodes a fluorescent protein, or a gene that encodes a protein that participates in catalyzing a chromogenic reaction,
   said first vector is nicked in the first strand, in or close to said second nicking agent recognition sequence, and
   said first vector is nicked in the second strand, in or close to said first nicking agent recognition sequence, by a sequence-specific single-stranded nicking endonuclease.

2. The composition of claim 1, wherein said single-stranded nicking endonuclease is Nb.BsmI, Nt.BstNBI, Nb.BsrDI, Nt.BtsI or Nt.AlwI.

3. The composition of claim 1, wherein said sequence-specific topoisomerase is vaccinia topoisomerase I.

4. The composition of claim 3, wherein said sequence specific topoisomerase comprises an amino acid sequence identified as SEQ ID NO:9.

5. The composition of claim 1 wherein said second polynucleotide comprises a synthetic polynucleotide.

6. The composition of claim 5, wherein said first polynucleotide comprises a single-stranded overhang of between 1 and 50 nucleotides at one or both ends.

7. The composition of claim 6, wherein said first single-stranded overhang(s) comprise 1, 2, 3, 4, 5, 6, 7, 8, 9, or 10 nucleotides.

8. The composition of claim 1, wherein said stuffer sequence comprises the counter-selectable marker.

9. The composition of claim 1, wherein the stuffer sequence comprises the counter-selectable marker and wherein the counter-selectable marker is sacB, rpsL, tetAR, pheS, thyA, lacY, gata-1, ccdB, kid or barnase.

10. The composition of claim 1, wherein the stuffer sequence comprises the counter selectable marker and the counter-selectable marker is ccdB.

11. The composition of claim 1, wherein said stuffer sequence comprises a double stranded break site.

12. The composition of claim 1, wherein said second polynucleotide has been prepared by PCR amplification.

13. The composition of claim 1, wherein said first topoisomerase recognition sequence and said second topoisomerase recognition sequence each independently comprise:

```
                                          (SEQ ID NO 11)
CAACATTTCCGTGTCGCCCTTATTCCCTTTTTTGCGGCAT, (SEQ ID NO 12)
GCTCGGCCCTTCCGG, (SEQ ID NO: 13)
AGGCCCGCACCGATCGCCCTTCCCA, (SEQ ID NO: 14)
CAAAATCCCTTAACG, (SEQ ID NO: 15)
TGAAGATCCTT, (SEQ ID NO: 16)
ATTTTCTCCTTACGC,
or (SEQ ID NO: 17)
GTGTCGCCCTTATTC.
```

14. The composition of claim 1, wherein said first topoisomerase recognition sequence and said second topoisomerase recognition sequence each comprise GTGTCGCCCTTATTC (SEQ ID NO:17).

15. The composition of claim 1, wherein said first polynucleotide further comprises an origin of replication.

16. The composition of claim 1 wherein
the second topoisomerase recognition sequence and the second nicking agent recognition sequence comprise the sequence GAGTCNNNNAAGGG (SEQ ID NO:24) or GGATCGAATAAGGGCGACAC (SEQ ID NO:44).

17. The composition of claim 1 wherein
the first topoisomerase recognition sequence and the first nicking agent recognition sequence comprises any of the sequences of SEQ ID NO. 18 (CCCTTATTCGACTC), SEQ ID NO. 19 (CCCTTAGCTGACTC), SEQ ID NO. 20 (CCCTTATTCGATCC), SEQ ID NO. 52 (GTGTCGCCCTTGAATTCGACTC), SEQ ID NO: 25 (GTGTCGCCCTTGACTGAATTCGACTC) or SEQ ID NO: 50 (GTGTCGCCCTTGACTATTCGACTC).

18. A kit for cloning a second polynucleotide, comprising:
a. a first polynucleotide, wherein said first polynucleotide comprises
i. a selectable marker,
ii. a first topoisomerase recognition sequence and a second topoisomerase recognition sequence,
iii. a first nicking agent recognition sequence and a second nicking agent recognition sequence, and
iv. a stuffer sequence;
b. a sequence-specific topoisomerase that reversibly cleaves a single strand of double stranded nucleic acid of the first polynucleotide in the presence of said first topoisomerase recognition sequence or said second topoisomerase recognition sequence; and
c. instructions directing a user to combine the first polynucleotide, and the sequence-specific topoisomerase, wherein said second polynucleotide comprises a 5' hydroxyl on each end of the polynucleotide;
wherein
the first topoisomerase recognition sequence and the first nicking agent recognition sequence comprises the sequence CCCTTNNNNGACTC (SEQ ID NO: 23) or GTGTCGCCCTTATTCGATCC (SEQ ID NO: 43), such that the first topoisomerase recognition sequence is in said first strand and said first nicking agent recognition sequence directs a nicking agent to nick said second strand of said first vector,
the second topoisomerase recognition sequence is in within fifty nucleotides of the second nicking agent recognition sequence,
the second topoisomerase recognition sequence is in said second strand and said second nicking agent recognition sequence directs a nicking agent to nick said first strand of said first vector,
the stuffer sequence is between said first topoisomerase recognition sequence and said second topoisomerase recognition sequence,
the stuffer sequence comprises a counter-selectable marker, a double stranded break site, a gene that encodes a fluorescent protein, or a gene that encodes a protein that participates in catalyzing a chromogenic reaction,
said first vector is nicked in the first strand, in or close to said second nicking agent recognition sequence, and
said first vector is nicked in the second strand, in or close to said first nicking agent recognition sequence, by a sequence-specific single-stranded nicking endonuclease.

19. The kit of claim 18, wherein the first polynucleotide is nicked at each of the nicking agent recognition sequences.

20. The kit of claim 18, wherein said single-stranded nicking endonuclease is Nb.BsmI, Nt.BstNBI, Nb.BsrDI, Nt.BtsI or Nt.Alwi.

21. The kit of claim 18, wherein said sequence-specific topoisomerase is vaccinia topoisomerase 1.

22. The kit of claim 21, wherein said sequence specific topoisomerase comprises an amino acid sequence identified as SEQ ID NO:9.

23. The kit of claim 18, wherein the stuffer sequence comprises the counter-selectable marker and wherein the counter-selectable marker is sacB, rpsL, tetAR, pheS, thyA, lacY, gata-1, ccdB, kid or barnase.

24. The kit of claim 18, wherein the stuffer sequence comprises the counter-selectable marker and wherein the counter-selectable marker is ccdB.

25. The kit of claim 18, wherein said first topoisomerase recognition sequence and said second topoisomerase recognition sequence each independently comprise

```
                                          (SEQ ID NO: 11)
CAACATTTCCGTGTCGCCCTTATTCCCTTTTTTGCGGCAT, (SEQ ID NO: 12)
GCTCGGCCCTTCCGG, (SEQ ID NO: 13)
AGGCCCGCACCGATCGCCCTTCCCA, (SEQ ID NO: 14)
CAAAATCCCTTAACG, (SEQ ID NO: 15)
TGAAGATCCTT,
```

-continued

ATTTTCTCCTTACGC, (SEQ ID NO: 16)
or

GTGTCGCCCTTATTC. (SEQ ID NO: 17)

26. The kit of claim 18, wherein said first topoisomerase recognition sequence and said second topoisomerase recognition sequence comprise GTGTCGCCCTTATTC (SEQ ID NO:17).

27. The kit of claim 18, wherein said first polynucleotide further comprises an origin of replication.

28. A composition comprising
(i) a first polynucleotide having a first strand and a second strand, wherein said first polynucleotide is a first vector that comprises (a) a stuffer sequence, (b) a first topoisomerase recognition sequence and a second topoisomerase recognition sequence, (c) a first nicking agent recognition sequence and a second nicking agent recognition sequence, and a (d) selectable marker, wherein
the first topoisomerase recognition sequence and the first nicking agent recognition sequence comprises the sequence CCCTTNNNNGACTC (SEQ ID NO: 23) GTGTCGCCCTTATTCGATCC (SEQ ID NO: 43), such that the first topoisomerase recognition sequence is in said first strand and said first nicking agent recognition sequence directs a nicking agent to nick said second strand of said first vector,
the second topoisomerase recognition sequence is in within fifty nucleotides of the second nicking agent recognition sequence,
the second topoisomerase recognition sequence is in said second strand and said second nicking agent recognition sequence directs a nicking agent to nick said first strand of said first vector,
the stuffer sequence is between said first topoisomerase recognition sequence and said second topoisomerase recognition sequence,
the stuffer sequence comprises a counter-selectable marker, a double stranded break site, a gene that encodes a fluorescent protein, or a gene that encodes a protein that participates in catalyzing a chromogenic reaction.

* * * * *

SEQUENCE LISTING

<160> NUMBER OF SEQ ID NOS: 53

<210> SEQ ID NO 1
<211> LENGTH: 1611
<212> TYPE: DNA
<213> ORGANISM: Artificial Sequence
<220> FEATURE:
<223> OTHER INFORMATION: Vector Cloning Cassette

<400> SEQUENCE: 1

```
ggggccctta gctgactcta tagggaagtt cctattctct agaaagtata ggaacttctg      60
aagggggggag agacgacgcc gcgtggatcc ggcttactaa aagccagata acagtatgcg    120
tatttgcgcg ctgattttttg cggtataaga atatatactg atatgtatac ccgaagtatg    180
tcaaaaagag gtatgctatg aagcagcgta ttacagtgac agttgacagc gacagctatc    240
agttgctcaa ggcatatatg atgtcaatat ctccggtctg gtaagcacaa ccatgcagaa    300
tgaagcccgt cgtctgcgtg ccgaacgctg aaaagcggaa atcaggaag ggatggctga     360
ggtcgcccgg tttattgaaa tgaacggctc ttttgctgac gagaacaggg gctggtgaaa    420
tgcagtttaa ggtttacacc tataaaagag agagccgtta tcgtctgttt gtggatgtac    480
agagtgatat tattgacacg cccgggcgac ggatggtgat cccctggcc agtgcacgtc     540
tgctgtcaga taaagtctcc cgtgaacttt acccggtggt gcatatcggg gatgaaagct    600
ggcgcatgat gaccaccgat atggccagtg tgccggtttc cgttatcggg aagaagtgg    660
ctgatctcag ccaccgcgaa aatgacatca aaaacgccat taacctgatg ttctggggaa    720
tataaggtct ccgagcggta tcagctcact caaaggcggt aatacggtta ccacagaat    780
caggggataa cgcaggaaag aacatgtgag caaaaggcca gcaaaaggcc aggaaccgta    840
aaaaggccgc gttgctggcg tttttccata ggctccgccc cctgacgag catcacaaaa     900
atcgacgctc aagtcagagg tggcgaaacc cgacaggact ataaagatac caggcgtttc    960
cccctggaag ctccctcgtg cgctctcctg ttccgaccct gccgcttacc ggatacctgt   1020
ccgcctttct cccttcggga agcgtggcgc tttctcatag ctcacgctgt aggtatctca   1080
gttcggtgta ggtcgttcgc tccaagctgg gctgtgtgca cgaacccccc gttcagcccg   1140
accgctgcgc cttatccggt aactatcgtc ttgagtccaa cccggtaaga cacgacttat   1200
cgccactggc agcagccact ggtaacagga ttagcagagc gaggtatgta ggcggtgcta   1260
cagagttctt gaagtggtgg gctaactacg gctacactag aagaacagta tttggtatct   1320
gcgctctgct gaagccagtt accttcggaa aaagagttgg tagctcttga tccggcaaac   1380
aaaccaccgc tggtagcggt ggttttttttg tttgcaagca gcagattacg cgcagaaaaa   1440
aaggatctca agaagatcct ttgatctttt ctacggggtc tgacgctcag tggaacgacg   1500
cgcgcgtaac tcacgttaag ggattttggt catgagcgtc tccaaaatga agggaagttc   1560
ctatactttc tagagaatag gaacttctat agggagtcag ctaagggaaa a           1611
```

<210> SEQ ID NO 2
<211> LENGTH: 731
<212> TYPE: DNA
<213> ORGANISM: Artificial Sequence
<220> FEATURE:
<223> OTHER INFORMATION: RFP test fragment

<400> SEQUENCE: 2

```
ggtgttagga ggaaaaaaaa atggtttcca agggcgagga ggataacatg gctatcatta      60
aagagttcat gcgcttcaaa gttcacatgg agggttctgt taacggtcac gagttcgaga    120
```

```
tcgaaggcga aggcgagggc cgtccgtatg aaggcaccca gaccgccaaa ctgaaagtga      180
ctaaaggcgg cccgctgcct tttgcgtggg acatcctgag cccgcaattt atgtacggtt      240
ctaaagctta tgttaaacac ccagcggata tcccggacta tctgaagctg tcttttccgg      300
aaggtttcaa gtgggaacgc gtaatgaatt ttgaagatgg tggtgtcgtg accgtcactc      360
aggactcctc cctgcaggat ggcgagttca tctataaagt taaactgcgt ggtactaatt      420
ttccatctga tggcccggtg atgcagaaga agacgatggg ttgggaggcg tctagcgaac      480
gcatgtatcc ggaagatggt gcgctgaaag gcgaaattaa acagcgcctg aaactgaaag      540
atggcggcca ttatgacgct gaagtgaaaa ccacgtacaa agccaagaaa cctgtgcagc      600
tgcctggcgc gtacaatgtg aatattaaac tggacatcac ctctcataat gaagattata      660
cgatcgtaga gcaatatgag cgcgcggagg tcgtcattc taccggtggc atggatgagc      720
tgtacaaata a                                                          731
```

<210> SEQ ID NO 3
<211> LENGTH: 1057
<212> TYPE: DNA
<213> ORGANISM: Artificial Sequence
<220> FEATURE:
<223> OTHER INFORMATION: Beta lactamase test fragment

<400> SEQUENCE: 3

```
ataacttcgt atagcataca ttatacgaac ggtatcagaa ttggttaatt ggttgtaaca       60 ctgacccta tttgtttatt tttctaaata cattcaaata tgtatccgct catgagacaa      120
taaccctgat aaatgcttca ataatattga aaaggaaga atatgagtat tcaacatttc      180
cgtgtcgccc ttattccctt ttttgcggca ttttgccttc ctgttttgc tcacccagaa      240 acgctggtga agtaaaaga tgctgaagat cagttgggtg cacgagtggg ttacatcgaa      300
ctggatctca acagcggtaa gatccttgag agttttcgcc ccgaagaacg ttttccaatg      360
atgagcactt ttaaagttct gctatgtggc gcggtattat cccgtattga cgccgggcaa      420
gagcaactcg gtcgccgcat acactattct cagaatgact tggttgagta ctcaccagtc      480
acagaaaagc atcttacgga tggcatgaca gtaagagaat tatgcagtgc tgccataacc      540
atgagtgata acactgcggc caacttactt ctgacaacga tcggaggacc gaaggagcta      600
accgcttttt tgcacaacat ggggggatcat gtaactcgcc ttgatcgttg ggaaccggag      660
ctgaatgaag ccataccaaa cgacgagcgt gacaccacga tgcctgtagc gatggcaaca      720
acgttgcgca aactattaac tggcgaacta cttactctag cttcccggca acaattaata      780
gactggatgg aggcggataa agttgcagga ccacttctgc gctcggccct tccggctggc      840
tggtttattg ctgataaatc cggagccggt gagcgtggtt ctcgcggtat catcgcagcg      900
ctggggccag atggtaagcc ctcccgtatc gtagttatct acacgacggg gagtcaggca      960
actatggatg aacgaaatag acagatcgct gagataggtg cctcactgat taagcattgg     1020
taaataactt cgtataggat actttatacg aagttat                              1057
```

<210> SEQ ID NO 4
<211> LENGTH: 812
<212> TYPE: DNA
<213> ORGANISM: Artificial Sequence
<220> FEATURE:
<223> OTHER INFORMATION: Vector cloning cassette with pUC sites

<400> SEQUENCE: 4

```
gggggtgtcg cccttattcg actctatagt gaagttccta ttctctagaa agtataggaa    60
cttctgaagt ggggagagac cacgccgcgt ggatccggct tactaaaagc cagataacag   120
tatgcgtatt tgcgcgctga tttttgcggt ataagaatat atactgatat gtatacccga   180
agtatgtcaa aaagaggtat gctatgaagc agcgtattac agtgacagtt gacagcgaca   240
gctatcagtt gctcaaggca tatatgatgt caatatctcc ggtctggtaa gcacaaccat   300
gcagaatgaa gcccgtcgtc tgcgtgccga acgctggaaa gcggaaaatc aggaagggat   360
ggctgaggtc gcccggttta ttgaaatgaa cggctctttt gctgacgaga cagggggctg   420
gtgaaatgca gtttaaggtt tacacctata aagagagag ccgttatcgt ctgtttgtgg    480
atgtacagag tgatattatt gacacgcccg ggcgacggat ggtgatcccc ctggccagtg   540
cacgtctgct gtcagataaa gtctcccgtg aactttaccc ggtggtgcat atcggggatg   600
aaagctggcg catgatgacc accgatatgg ccagtgtgcc ggtttccgtt atcggggaag   660
aagtggctga tctcagccac cgcgaaaatg acatcaaaaa cgccattaac ctgatgttct   720
ggggaatata aggtctccaa aatgaagtga agttcctata ctttctagag aataggaact   780
tctatagtga gtcgaataag ggcgacacaa aa                                 812

<210> SEQ ID NO 5
<211> LENGTH: 445
<212> TYPE: DNA
<213> ORGANISM: Artificial Sequence
<220> FEATURE:
<223> OTHER INFORMATION: Directional cloning insert

<400> SEQUENCE: 5
atggtctgcc aaacacctat aacactatca tcagccgcat gggtcagtgg tacatgattg    60
acatctgcct gggttacaag ggtaaacgca agatccacac tgttatttat gattccctga   120
aaagctgccg gtttccggtt aaaaaaattg ctaaagactt caaactgact gttctgaaag   180
gtgatatcga ctatcacaaa gaacgtccgg tcggctacaa aatcacgccg gaagaatacg   240
catacattaa aaacgatatc cagatcatcg ccgaagccct gctgatccag ttcaaacagg   300
gtctggaccg tatgaccgca ggttccgatt ctctgaaagg tttcaaggat atcattacca   360
ctaaaaagtt caaaaaagtt ttcccgactc tgtctctggg tctggataag gaagttcgct   420
acgcctaccg cggtggcttc acttg                                         445

<210> SEQ ID NO 6
<211> LENGTH: 703
<212> TYPE: DNA
<213> ORGANISM: Artificial Sequence
<220> FEATURE:
<223> OTHER INFORMATION: Directional cloning 6bp overhang cassette

<400> SEQUENCE: 6
ttttgtgtcg cccttgactg aattcgactc ttatattccc cagaacatca ggttaatggc    60
gtttttgatg tcatttttcgc ggtggctgag atcagccact tcttccccga taacggaaac   120
cggcacactg gccatatcgg tggtcatcat gcgccagctt tcatccccga tatgcaccac   180
cgggtaaagt tcacgggaga ctttatctga cagcagacgt gcactggcca ggggatcac    240 catccgtcgc ccgggcgtgt caataatatc actctgtaca tccacaaaca gacgataacg   300
gctctctctt ttataggtgt aaaccttaaa ctgcatttca ccagcccctg ttctcgtcag   360
caaaagagcc gttcatttca ataaccgggc gacctcagc catcccttcc tgattttccg   420
cttcccagcg ttcggcacgc agacgacggg cttcattctg catggttgtg cttaccagac   480
```

```
cggagatatt gacatcatat atgccttgag caactgatag ctgtcgctgt caactgtcac    540
tgtaatacgc tgcttcatag catacctctt tttgacatac ttcgggtata catatcagta    600
tatattctta taccgcaaaa atcagcgcgc aaatacgcat actgttatct ggcttttagt    660
aagccggatc cacgcggcgt gagtcgaata agggcgacac ccc                     703

<210> SEQ ID NO 7
<211> LENGTH: 701
<212> TYPE: DNA
<213> ORGANISM: Artificial Sequence
<220> FEATURE:
<223> OTHER INFORMATION: Directional cloning 4bp overhang cassette

<400> SEQUENCE: 7
ttttgtgtcg cccttgacta ttcgactctt atattcccca gaacatcagg ttaatggcgt     60
ttttgatgtc attttcgcgg tggctgagat cagccacttc ttccccgata acggaaaccg    120
gcacactggc catatcggtg gtcatcatgc gccagctttc atccccgata tgcaccaccg    180
ggtaaagttc acgggagact ttatctgaca gcagacgtgc actggccagg gggatcacca    240
tccgtcgccc gggcgtgtca ataatatcac tctgtacatc cacaaacaga cgataacggc    300
tctctctttt ataggtgtaa accttaaact gcatttcacc agcccctgtt ctcgtcagca    360
aaagagccgt tcatttcaat aaaccgggcg acctcagcca tcccttcctg attttccgct    420
ttccagcgtt cggcacgcag acgacgggct tcattctgca tggttgtgct taccagaccg    480
gagatattga catcatatat gccttgagca actgatagct gtcgctgtca actgtcactg    540
taatacgctg cttcatagca tacctctttt tgacatactt cgggtataca tatcagtata    600
tattcttata ccgcaaaaat cagcgcgcaa atacgcatac tgttatctgg cttttagtaa    660
gccggatcca cgcggcgtga gtcgaataag ggcgacaccc c                       701

<210> SEQ ID NO 8
<211> LENGTH: 699
<212> TYPE: DNA
<213> ORGANISM: Artificial Sequence
<220> FEATURE:
<223> OTHER INFORMATION: Directional cloning 2bp overhang cassette

<400> SEQUENCE: 8
ttttgtgtcg cccttgaatt cgactcttat attccccaga acatcaggtt aatggcgttt     60
ttgatgtcat tttcgcggtg gctgagatca gccacttctt ccccgataac ggaaaccggc    120
acactggcca tatcggtggt catcatgcgc cagctttcat ccccgatatg caccaccggg    180
taaagttcac gggactttt atctgacagc agacgtgcac tggccagggg gatcaccatc    240
cgtcgcccgg gcgtgtcaat aatatcactc tgtacatcca caaacagacg ataacggctc    300
tctcttttat aggtgtaaac cttaaactgc atttcaccag cccctgttct cgtcagcaaa    360
agagccgttc atttcaataa accgggcgac ctcagccatc ccttcctgat tttccgcttt    420
ccagcgttcg gcacgcagac gacgggcttc attctgcatg gttgtgctta ccagaccgga    480
gatattgaca tcatatatgc cttgagcaac tgatagctgt cgctgtcaac tgtcactgta    540
atacgctgct tcatagcata cctcttttg acatacttcg ggtatacata tcagtatata    600
ttcttatacc gcaaaaatca gcgcgcaaat acgcatactg ttatctggct tttagtaagc    660
cggatccacg cggcgtgagt cgaataaggg cgacacccc                          699

<210> SEQ ID NO 9
```

<211> LENGTH: 689
<212> TYPE: PRT
<213> ORGANISM: Artificial Sequence
<220> FEATURE:
<223> OTHER INFORMATION: MBP-topoisomerase

<400> SEQUENCE: 9

```
Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Leu Glu Val Leu Phe Gln Gly Pro Arg Ala Leu Phe Tyr Lys Asp Gly
    370                 375                 380
```

Lys Leu Phe Thr Asp Asn Asn Phe Leu Asn Pro Val Ser Asp Asp Asn
385                 390                 395                 400

Pro Ala Tyr Glu Val Leu Gln His Val Lys Ile Pro Thr His Leu Thr
            405                 410                 415

Asp Val Val Tyr Glu Gln Thr Trp Glu Glu Ala Leu Thr Arg Leu
        420                 425                 430

Ile Phe Val Gly Ser Asp Ser Lys Gly Arg Arg Gln Tyr Phe Tyr Gly
            435                 440                 445

Lys Met His Val Gln Asn Arg Asn Ala Lys Arg Asp Arg Ile Phe Val
        450                 455                 460

Arg Val Tyr Asn Val Met Lys Arg Ile Asn Cys Phe Ile Asn Lys Asn
465                 470                 475                 480

Ile Lys Lys Ser Ser Thr Asp Ser Asn Tyr Gln Leu Ala Val Phe Met
            485                 490                 495

Leu Met Glu Thr Met Phe Phe Ile Arg Phe Gly Lys Met Lys Tyr Leu
                500                 505                 510

Lys Glu Asn Glu Thr Val Gly Leu Leu Thr Leu Lys Asn Lys His Ile
            515                 520                 525

Glu Ile Ser Pro Asp Glu Ile Val Ile Lys Phe Val Gly Lys Asp Lys
            530                 535                 540

Val Ser His Glu Phe Val Val His Lys Ser Asn Arg Leu Tyr Lys Pro
545                 550                 555                 560

Leu Leu Lys Leu Thr Asp Asp Ser Ser Pro Glu Glu Phe Leu Phe Asn
                565                 570                 575

Lys Leu Ser Glu Arg Lys Val Tyr Glu Cys Ile Lys Gln Phe Gly Ile
            580                 585                 590

Arg Ile Lys Asp Leu Arg Thr Tyr Gly Val Asn Tyr Thr Phe Leu Tyr
            595                 600                 605

Asn Phe Trp Thr Asn Val Lys Ser Ile Ser Pro Leu Pro Ser Pro Lys
        610                 615                 620

Lys Leu Ile Ala Leu Thr Ile Lys Gln Thr Ala Glu Val Val Gly His
625                 630                 635                 640

Thr Pro Ser Ile Ser Lys Arg Ala Tyr Met Ala Thr Thr Ile Leu Glu
                645                 650                 655

Met Val Lys Asp Lys Asn Phe Leu Asp Val Val Ser Lys Thr Thr Phe
            660                 665                 670

Asp Glu Phe Leu Ser Ile Val Val Asp His Val Lys Ser Ser Thr Asp
        675                 680                 685

Gly

<210> SEQ ID NO 10
<211> LENGTH: 682
<212> TYPE: DNA
<213> ORGANISM: Artificial Sequence
<220> FEATURE:
<223> OTHER INFORMATION: NtAlwI-cassette

<400> SEQUENCE: 10
ttttgtgtcg cccttattcg atccttatat tccccagaac atcaggttaa tggcgttttt    60
gatgtcattt tcgcggtggc tgagatcagc cacttcttcc ccgataacgg aaaccggcac   120
actggccata tcggtggtca tcatgcgcca gctttcatcc ccgatatgca ccaccgggta   180
aagttcacgg gagactttat ctgacagcag acgtgcactg gcagggggga tcaccatccg   240
tcgcccgggc gtgtcaataa tatcactctg tacatccaca aacagacgat aacggctctc   300

-continued

```
tcttttatag gtgtaaacct taaactgcat ttcaccagcc cctgttctcg tcagcaaaag    360
agccgttcat ttcaataaac cgggcgacct cagccatccc ttcctgattt tccgctttcc    420
agcgttcggc acgcagacga cgggcttcat tctgcatggt tgtgcttacc agaccggaga    480
tattgacatc atatatgcct tgagcaactg atagctgtcg ctgtcaactg tcactgtaat    540
acgctgcttc atagcatacc tcttttgac atacttcggg tatacatatc agtatatatt     600
cttataccgc aaaatcagc gcgcaaatac gcatactgtt atctggcttt tagtaagccg     660
gatcgaataa gggcgacacc cc                                             682
```

```
<210> SEQ ID NO 11
<211> LENGTH: 40
<212> TYPE: DNA
<213> ORGANISM: Artificial Sequence
<220> FEATURE:
<223> OTHER INFORMATION: Topoisomerase Recognition Sequence

<400> SEQUENCE: 11
caacatttcc gtgtcgccct tattcccttt tttgcggcat                          40

<210> SEQ ID NO 12
<211> LENGTH: 15
<212> TYPE: DNA
<213> ORGANISM: Artificial Sequence
<220> FEATURE:
<223> OTHER INFORMATION: Topoisomerase Recognition Sequence

<400> SEQUENCE: 12
gctcggccct tccgg                                                     15

<210> SEQ ID NO 13
<211> LENGTH: 25
<212> TYPE: DNA
<213> ORGANISM: Artificial Sequence
<220> FEATURE:
<223> OTHER INFORMATION: Topoisomerase Recognition Sequence

<400> SEQUENCE: 13
aggcccgacc cgatcgccct tccca                                          25

<210> SEQ ID NO 14
<211> LENGTH: 15
<212> TYPE: DNA
<213> ORGANISM: Artificial Sequence
<220> FEATURE:
<223> OTHER INFORMATION: Topoisomerase Recognition Sequence

<400> SEQUENCE: 14
caaaatccct taacg                                                     15

<210> SEQ ID NO 15
<211> LENGTH: 15
<212> TYPE: DNA
<213> ORGANISM: Artificial Sequence
<220> FEATURE:
<223> OTHER INFORMATION: Topoisomerase recognition sequence

<400> SEQUENCE: 15
tgaagatcct ttttg                                                     15

<210> SEQ ID NO 16
<211> LENGTH: 15
<212> TYPE: DNA
```

```
<213> ORGANISM: Artificial Sequence
<220> FEATURE:
<223> OTHER INFORMATION: Topoisomerase recognition sequence

<400> SEQUENCE: 16
attttctcct tacgc                                                    15

<210> SEQ ID NO 17
<211> LENGTH: 15
<212> TYPE: DNA
<213> ORGANISM: Artificial Sequence
<220> FEATURE:
<223> OTHER INFORMATION: Topoisomerase recognition sequence

<400> SEQUENCE: 17
gtgtcgccct tattc                                                    15

<210> SEQ ID NO 18
<211> LENGTH: 14
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 18
cccttattcg actc                                                     14

<210> SEQ ID NO 19
<211> LENGTH: 14
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 19
cccttagctg actc                                                     14

<210> SEQ ID NO 20
<211> LENGTH: 14
<212> TYPE: DNA
<213> ORGANISM: Artificial Sequence
<220> FEATURE:
<223> OTHER INFORMATION: Topoisomerase recognition sequence plus NtAlWI
      nicking agent recognition sequence

<400> SEQUENCE: 20
cccttattcg atcc                                                     14

<210> SEQ ID NO 21
<211> LENGTH: 10
<212> TYPE: DNA
<213> ORGANISM: Artificial Sequence
<220> FEATURE:
<223> OTHER INFORMATION: Topoisomerase recognition sequence
<220> FEATURE:
<221> NAME/KEY: misc_feature
<222> LOCATION: (6)...(10)
<223> OTHER INFORMATION: n is any nucleotide

<400> SEQUENCE: 21 cccttnnnnn                                                          10

<210> SEQ ID NO 22
<211> LENGTH: 10
<212> TYPE: DNA
```

-continued

```
<213> ORGANISM: Artificial Sequence
<220> FEATURE:
<223> OTHER INFORMATION: Topoisomerase recognition sequence
<220> FEATURE:
<221> NAME/KEY: misc_feature
<222> LOCATION: (1)...(5)
<223> OTHER INFORMATION: n is any nucleotide

<400> SEQUENCE: 22 nnnnnaaggg                                                          10

<210> SEQ ID NO 23
<211> LENGTH: 14
<212> TYPE: DNA
<213> ORGANISM: Artificial Sequence
<220> FEATURE:
<223> OTHER INFORMATION: Topoisomerase recognition sequence
<220> FEATURE:
<221> NAME/KEY: misc_feature
<222> LOCATION: (6)...(9)
<223> OTHER INFORMATION: n is any nucleotide

<400> SEQUENCE: 23
cccttnnnng actc                                                     14

<210> SEQ ID NO 24
<211> LENGTH: 14
<212> TYPE: DNA
<213> ORGANISM: Artificial Sequence
<220> FEATURE:
<223> OTHER INFORMATION: Topoisomerase recognition sequence
<220> FEATURE:
<221> NAME/KEY: misc_feature
<222> LOCATION: (6)...(9)
<223> OTHER INFORMATION: n is any nucleotide

<400> SEQUENCE: 24
gagtcnnnna aggg                                                     14

<210> SEQ ID NO 25
<211> LENGTH: 26
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 25
gtgtcgccct tgactgaatt cgactc                                        26

<210> SEQ ID NO 26
<211> LENGTH: 26
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 26
gagtcgaatt cagtcaaggg gcacac                                        26

<210> SEQ ID NO 27
<211> LENGTH: 20
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence
```

<400> SEQUENCE: 27
gagtcgaata agggcgacac                                               20

<210> SEQ ID NO 28
<211> LENGTH: 20
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 28
gtgtcgccct tattcgactc                                               20

<210> SEQ ID NO 29
<211> LENGTH: 11
<212> TYPE: DNA
<213> ORGANISM: Artificial Sequence
<220> FEATURE:
<223> OTHER INFORMATION: Topoisomerase adduct sequence

<400> SEQUENCE: 29
gtgtcgccct t                                                        11

<210> SEQ ID NO 30
<211> LENGTH: 17
<212> TYPE: DNA
<213> ORGANISM: Artificial Sequence
<220> FEATURE:
<223> OTHER INFORMATION: Topoisomerase adduct sequence

<400> SEQUENCE: 30
tcagtcaagg ggcacac                                                  17

<210> SEQ ID NO 31
<211> LENGTH: 11
<212> TYPE: DNA
<213> ORGANISM: Artificial Sequence
<220> FEATURE:
<223> OTHER INFORMATION: Topoisomerase adduct sequence

<400> SEQUENCE: 31
aagggcgaca c                                                        11

<210> SEQ ID NO 32
<211> LENGTH: 11
<212> TYPE: DNA
<213> ORGANISM: Artificial Sequence
<220> FEATURE:
<223> OTHER INFORMATION: Topoisomerase adduct sequence

<400> SEQUENCE: 32
gtgtcgccct t                                                        11

<210> SEQ ID NO 33
<211> LENGTH: 15
<212> TYPE: DNA
<213> ORGANISM: Artificial Sequence
<220> FEATURE:
<223> OTHER INFORMATION: Topoisomerase adduct sequence

<400> SEQUENCE: 33
agtcaagggg cacac                                                    15

<210> SEQ ID NO 34

```
<211> LENGTH: 13
<212> TYPE: DNA
<213> ORGANISM: Artificial Sequence
<220> FEATURE:
<223> OTHER INFORMATION: Topoisomerase adduct sequence

<400> SEQUENCE: 34
tcaaggggca cac                                                          13

<210> SEQ ID NO 35
<211> LENGTH: 21
<212> TYPE: DNA
<213> ORGANISM: Artificial Sequence
<220> FEATURE:
<223> OTHER INFORMATION: Topoisomerase recognition sequence with spacer
<220> FEATURE:
<221> NAME/KEY: misc_feature
<222> LOCATION: 21
<223> OTHER INFORMATION: n is any nucleotide

<400> SEQUENCE: 35
gtgtcgccct tattcgactc n                                                 21

<210> SEQ ID NO 36
<211> LENGTH: 21
<212> TYPE: DNA
<213> ORGANISM: Artificial Sequence
<220> FEATURE:
<223> OTHER INFORMATION: Topoisomerase recognition sequence with spacer
<220> FEATURE:
<221> NAME/KEY: misc_feature
<222> LOCATION: 1
<223> OTHER INFORMATION: n is any nucleotide

<400> SEQUENCE: 36
ngagtcgaat aagggggcaca c                                                21

<210> SEQ ID NO 37
<211> LENGTH: 20
<212> TYPE: DNA
<213> ORGANISM: Artificial Sequence
<220> FEATURE:
<223> OTHER INFORMATION: Topoisomerase recognition sequence with spacer

<400> SEQUENCE: 37
gagtcgaata agggcgacac                                                   20

<210> SEQ ID NO 38
<211> LENGTH: 20
<212> TYPE: DNA
<213> ORGANISM: Artificial Sequence
<220> FEATURE:
<223> OTHER INFORMATION: Topoisomerase recognition sequence with spacer

<400> SEQUENCE: 38
gtgtcgccct tattcgactc                                                   20

<210> SEQ ID NO 39
<211> LENGTH: 15
<212> TYPE: DNA
<213> ORGANISM: Artificial Sequence
<220> FEATURE:
<223> OTHER INFORMATION: Topoisomerase recognition sequence with spacer
<220> FEATURE:
<221> NAME/KEY: misc_feature
<222> LOCATION: 15
<223> OTHER INFORMATION: n is any nucleotide

<400> SEQUENCE: 39
```
cccttagctg actcn                                                         15

<210> SEQ ID NO 40
<211> LENGTH: 15
<212> TYPE: DNA
<213> ORGANISM: Artificial Sequence
<220> FEATURE:
<223> OTHER INFORMATION: Topoisomerase recognition sequence with spacer
<220> FEATURE:
<221> NAME/KEY: misc_feature
<222> LOCATION: 1
<223> OTHER INFORMATION: n is any nucleotide

<400> SEQUENCE: 40
ngagtcagct aaggg                                                         15

<210> SEQ ID NO 41
<211> LENGTH: 14
<212> TYPE: DNA
<213> ORGANISM: Artificial Sequence
<220> FEATURE:
<223> OTHER INFORMATION: Topoisomerase recognition sequence with spacer

<400> SEQUENCE: 41
gagtcagcta aggg                                                          14

<210> SEQ ID NO 42
<211> LENGTH: 14
<212> TYPE: DNA
<213> ORGANISM: Artificial Sequence
<220> FEATURE:
<223> OTHER INFORMATION: Topoisomerase recognition sequence with spacer

<400> SEQUENCE: 42
cccttagctg actc                                                          14

<210> SEQ ID NO 43
<211> LENGTH: 20
<212> TYPE: DNA
<213> ORGANISM: Artificial Sequence
<220> FEATURE:
<223> OTHER INFORMATION: Topoisomerase recognition sequence plus NtAlwI
      nicking agent recognition sequence

<400> SEQUENCE: 43
gtgtcgccct tattcgatcc                                                    20

<210> SEQ ID NO 44
<211> LENGTH: 20
<212> TYPE: DNA
<213> ORGANISM: Artificial Sequence
<220> FEATURE:
<223> OTHER INFORMATION: Topoisomerase recognition sequence plus NtAlwI
      nicking agent recognition sequence

<400> SEQUENCE: 44
ggatcgaata agggcgacac                                                    20

<210> SEQ ID NO 45
<211> LENGTH: 13
<212> TYPE: DNA
<213> ORGANISM: Artificial Sequence
<220> FEATURE:
<223> OTHER INFORMATION: Topoisomerase recognition sequence following
      cloning

<400> SEQUENCE: 45

-continued

```
gtgtcgccct tga                                              13

<210> SEQ ID NO 46
<211> LENGTH: 13
<212> TYPE: DNA
<213> ORGANISM: Artificial Sequence
<220> FEATURE:
<223> OTHER INFORMATION: Topoisomerase recognition sequence following
      cloning
<220> FEATURE:
<221> NAME/KEY: misc_feature
<222> LOCATION: (1)...(2)
<223> OTHER INFORMATION: n is any nucleotide

<400> SEQUENCE: 46
nnaagggcga cac                                              13

<210> SEQ ID NO 47
<211> LENGTH: 13
<212> TYPE: DNA
<213> ORGANISM: Artificial Sequence
<220> FEATURE:
<223> OTHER INFORMATION: Topoisomerase recognition sequence following
      cloning
<220> FEATURE:
<221> NAME/KEY: misc_feature
<222> LOCATION: (12)...(13)
<223> OTHER INFORMATION: n is any nucleotide

<400> SEQUENCE: 47
gtgtcgccct tnn                                              13

<210> SEQ ID NO 48
<211> LENGTH: 13
<212> TYPE: DNA
<213> ORGANISM: Artificial Sequence
<220> FEATURE:
<223> OTHER INFORMATION: Topoisomerase recognition sequence
<220> FEATURE:
<221> NAME/KEY: misc_feature
<222> LOCATION: (1)...(2)
<223> OTHER INFORMATION: n is any nucleotide

<400> SEQUENCE: 48
nnaagggcga cac                                              13

<210> SEQ ID NO 49
<211> LENGTH: 14
<212> TYPE: DNA
<213> ORGANISM: Artificial Sequence
<220> FEATURE:
<223> OTHER INFORMATION: Released counter-selectable marker

<400> SEQUENCE: 49
ggatcgaata aggg                                             14

<210> SEQ ID NO 50
<211> LENGTH: 24
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 50
gtgtcgccct tgactattcg actc                                  24
```

```
<210> SEQ ID NO 51
<211> LENGTH: 24
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 51
gagtcgaata gtcaagggcg acac                                              24

<210> SEQ ID NO 52
<211> LENGTH: 22
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 52
gtgtcgccct tgaattcgac tc                                                22

<210> SEQ ID NO 53
<211> LENGTH: 22
<212> TYPE: DNA
<213> ORGANISM: Artificial Sequence
<220> FEATURE:
<223> OTHER INFORMATION: Topoisomerase recognition sequence plus
      NtBstNBI nicking agent recognition sequence

<400> SEQUENCE: 53
gagtcgaatt caagggcgac ac                                                22
```